United States Patent
Lebel

(10) Patent No.: US 9,328,076 B2
(45) Date of Patent: May 3, 2016

(54) MOLECULAR GLASSES WITH FUNCTIONALIZABLE GROUPS

(71) Applicant: Her Majesty the Queen in Right of Canada as represented by the Minister of National Defence, Ottawa (CA)

(72) Inventor: Olivier Lebel, Kingston (CA)

(73) Assignee: HER MAJESTY IN THE RIGHT OF CANADA AS REPRESENTED BY THE MINISTER OF DEFENSE, Ottawa, Ontario (CA)

( * ) Notice: Subject to any disclaimer, the term of this patent is extended or adjusted under 35 U.S.C. 154(b) by 0 days.

(21) Appl. No.: 14/630,056

(22) Filed: Feb. 24, 2015

(65) Prior Publication Data

US 2015/0232433 A1    Aug. 20, 2015

Related U.S. Application Data

(62) Division of application No. 13/714,942, filed on Dec. 14, 2012.

(30) Foreign Application Priority Data

Dec. 16, 2011   (CA) ...................................... 2762434

(51) Int. Cl.
C07D 251/50    (2006.01)
C07D 251/70    (2006.01)

(52) U.S. Cl.
CPC ............ *C07D 251/70* (2013.01); *C07D 251/50* (2013.01)

(58) Field of Classification Search
CPC .................................................. C07D 251/50
See application file for complete search history.

(56) References Cited

U.S. PATENT DOCUMENTS

2002/0103195 A1 *   8/2002   Bonham .............. C07D 251/50
                                                         514/236.2

OTHER PUBLICATIONS

Hancock, B.C.; Zografi, G. "Characteristics and Significance of the Amorphous State in Pharmaceutical Systems", J. Pharm. Sci. 1997, 86, 1-12.
Yu, L. "Amorphous pharmaceutical solids: preparation, characterization and stabilization", Adv. Drug Deliv. Rev. 2001, 48, 27-42.
Shirota, Y. "Photo- and electroactive amorphous molecular materials—molecular design, syntheses, reactions, properties, and applications", J. Mater. Chem. 2005, 15, 75-93.
Dai, J; Chang, S,W.; Hamad, A.; Yang, D.; Felix, N.; Ober, C.K.; "Molecular Glass Resists for High-Resolution Patterning", Chem. Mater. 2006, 18, 3404-3411.
Grazulevicius, J.V., "Chargw tranbsporting polymers and molecular glasses for optoelectronic applications", Polym. Adv. Technol. 2006, 17, 694-696.
Ediger, M.D.; Angell, C.A.; Nagel, S.R. "Supercooled Liquids and Glasses", J. Phys. Chem. 1996, 100, 13200-13212.
Ishow, E. et al. "Versatile Synthesis of Small NLO-Active Molecules Forming Amorphous Materials with Spontaneous Second-Order NLO Response", J. Am. Chem. Soc. 2003, 125, 15744.
Tanino, T. et al. "Creation of azobenzene-based photochromic amorphous molecular materials-synthesis, glass-forming properties and photochromic response", J. Mater. Chem. 2007.
Nagahama, D. et al. "Synthesis and Photochromic Response of a New Photochromic Amorphous Molecular Material Based on Spirooxazine", J. Photopolym. Sci. Technol. 2008, 21, 755.
Wuest, J.D.; Lebel, O.; "Anarchy in the solid state: structural dependence on glass-forming ability in triazihe-based molecular glasses", Tetrahedron, 2009, 65, 7393-7402.
Wang, R.; Pellerin, C.; Lebel, O. "Role of Hydrogen Bonding in the Formation of Glasses by Small Molecules: A Triazine Case Study", J. Mater. Chem., 2009, 19, 2747-2753.
Plante, A. et al. "Tgand Rheological Properties of Triazine-Based Molecular Glasses: Incriminating Evidence Against Hydrogen Bonds", J. Phys. Chem. B, 2009, 113, 14884-14891.
Meunier, A.; Lebel, O. "A Glass Forming Module for Organic Molecules: Making Tetraphenylporphyrin Lose its Crystalinity", Org. Lett., 2010, 12, 1896-1899.
Shirota, Y. "Organic Materials for electronic and optoelectronic devices", J. Mater. Chem. 2000, 10, 1-25.
Kuroki et al. (CAPLUS Abstract JP 44030098 (Published 1970)).
Kubota et al. (CAPLUS Abstract of WO 2003066099 (Published 2003)).
Eren et al. Tetrahedron, 68, 2012, p. 10130-10144.

* cited by examiner

*Primary Examiner* — Robert Havlin
(74) *Attorney, Agent, or Firm* — Philip A. Swain; IPSIS, Inc.

(57) ABSTRACT

Disclosed herein is a compound having Formula I:

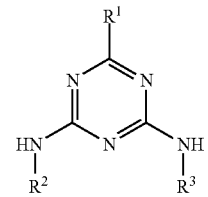

or a salt thereof, in which $R^1$, $R^2$ and $R^3$ are as defined herein. Also disclosed are processes to prepare compounds of Formula I and use of Formula I to prepare stable glassy phases.

10 Claims, No Drawings

MOLECULAR GLASSES WITH FUNCTIONALIZABLE GROUPS

CROSS-REFERENCE TO RELATED APPLICATIONS

The present is a divisional application of pending U.S. patent application Ser. No. 13/714,942, filed on Dec. 14, 2012, which claims priority from previously filed Canadian patent application No. CA 2,762,434, filed on Dec. 16, 2011, the contents of which are hereby incorporated by reference in their entirety.

TECHNICAL FIELD

The present discovery relates generally to molecular glasses, and more particularly to 1,3,5-triazine derivatives as glass-inducing moieties.

BACKGROUND

Several applications require materials to be processed into a glassy, amorphous form. For this purpose, inorganic glasses ($SiO_2$, for example), or polymers, are often employed, but small molecules are an appealing alternative because they are typically easier to purify, characterize and process due to the fact that they are monodisperse species. Small molecules capable of readily forming glassy phases at ambient temperatures are called molecular glasses or amorphous molecular materials, and currently see widespread use in optoelectronics (primarily as hole-transport materials in OLEDs), in nanolithography, and in amorphous drug formulations. [Hancock, B. C.; Zografi, G. "Characteristics and Significance of the Amorphous State in Pharmaceutical Systems", J. Pharm. Sci. 1997, 86, 1-12. Shirota, Y. "Organic materials for electronic and optoelectronic devices", J. Mater. Chem. 2000, 10, 1-25. Yu, L. "Amorphous pharmaceutical solids: preparation, characterization and stabilization", Adv. Drug Deliv. Rev. 2001, 48, 27-42. Shirota, Y. "Photo- and electroactive amorphous molecular materials—molecular design, syntheses, reactions, properties, and applications", J. Mater. Chem. 2005, 15, 75-93. Dai, J.; Chang, S. W.; Hamad, A.; Yang, D.; Felix, N.; Ober, C. K. "Molecular Glass Resists for High-Resolution Patterning", Chem. Mater. 2006, 18, 3404-3411. Gražulevičius, J. V. "Charge-transporting polymers and molecular glasses for optoelectronic applications", Polym. Adv. Technol. 2006, 17, 694-696.]

The two most commonly occurring problems with molecular glasses are: (1) limited accessibility of the glassy phase, as most compounds only form glasses when cooled extremely rapidly or through other special processing, and (2) their tendency to crystallize upon heating or standing for extended periods of time, due to the metastability of the glassy state and the higher mobility of small molecules relative to polymers. [Ediger, M. D.; Angell, C. A.; Nagel, S. R. "Supercooled Liquids and Glasses", J. Phys. Chem. 1996, 100, 13200-13212.] Thus, the current challenge with molecular glasses is to design compounds capable of readily accessing the glassy state, even upon slow cooling, and that do not re-crystallize upon heating or prolonged standing. While several examples of such glasses have been reported, and some guidelines for molecular glass design have been established (for example, most glass-forming small molecules possess globular and irregular shapes to prevent efficient packing, and typically avoid strong and directional intermolecular interactions), the design of a glass-forming compound for a specific purpose requires some measure of trial-and-error screening of molecular structures, because the molecular structure must be tailor-made to fit the structural requirements for glass formation, often involving a multi-step synthesis where the molecular structure as a whole serves to disfavour crystallization. [Ishow, E.; Bellaïche, C.; Bouteiller, L.; Nakatani, K.; Delaire, J. A. "Versatile Synthesis of Small NLO-Active Molecules Forming Amorphous Materials with Spontaneous Second-Order NLO Response", J. Am. Chem. Soc. 2003, 125, 15744-15745. Tanino, T.; Yoshikawa, S.; Ujike, T.; Nagahama, D.; Moriwaki, K.; Takahashi, T.; Kotani, Y.; Nakano, H.; Shirota, Y. "Creation of azobenzene-based photochromic amorphous molecular materials-synthesis, glass-forming properties and photochromic response", J. Mater. Chem. 2007, 17, 4953-4963. Nagahama, D.; Nakano, H.; Shirota, Y. "Synthesis and Photochromic Response of a New Photochromic Amorphous Molecular Material Based on Spirooxazine", J. Photopolym. Sci. Technol., 2008, 21, 755-757.] Therefore, there currently exists no general glass-inducing moiety that can be readily introduced by a simple synthetic procedure on a given compound to promote the formation of glassy phases.

Previously, we have developed a series of glasses based on mexylaminotriazines that show all the desirable properties for glass formation; in this case, however, it has been shown that hydrogen bonding contributes to promote glass formation through the formation of supramolecular aggregates that pack poorly. The hydrogen bonding provides an additional energetic barrier to reorganization of molecules in the solid state, which eventually leads to crystallization. [Wuest, J. D.; Lebel, O. "Anarchy in the solid state: structural dependence on glass-forming ability in triazine-based molecular glasses", Tetrahedron, 2009, 65, 7393-7402. Wang, R.; Pellerin, C.; Lebel, O. "Role of Hydrogen Bonding in the Formation of Glasses by Small Molecules: A Triazine Case Study", J. Mater. Chem., 2009, 19, 2747-2753. Plante, A.; Mauran, D.; Carvalho, S. P.; Pagé, J. Y. S. D.; Pellerin, C.; Lebel, O. "Tg and Rheological Properties of Triazine-Based Molecular Glasses: Incriminating Evidence Against Hydrogen Bonds", J. Phys. Chem. B, 2009, 113, 14884-14891.]

We have previously demonstrated that compounds that readily crystallize, such as tetraphehylporphyrin (TPP), can be made to form glasses by functionalization with mexylaminotriazine units. However, in this example, it was necessary to build the glass-inducing moieties on the TPP core in several steps and a global yield close to 50%. [Meunier, A.; Lebel, O. "A Glass Forming Module for Organic Molecules: Making Tetraphenylporphyrin Lose its Crystallinity", Org. Lett., 2010, 12, 1896-1899.]

Therefore, novel molecular glasses that can be grafted covalently on a given core compound to induce the formation of glassy phases in one facile, high-yielding step is highly desirable, because it will (1) reduce the amount of screening necessary to identify structures which lead to a high propensity of forming glasses and a high longevity of the glassy state, and (2) enable to access molecular glasses with various properties for various applications in a rapid and efficient fashion starting from a few common precursor "snap-on" glasses that can be conveniently synthesized.

BRIEF SUMMARY

We have discovered molecular glasses that are capable of readily forming glassy phases (molecular glasses) and recrystallizes extremely slowly over time, which can be bonded covalently in one step to a compound of interest to impart to the latter its glass-forming properties.

Accordingly in one aspect, there is provided a compound having Formula I:

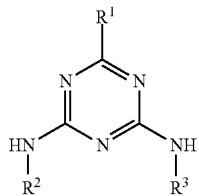

or a salt thereof
wherein:
R¹ is
1) H,
2) halogen,
3) NO₂,
4) CN,
5) N₃,
6) C₁-C₆ alkyl,
7) C₃-C₇ cycloalkyl,
8) haloalkyl,
9) (CF₂)$_n$CF₃, where n is an integer of 0 to 20,
10) C₂-C₆ alkenyl,
11) C₂-C₄ alkynyl,
12) aryl,
13) heteroaryl,
14) heterocyclyl,
15) OR⁴,
16) OSO₂R⁴,
17) N(R⁴)₂,
18) SR⁴,
19) SSR⁴,
20) COR⁴,
21) CO₂R⁴,
22) CON(R⁴)₂,
23) CH(R⁶)₂,
24) SOR⁴,
25) SO₂R⁴,
26) SO₃R⁴,
27) SON(R⁴)₂,
28) SO₂N(R⁴)₂,
29) P(R⁴)₂,
30) P(OR⁴)₂,
31) P(N(R⁴)₂)₂,
32) P(O)(R⁴)₂,
33) P(O)(OR⁴)₂,
34) P(O)(NR⁴₂)₂,
35) B(R⁴)₂,
36) B(OR⁴)₂,
37) Si(R⁴)₃, or
38) Sn(R⁴)₃;
R² is
1) C₁-C₆ alkyl,
2) C₃-C₇ cycloalkyl,
3) aryl, or
4) heteroaryl,
wherein the cycloalkyl, the aryl and the heteroaryl are substituted with two or three R¹ substituents;
R³ is
1) R$^A$,
2) C₁-C₆ alkyl-R$^A$,
3) aryl-R$^A$,
4) heteroaryl-R$^A$,
5) aryl-R²⁰—R$^B$, or
6) heteroaryl-R²⁰—R$^B$;
R⁴ is
1) H,
2) C₁-C₆ alkyl,
3) C₃-C₇ cycloalkyl,
4) haloalkyl,
5) (CF₂)$_n$CF₃, where n is an integer of 0 to 20,
6) C₂-C₆ alkenyl,
7) C₂-C₄ alkynyl,
8) aryl,
9) heteroaryl, or
10) heterocyclyl;
R⁶ is
1) NO₂,
2) CN,
3) C(O)R⁴,
4) CO₂R⁴,
5) C(O)N(R⁴)₂,
6) P(O)(OR⁴)₂,
7) P(O)(N(R⁴)₂)₂,
8) SO₂R⁴, or
9) SO₂N(R⁴)₂;
R²⁰ is
1) O,
2) NH,
3) S,
4) C(O),
5) C(O)O, or
6) CONH;
R$^A$ is
1) halogen,
2) OSO₂R⁴,
3) OH,
4) OCH=CHR⁴,
5) OCH₂CH=CH₂,
6) OCHC=CR⁴,
7) N(R⁴)₂,
8) SH,
9) P(R⁴)₂,
10) CH=CHR⁴,
11) CH=CHC(O)OR⁴,
12) CCR⁴,
13) OCH₂C=CH,
14) CN,
15) N₃,
16) CHO,
17) C(O)R⁴,
18) CO₂R⁴,
19) B(OR⁴)₂,
20) Si(R⁴)₃,
21) Sn(R⁴)₃.
22) CH₂Br,
23) CH₂OH,
24) OCH₂CH(OH)CH₂OH,
25)

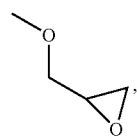

26) NCO, or
27) NCS; and
$R^B$ is
1) $C_1$-$C_6$ alkyl-$R^A$,
2) aryl-$R^A$, or
3) heteroaryl-$R^A$.

Accordingly in another aspect, there is provided a precursor compound of the following Formula 2:

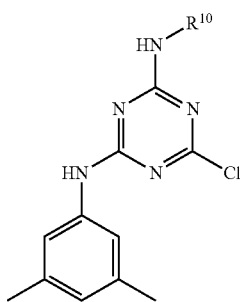

or a salt thereof,
wherein $R^{10}$ is $C_1$-$C_4$ alkyl.

Accordingly, in another aspect there is provided a process for the preparation of a compound of Formula I, the process comprising:
a) heating an intermediate compound of

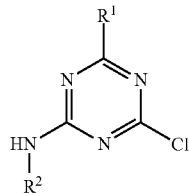

with a $R^3NH_2$ in the presence of a base so as to produce a compound of Formula I, wherein $R^1$, $R^2$ and $R^3$ are as defined above.

Accordingly, in another aspect there is provided a process for the preparation of a compound of Formula I, the process comprising:
a) reacting an intermediate compound

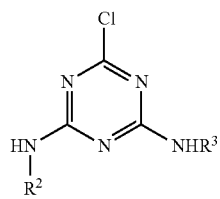

with $R^1NH_2$ in the presence of a catalyst so as to produce a compound of Formula I,

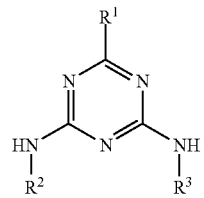

wherein $R^1$, $R^2$ and $R^3$ are as defined above.

Accordingly, in another aspect there is provided a process for the preparation of a compound of Formula I, the process comprising:
a) heating

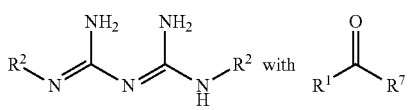

so as to produce a compound of Formula I,

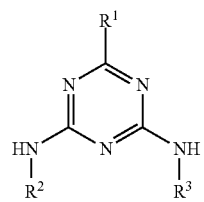

wherein $R^1$, $R^2$ and $R^3$ are as defined above, and $R^7$ is selected from the group consisting of: F, Cl, Br, $OR^4$, $SR^4$, $OCOR^4$, $OCO_2R^4$, $OCONR^4_2$, $SCOR^4$, $SCO_2R^4$, $SCONR^4_2$, $OSO_2R^4$, $OSO_3R^4$, $OPO(OR^4)_2$, 1-hydroxybenzotriazolyl (OBt), 1-hydroxy-7-azobenzotriazolyl (OAt), 1-hydroxy-6-chlorobenzotriazolyl (OCt), ethyl 2-cyano-2-hydroxyiminoacetate, hydroxysuccinimidyl (OSu), and hydroxyphthalimidyl (OPhth), wherein $R^4$ is as defined above.

Accordingly, in another aspect there is provided a process for the preparation of an intermediate of Formula 2:

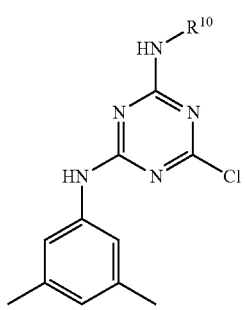

the process comprising:

a) reacting

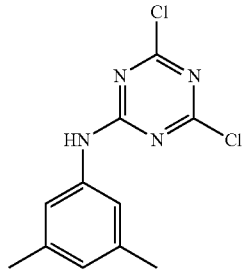 [SMILES: Cc1cc(C)cc(Nc2nc(Cl)nc(Cl)n2)c1]

with $R^{10}$—$NH_2$ at room temperature in the presence of a base so as to produce the intermediate, wherein $R^{10}$ is $C_1$-$C_4$ alkyl, for example Me, Et or iPr.

Accordingly, in another aspect there is provided a process for the preparation of a compound of the following Formula:

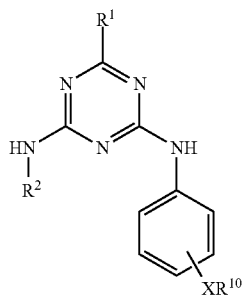

the process comprising:

a) reacting

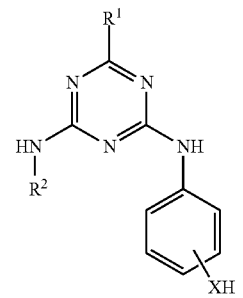

with $R^5$—$R^{13}$ in the presence of a base, the "—" between the $R^5$ and the $R^{13}$ indicating a covalent bond, wherein

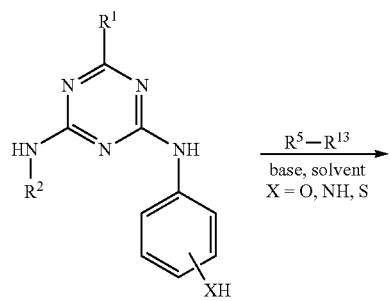

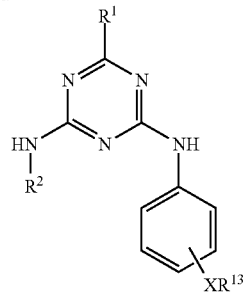

wherein $R^1$, $R^2$, $R^5$ and $R^{13}$ are as defined herein.

Accordingly, in another aspect there is provided a process for the preparation of a compound of Formula I, the process comprising:

a) heating

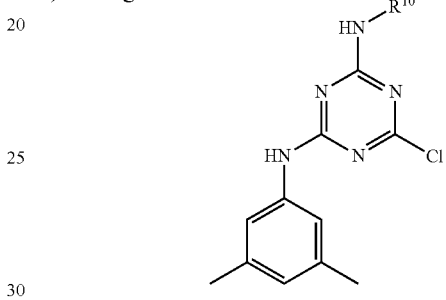

with $R^3NH_2$ so as to produce a compound of Formula I, wherein $R^3$ is as defined above, and $R^{10}$ is $C_1$-$C_4$ alkyl, for example Me, Et or iPr.

Accordingly, in another aspect there is provided a process for the preparation of a compound of the following Formula:

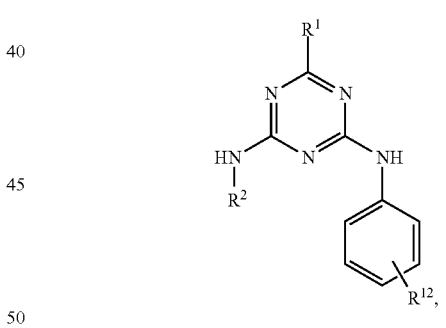

the process comprising:

a) reacting

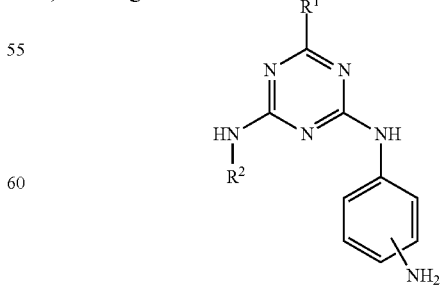

with i) $R^{11}NO_2$ or $MNO_2$ and ii) $MR^{12}$, wherein $R^1$ and $R^2$ are as defined above, and $R^{11}$ is $C_1$-$C_6$ alkyl and $R^{12}$ is an aryl or heteroaryl substituted with one or more substituents selected from the group consisting of: NH$_2$, OH, N$_3$, CN, formaldoxime (CH$_2$NOH), a thiocarboxylate (R$^3$C(O)S), thiolate (R$^3$S), dithiocarbamate (R$^3$NC(S)S) and xanthate (R$^3$OC(S)S salt, in which R$^3$ is as defined above; and M is a metal.

Accordingly, in another aspect there is provided use of a compound of Formula I

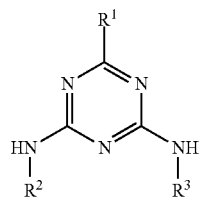

I or a salt thereof, as described above, as an amorphous material.

Accordingly, in another aspect there is provided a method of forming stable glassy phases in compounds otherwise incapable of doing so spontaneously during slow cooling from a melt at a rate equal to or lower than 10° C./min., the method comprising reacting a compound having Formula I.

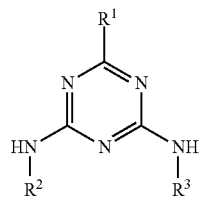

I as described above, with a compound of interest incapable of glass formation, the reaction taking place between the R$^A$ substituent and an R$^C$ substituent on the compound of interest so as to form a covalent bond therebetween, wherein the R$^C$ is selected from the group consisting of:
1) halogen,
2) OSO$_2$R$^4$,
3) OH,
4) OCH=CHR$^4$,
5) OCH$_2$CH=CH$_2$,
6) OCHC=CR$^4$
7) N(R$^4$)$_2$,
8) SH,
9) P(R$^4$)$_2$,
10) CH=CHR$^4$,
11) CH=CHC(O)OR$^4$,
12) CCR$^4$,
13) OCH$_2$C=CH,
14) CN,
15) N$_3$,
16) CHO,
17) C(O)R$^4$,
18) CO$_2$R$^4$,
19) B(OR$^4$)$_2$,
20) Si(R$^4$)$_3$,
21) Sn(R$^4$)$_3$.
22) CH$_2$Br,
23) CH$_2$OH,
24) OCH$_2$CH(OH)CH$_2$OH,
25)

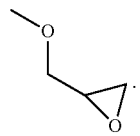

26) NCO, or
27) NCS.

DETAILED DESCRIPTION

Definitions

Unless otherwise specified, the following definitions apply:

The singular forms "a", "an" and "the" include corresponding plural references unless the context clearly dictates otherwise.

As used herein, the term "comprising" is intended to mean that the list of elements following the word "comprising" are required or mandatory but that other elements are optional and may or may not be present.

As used herein, the term "consisting of" is intended to mean including and limited to whatever follows the phrase "consisting of". Thus the phrase "consisting of" indicates that the listed elements are required or mandatory and that no other elements may be present.

As used herein, the term "alkyl" is intended to include both branched and straight chain saturated aliphatic hydrocarbon groups having the specified number of carbon atoms, for example, C$_1$-C$_6$ as in C$_1$-C$_6$ alkyl is defined as including groups having 1, 2, 3, 4, 5 or 6 carbons in a linear or branched arrangement, and C$_1$-C$_4$ as in C$_1$-C$_4$ alklyl is defined as including groups having 1, 2, 3, or 4 carbons in a linear or branched arrangement. Examples of C$_1$-C$_6$ alkyl as defined above include, but are not limited to, methyl, ethyl, n-propyl, i-propyl, n-butyl, t-butyl, i-butyl, pentyl and hexyl.

As used herein, the term, "alkenyl" is intended to mean unsaturated straight or branched chain hydrocarbon groups having the specified number of carbon atoms therein, and in which at least two of the carbon atoms are bonded to each other by a double bond, and having either E or Z regeochemistry and combinations thereof. For example, C$_2$-C$_6$ as in C$_2$-C$_6$ alkenyl is defined as including groups having 2, 3, 4, 5, or 6 carbons in a linear or branched arrangement, at least two of the carbon atoms being bonded together by a double bond. Examples of C$_2$-C$_6$ alkenyl include ethenyl (vinyl), 1-propenyl, 2-propenyl, 1-butenyl and the like.

As used herein, the term "alkynyl" is intended to mean unsaturated, straight chain hydrocarbon groups having the specified number of carbon atoms therein and in which at least two carbon atoms are bonded together by a triple bond. For example C$_2$-C$_4$ as in C$_2$-C$_4$ alkynyl is defined as including groups having 2, 3, or 4 carbon atoms in a chain, at least two of the carbon atoms being bonded together by a triple bond. Examples of such alkynyls include ethynyl, 1-propynyl, 2-propynyl and the like.

As used herein, the term "cycloalkyl" is intended to mean a monocyclic saturated aliphatic hydrocarbon group having the specified number of carbon atoms therein, for example, C$_3$-C$_7$ as in C$_3$-C$_7$ cycloalkyl is defined as including groups having 3, 4, 5, 6, or 7 carbons in a monocyclic arrangement.

Examples of $C_3$-$C_7$ cycloalkyl as defined above include, but are not limited to, cyclopropyl, cyclobutyl, cyclopentyl, cyclohexyl and cycloheptyl.

As used herein, the term "halo" or "halogen" is intended to mean fluorine, chlorine, bromine and iodine.

As used herein, the term "haloalkyl" is intended to mean an alkyl as defined above, in which each hydrogen atom may be successively replaced by a halogen atom. Examples of haloalkyls include, but are not limited to, $CH_2F$, $CHF_2$ and $CF_3$.

As used herein the term "perfluoroalkyl" is intended to mean substituents of the following formula: $(CF_2)_nCF_3$, where n is an integer of 0 to 20.

As used herein, the term "aryl", either alone or in combination with another radical, means a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, 1-naphthyl, 2-naphthyl and tetrahydronaphthyl. The aryls may be connected to another group either at a suitable position on the cycloalkyl ring or the aromatic ring.

As used herein, the term "heteroaryl" is intended to mean a monocyclic or bicyclic ring system of up to ten atoms, wherein at least one ring is aromatic, and contains from 1 to 4 hetero atoms selected from the group consisting of O, N, and S. The heteroaryl substituent may be attached either via a ring carbon atom or one of the heteroatoms. Examples of heteroaryl groups include, but are not limited to thienyl, benzimidazolyl, benzo[b]thienyl, furyl, benzofuranyl, pyranyl, isobenzofuranyl, chromenyl, xanthenyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, napthyridinyl, quinoxalinyl, quinazolinyl, cinnolinyl, pteridinyl, isothiazolyl, isochromanyl, chromanyl, isoxazolyl, furazanyl, indolinyl, and isoindolinyl.

As used herein, the term "heterocycle", "heterocyclic" or "heterocyclyl" is intended to mean a 5, 6, or 7 membered non-aromatic ring system containing from 1 to 4 heteroatoms selected from the group consisting of O, N and S. Examples of heterocycles include, but are not limited to pyrrolidinyl, tetrahydrofuranyl, piperidyl, pyrrolinyl, piperazinyl, imidazolidinyl, morpholinyl, imidazolinyl, pyrazolidinyl, and pyrazolinyl, As used herein, the term "heteroatom" is intended to mean O, S or N.

As used herein, the term "metal" or "M" is intended to mean either alkali (Li, Na, K, Rb, Cs) or earth alkaline (Be, Mg, Ca, Sr, Ba) metals. Also included are transition metals (e.g. Ti, Cu, Ni, Co, Fe), main group metals (e.g. Al, In, Sn), lanthanides (e.g. Gd, Eu, Ce) or actinides (e.g. Th, U). Appropriate stoichiometry means that depending on the respective charge of the metal and counterion, the stoichiometry of both species may vary. For example, $Na_2CO_3$ vs. $MgCO_3$, NaOH vs. $Ca(OH)_2$ vs. $Al(OH)_3$.

As used herein, the term "mexyl" is intended to mean a 3,5-dimethylphenyl group having the following structure:

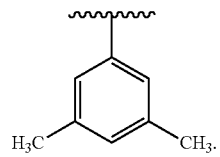

As used herein, the term "salt" is intended to mean both acid and base addition salts. As used herein, the term "acid addition salt" is intended to mean those salts which are formed with inorganic acids such as hydrochloric acid, hydrobromic acid, sulfuric acid, nitric acid, phosphoric acid and the like. As used herein, the term "base addition salt" is intended to mean those salts prepared from addition of an inorganic base to the free acid. Salts derived from inorganic bases include, but are not limited to, the sodium, potassium, lithium, ammonium, calcium, magnesium, iron, zinc, copper, manganese, aluminum salts and the like.

If the substituents themselves are incompatible with the synthetic methods of the present invention, the substituent may be protected with a suitable protecting group (PG) that is stable to the reaction conditions used in these methods. The protecting group may be removed at a suitable point in the reaction sequence of the method to provide a desired intermediate or target compound. Suitable protecting groups and the methods for protecting and de-protecting different substituents using such suitable protecting groups are well known to those skilled in the art; examples of which may be found in T. Greene and P. Wuts, Protecting Groups in Chemical Synthesis (3.sup.rd ed.), John Wiley & Sons, NY (1999). In some instances, a substituent may be specifically selected to be reactive under the reaction conditions used in the methods described herein. Under these circumstances, the reaction conditions convert the selected substituent into another substituent that is either useful in an intermediate compound in the methods described herein or is a desired substituent in a target compound.

I. Molecular Glasses

We have discovered derivatized 1,3,5 triazine compounds which are capable of readily forming glassy phases and which recrystallize extremely slowly over time. These compounds be bonded covalently in one step to a compound of interest to impart to the latter its glass-forming properties. The compounds of interest include, but are not limited to, a dye, a fluorophore, a semiconductor, a ligand for transition metals, and a calixarene derivative. These compounds of interest contain a functional group strategically designed to react with a reactive group on the molecular glasses as described herein to form a covalent bond.

Core:

Broadly speaking, the present discovery concerns compounds as represented by Formula I:

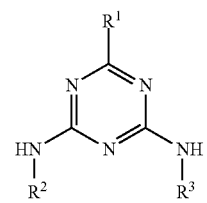

or a salt thereof, wherein $R^1$, $R^2$ and $R^3$ are as defined hereinabove and hereinafter.

One subset of compounds of Formula I include compounds of Formula I.2:

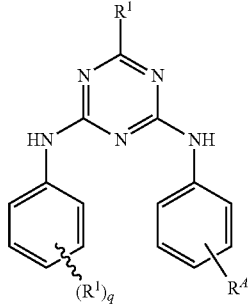

I.2 wherein q is an integer of 2 or 3, and $R^1$ and $R^4$ are as defined hereinabove and hereinafter. The wavy line is intended to indicate that the $R^1$ substituents can be covalently bonded to the phenyl ring, when q is 2, in the 3 and 5 positions; or, when q is 3, in the 3, 4, and 5 positions or the 2, 3, and 5 positions.

Specific examples of compounds of Formula I.2 include compounds of Formula I.2 through I.12:

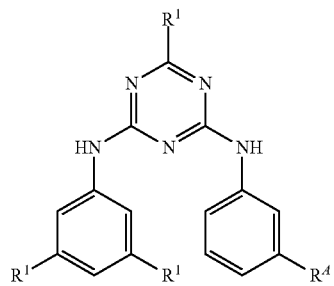

I.3

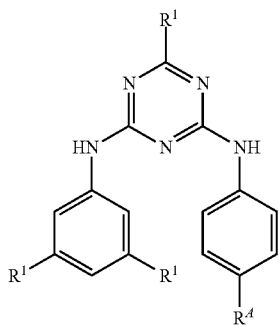

I.4

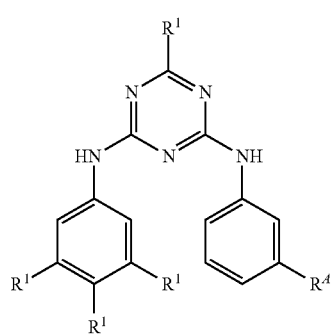

I.5

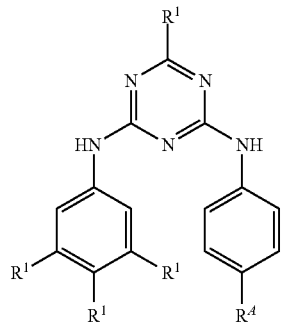

I.6

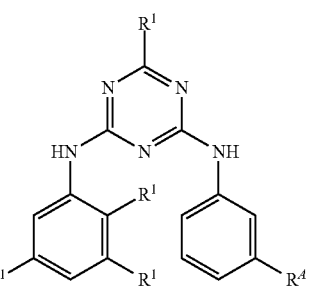

I.7

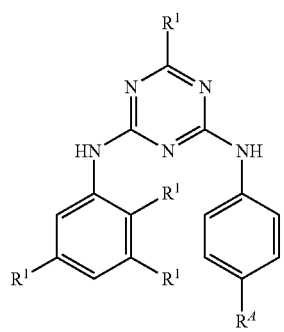

I.8

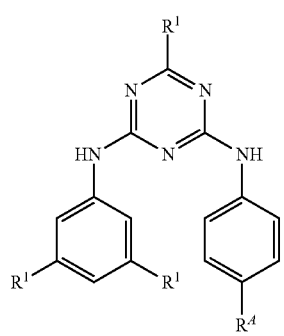

I.9

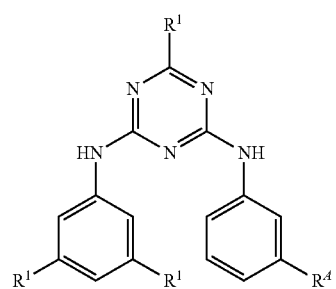

I.10

-continued

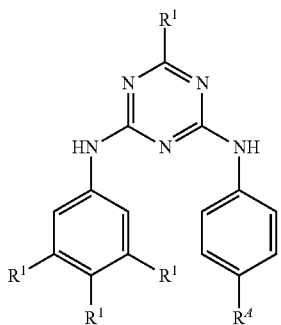
I.11

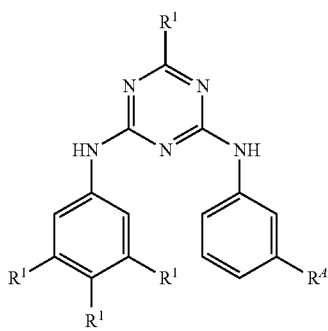
I.12 wherein $R^1$ and $R^4$ are as defined hereinabove and hereinbelow.

An alternative subset of compounds of Formula I includes compounds of Formula I.13,

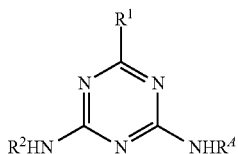
I.13 wherein $R^1$, $R^2$ and $R^4$ are as defined hereinabove and hereinbelow.

One example of compounds of Formula I.13 include compounds of Formula I.14:

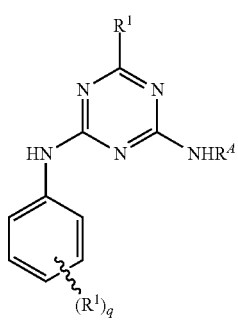
I.14 wherein q is an integer of 2 or 3, and $R^1$, and $R^4$ are as defined herein. The wavy line is intended to indicate that the $R^1$ substituents can be covalently bonded to the phenyl ring, when q is 2, in the 3 and 5 positions; or, when q is 3, in the 3, 4, and 5 positions or the 2, 3, and 5 positions.

Specific examples of compounds of Formula I.14 include compounds of Formula I.17 and I.18:

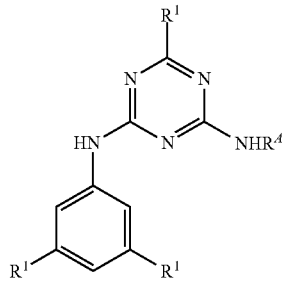
I.15

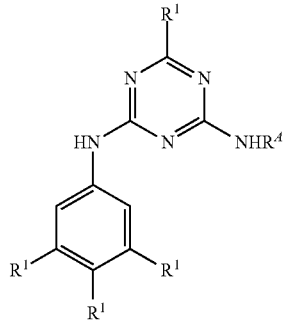
I.16

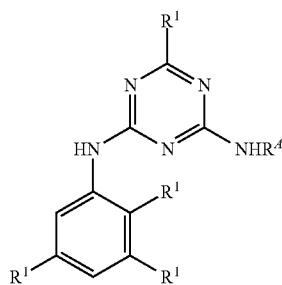
I.16 wherein $R^1$ and $R^4$ are as defined hereinabove and hereinbelow.

An alternative subset of compounds of Formula I includes compounds of Formula I.17,

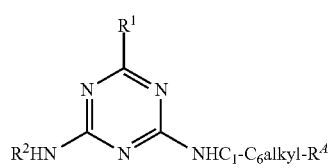
I.17 wherein $R^1$, $R^2$ and $R^4$ are as defined hereinabove and hereinbelow.

One example of compounds of Formula I.17 include compounds of Formula I.18:

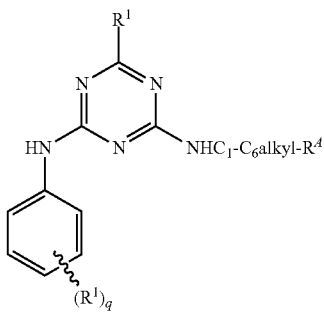

wherein q is an integer of 2 or 3, and $R^1$, $R^4$ are as defined herein. The wavy line is intended to indicate that the $R^1$ substituents can be covalently bonded to the phenyl ring, when q is 2, in the 3 and 5 positions; or, when q is 3, in the 3, 4, and 5 positions or the 2, 3, and 5 positions.

Specific examples of compounds of Formula I.18 include compounds of Formula I.19, I.20 and I.21:

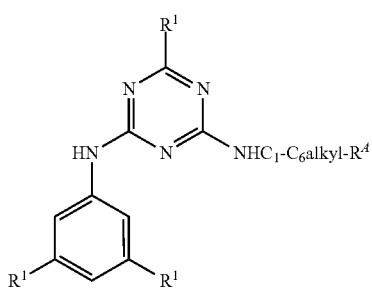

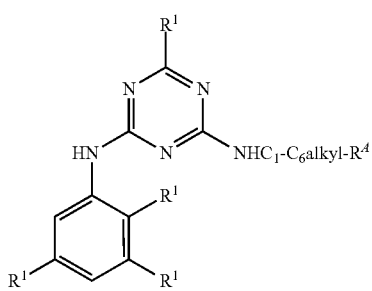

wherein $R^1$ and $R^4$ are as defined hereinabove and hereinbelow.

$R^1$:

In one subset of compounds, $R^1$ is
1) H,
2) halogen,
3) $NO_2$,
4) CN,
5) $N_3$,
6) $C_1$-$C_6$ alkyl,
7) $C_3$-$C_7$ cycloalkyl,
8) haloalkyl,
9) $(CF_2)_nCF_3$, where n is an integer of 0 to 20,
10) $C_2$-$C_6$ alkenyl,
11) $C_2$-$C_4$ alkynyl,
12) aryl,
13) heteroaryl,
14) heterocyclyl,
15) $OR^4$,
16) $OSO_2R^4$,
17) $N(R^4)_2$,
18) $SR^4$,
19) $SSR^4$,
20) $COR^4$,
21) $CO_2R^4$,
22) $CON(R^4)_2$,
23) $CH(R^6)_2$,
24) $SOR^4$,
25) $SO_2R^4$,
26) $SO_3R^4$,
27) $SON(R^4)_2$,
28) $SO_2N(R^4)_2$,
29) $P(R^4)_2$,
30) $P(OR^4)_2$,
31) $P(N(R^4)_2)_2$,
32) $P(O)(R^4)_2$,
33) $P(O)(OR^4)_2$,
34) $P(O)(NR^4{}_2)_2$,
35) $B(R^4)_2$,
36) $B(OR^4)_2$,
37) $Si(R^4)_3$, or
38) $Sn(R^4)_3$.

In one example, $R^1$ is
1) $OR^4$,
2) $OSO_2R^4$,
3) $N(R^4)_2$,
4) $SR^4$,
5) $COR^4$,
6) $CO_2R^4$, or
7) $CON(R^4)_2$.

In one example, $R^1$ is $N(R^4)_2$. In one example, $R^1$ is $NHCH_3$.

$R^2$:

In one subset, $R^2$ is
1) $C_1$-$C_6$ alkyl,
2) $C_3$-$C_7$ cycloalkyl,
3) aryl or
4) heteroaryl,
wherein the cycloalkyl, the aryl and the heteroaryl are substituted with two or three $R^1$ substituents.

In one example, $R^2$ is phenyl substituted with two or three $R^1$ substituents.

Examples of $R^2$ are selected from the group consisting of:

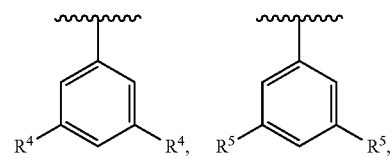

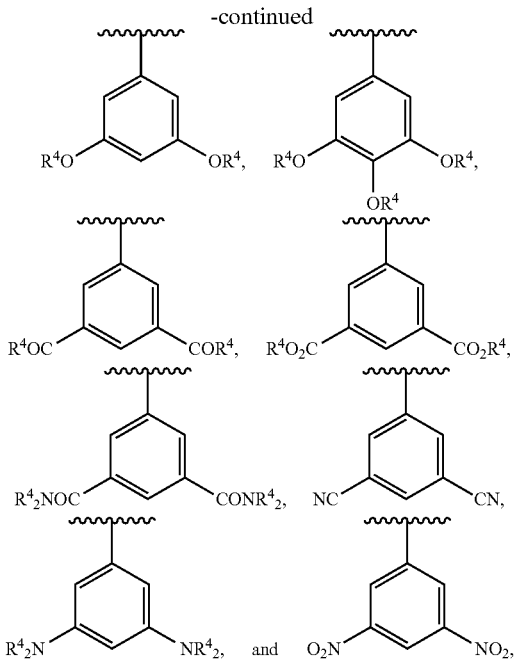

wherein $R^4$ and $R^5$ are as defined herein.

In one example, $R^2$ is phenyl substituted with two $R^1$ substituents.

Specific examples of $R^2$ are selected from the group consisting of:

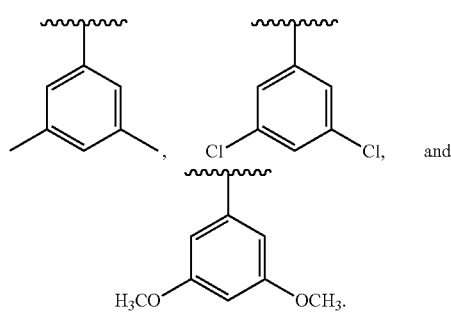

In one example, $R^2$ is phenyl substituted with three $R^1$ substituents.

In one example, $R^2$ is

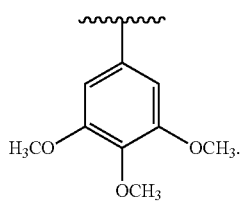

$R^3$:

In one subset, $R^3$ is
1) $R^A$,
2) $C_1C_6$ alkyl-$R^A$
3) aryl-$R^A$
4) heteroaryl-$R^A$
5) aryl-$R^{20}$—$R^B$, or
6) heteroaryl-$R^{20}$—$R^B$;

In one example, $R^3$ is phenyl-$R^A$.

Examples of $R^3$ are selected from the group consisting of:

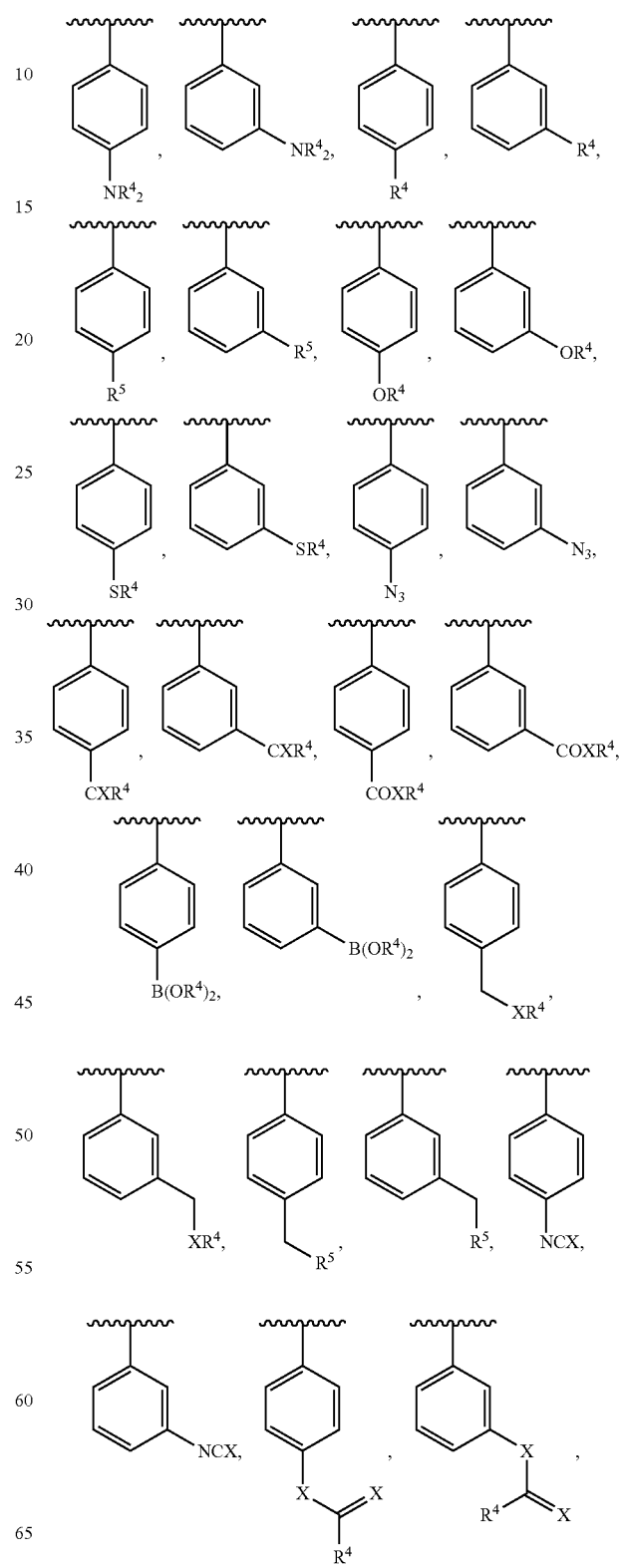

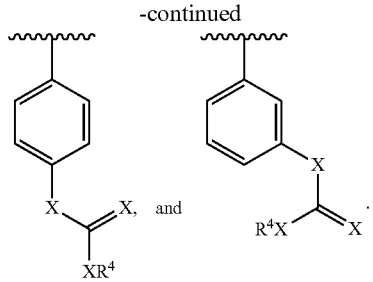

$R^4$ and $R^5$ are as defined herein, and X is $NR^4$, O or S.

Specific examples of $R^3$ are selected from the group consisting of:

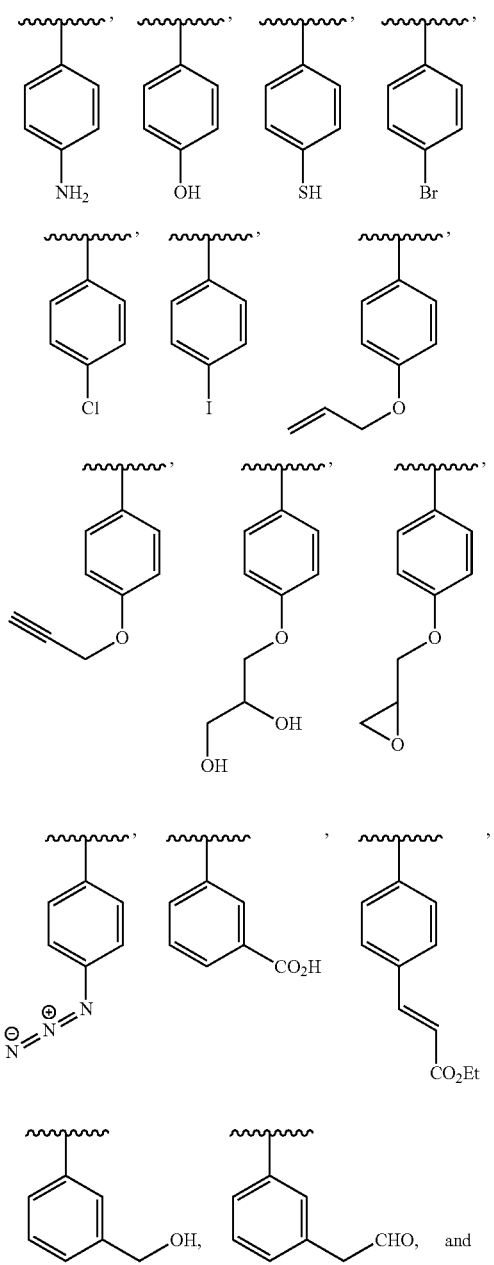

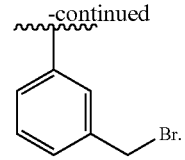

In an alternative subset, $R^3$ is $C_1$-$C_6$ alkyl-$R^4$.

Examples of $R^3$ are selected from the group consisting of:

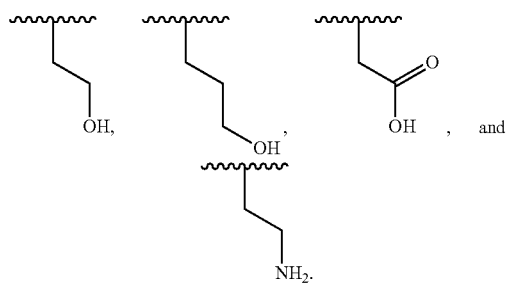

$R^4$:

In one subset, $R^4$ is
1) H,
2) $C_1$-$C_6$ alkyl,
3) $C_3$-$C_7$ cycloalkyl,
4) haloalkyl,
5) $(CF_2)_n CF_3$, where n is an integer of 0 to 20,
6) $C_2$-$C_6$ alkenyl,
7) $C_2$-$C_4$ alkynyl,
8) aryl,
9) heteroaryl, or
10) heterocyclyl.

$R^5$:

In one subset, $R^5$ is
1) halogen or
2) $OSO_2R^4$.

Examples of $R^5$ are selected from the group consisting of: F, Cl, Br, I, and $OSO_2R^4$.

$R^6$:

In one subset, $R^6$ is
1) $NO_2$,
2) CN,
3) $C(O)R^4$,
4) $CO_2R^4$,
5) $C(O)N(R^4)_2$,
6) $P(O)(OR^4)_2$,
7) $P(O)(N(R^4)_2)_2$,
8) $SO_2R^4$, or
9) $SO_2N(R^4)_2$.

Examples of $R^6$ are selected from the group consisting of: $NO_2$, CN, $COR^4$, $CO_2R^4$, $CONR^4_2$, $PO(OR^4)_2$, $PO(NR^4_2)_2$, $SO_2R^4$, and $SO_2NR^4_2$.

$R^{10}$:

In one subset, $R^{10}$ is $C_1$-$C_4$ alkyl. Examples of $R^{10}$ include Me, Et or iPr.

$R^{13}$:

In one subset, $R^{13}$ is an alkyl or acyl group containing one or several alkene, alkyne, halogen, sulfonate, alcohol, thiol, amine, azide, epoxy, carbonyl, or carboxyl groups.

$R^{20}$:

In one subset, $R^{20}$ is
1) O,
2) NH,

3) S,
4) C(O),
5) C(O)O, or
6) CONH.

$R^A$:
In one subset, $R^A$ is
1) halogen,
2) $OSO_2R^4$,
3) OH,
4) $OCH=CHR^4$,
5) $OCH_2CH=CH_2$,
6) $OCHC=CR^4$
7) $N(R^4)_2$,
8) SH,
9) $P(R^4)_2$,
10) $CH=CHR^4$,
11) $CH=CHC(O)OR^4$,
12) $CCR^4$,
13) $OCH_2C=CH$,
14) CN,
15) $N_3$,
16) CHO,
17) $C(O)R^4$,
18) $CO_2R^4$,
19) $B(OR^4)_2$,
20) $Si(R^4)_3$,
21) $Sn(R^4)_3$.
22) $CH_2Br$,
23) $CH_2OH$,
24) $OCH_2CH(OH)CH_2OH$, or
25)

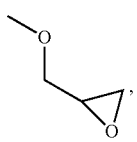

26) NCO, or
27) NCS.

Examples of $R^A$ are selected from the group consisting of:
$NH_2$, OH, SH, Br, Cl, I, CHO, $CO_2H$, $N_3$, $CH_2Br$,

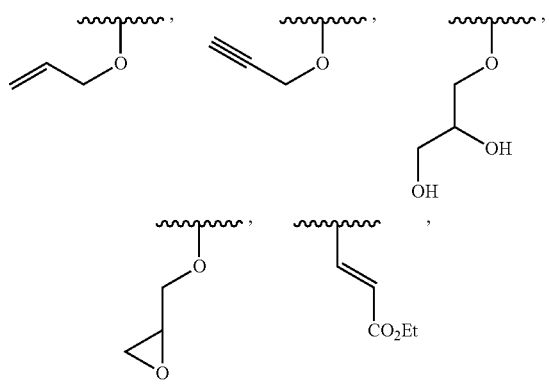

and
$R^B$:
In one subset, $R^B$ is
1) $C_1$-$C_6$ alkyl-$R^A$,
2) aryl-$R^A$, or
3) heteroaryl-$R^A$.

SYNTHETIC METHODOLOGY

I: Synthesis of Formula I Compounds

Glass forming compounds of the Formula I, in which $R^1$, $R^2$ and $R^3$ are as defined hereinabove and hereinbelow, may be synthesized according to Schemes 1 through 3 below.

Scheme 1

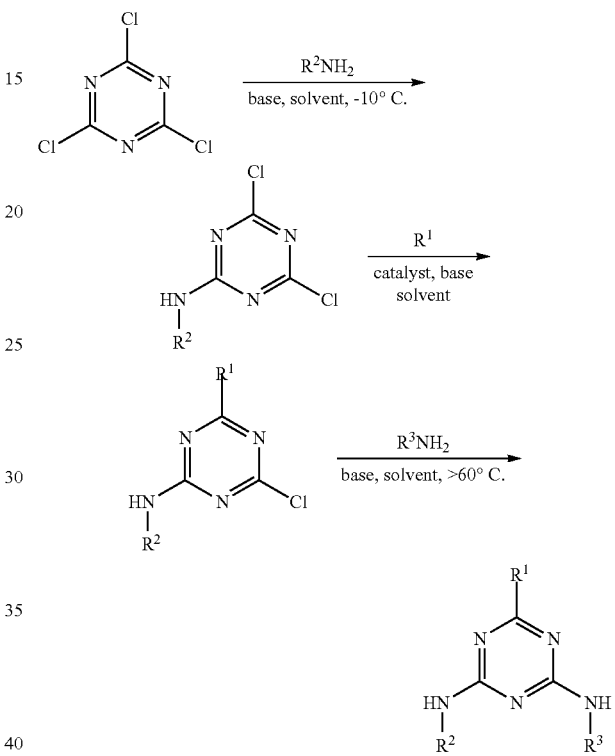

Scheme 2

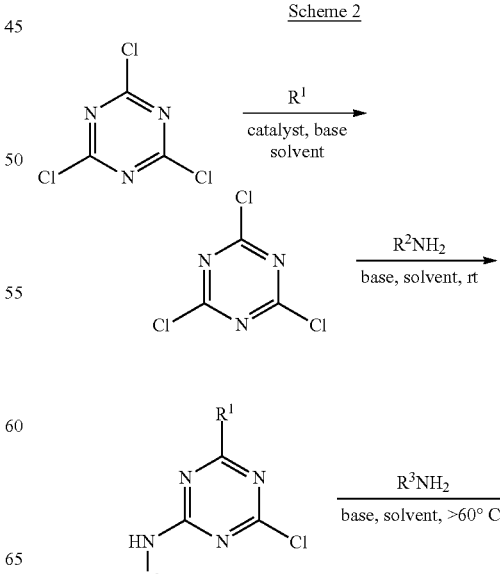

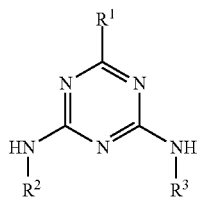

Scheme 3

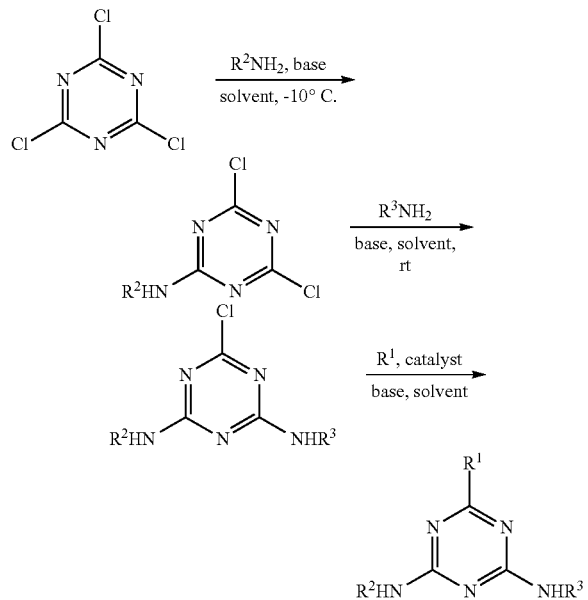

In accordance with Schemes 1-3, cyanuric chloride is successively reacted with three different nucleophiles at various temperatures to give the trisubstituted triazine having Formula I. The order of substitution is irrelevant and substituents can be introduced in any order. In some cases, however, the synthetic methodology dictates the order of substitution. Two of these nucleophiles are primary amines bearing the $R^2$ and $R^3$ substituents, while the other nucleophile, $R^1$, can be a primary or secondary amine, an alkyl, aryl or heteroaryl organometallic reagent, an enolate or a similar species, an alcohol (or phenol), an alkoxide, a thiol, a thiolate, a thiocarbonyl derivative, a cyanide, an azide, a phosphine, a phosphite. In each step, a non-nucleophilic base may be added to neutralize acid generated during the reaction, and the reaction is performed in an appropriate solvent. Examples of base include $MnCO_3$, $MnPO_4$, $NR^4_3$, or $MH_n$ in which n is or 2 and depends on the oxidation state of the metal, for example $Na_2CO_3$, $CaCO_3$, NaH, and $CaH_2$. For the addition of $R^1$, an appropriate organic, organometallic or inorganic catalyst may be used.

The substituents for Schemes 1-3 are as follows:
$R^1$, $R^2$, $R^3$, $R^4$, $R^5$ and $R^6$ are as defined herein; and M is any metal, in an appropriate stoichiometry as to balance charges.

Examples of substituents in Schemes 1-3 are as follows:
$R^1$ is NHMe, NHEt NH$^i$Pr, OMe, OEt or O$^i$Pr,
$R^2$ is 3,5-dimethylphenyl (mexyl), 3,5-dichlorophenyl, 3,5-dimethoxyphenyl, 3,4,5-trimethoxyphenyl, or 3,5-bis(trifluoromethyl); and $R^3$ is 4-aminophenyl, 4-hydroxyphenyl, 4-chlorophenyl, 4-bromophenyl, 4-iodophenyl, 4-vinylphenyl, 4-ethynylphenyl, 4-carboxyphenyl, 4-bromomethylphenyl, 3-aminophenyl, 3-hydroxyphenyl, 3-chlorophenyl, 3-bromophenyl, 3-iodophenyl, 3-vinylphenyl, 3-ethynylphenyl, 3-carboxyphenyl, or 3-bromomethylphenyl.

Examples of the base in Schemes 1-3 are $Na_2CO_3$, $K_2CO_3$, triethylamine or N,N-diisopropylethylamine.

Examples of solvents include acetone or THF for amine additions, and MeOH, EtOH or $^i$PrOH for alkoxide additions.

Alternatively, the compounds of Formula I may be synthesized according to Scheme 4 below.

Scheme 4

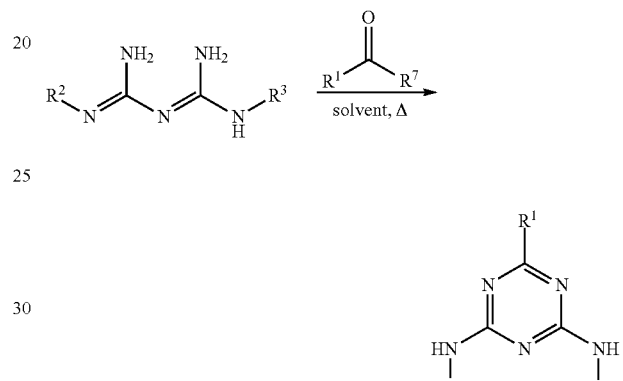

In accordance with Scheme 4, a disubstituted biguanide is condensed with an activated carboxylic acid derivative in an appropriate solvent. A coupling reagent may be used with $R^7$=OH. Examples of coupling reagents include $ClCO_2R^4$, $ClSO_2R^4$, $R^4N$=C=$NR^4$, $R^8C(NR^4_2)X^2$, $R^8P(NR^4)_3X^2$, $X^3R^9$, where $X^2$ is $BF_4$, $PF_6$, or $SbF_6$; $X^3$ is F, Cl or $CF_3SO_3$ and $R^9$ is an aromatic ring system or heteroatom-containing aromatic ring system with electron-withdrawing substituents.

The substituents for Scheme 4 are as follows:
$R^1$, $R^2$, $R^3$, $R^4$, $R^5$ and $R^6$ are as defined herein; and M is any metal, in an appropriate stoichiometry as to balance charges.

$R^7$ substituent examples include F, Cl, Br, $OR^4$, $SR^4$, $OCOR^4$, $OCO_2R^4$, $OCONR^4_2$, $SCOR^4$, $SCO_2R^4$, $SCONR^4_2$, $OSO_2R^4$, $OSO_3R^4$, $OPO(OR^4)_2$, 1-hydroxybenzotriazolyl (OBt), 1-hydroxy-7-azobenzotriazolyl (OAt), 1-hydroxy-6-chlorobenzotriazolyl (OCt), ethyl 2-cyano-2-hydroxyiminoacetate, hydroxysuccinimidyl (OSu), hydroxyphthalimidyl (OPhth) $R^8$ substituent examples include F, Cl, an hydroxytriazole derivative, a 2-cyano-2-hydroxyiminoacetate derivative, a N-hydroxysuccinimide or N-hydroxyphthalimide derivative.

II. Synthesis of Precursor

A 2,4-diamino-6-chloro-1,3,5-triazine precursor compound of Formula 2, or a salt thereof, may be prepared to provide access to compounds of Formula I in one step:

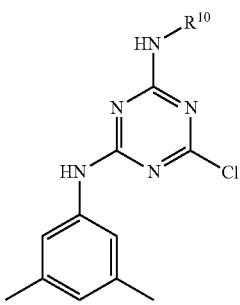

wherein $R^{10}$ is $C_1$-$C_4$ alkyl, for example Me, Et or iPr.

A method to prepare the precursor of Formula 2 is provided in Schemes 5 and 6 below:

Scheme 5

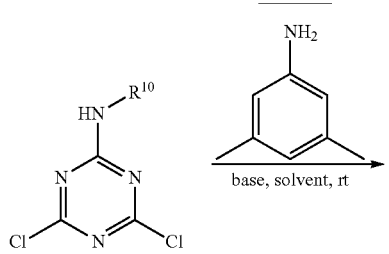

Scheme 6

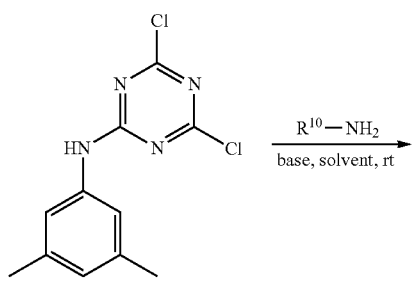

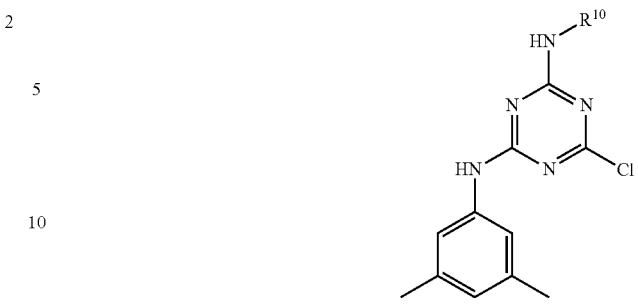

In accordance with Schemes 5-6, a 2-alkylamino-4,6-dichloro-1,3,5-triazine is reacted with 3,5-dimethylaniline, or 2-mexylamino-4,6-dichloro-1,3,5-triazine is reacted with an alkylamine at ambient temperature in the presence of a suitable base in a suitable solvent.

The substituents for Schemes 5-6 are as follows: $R^{10}$ is $C_1$-$C_4$ alkyl, for example Me, Et or iPr.

Examples of the base used in Schemes 5-6 are is $Na_2CO_3$, $K_2CO_3$, triethylamine, N,N-diisopropylethylamine, or the alkylamine with an $R^{10}$ group, and the solvent is acetone or THF.

Compounds of Formula I where $R^1$ is $NHR^{10}$ and $R^2$ is mexyl may be prepared according to Scheme 7:

Scheme 7

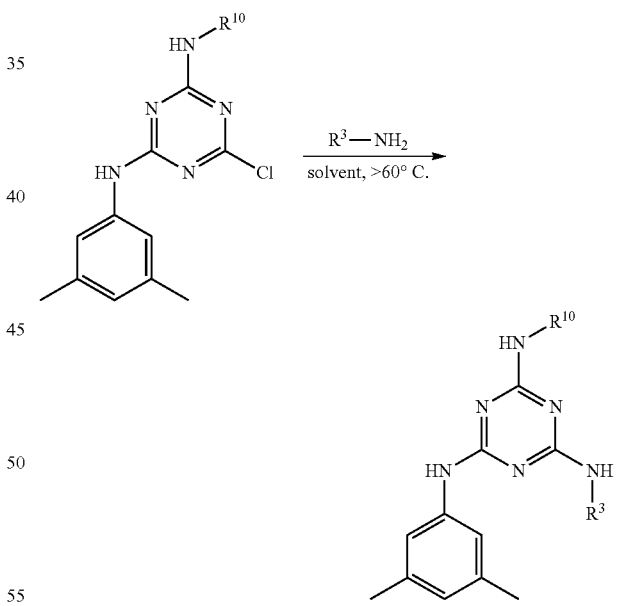

In accordance with Scheme 7, a 2-chloro-4-alkylamino-6-mexylamino-1,3,5-triazine is heated above 60° C. with a primary amine bearing a $R^3$ substituent in acetone or THF.

The substituents for Scheme 7 are as follows:

$R^1$, $R^2$, $R^3$, $R^4$, and $R^5$ as defined herein; and $R^{10}$ is $C_1$-$C_4$ alkyl, for example Me, Et or iPr.

Compounds of Formula I where $R^3$ is 3- or 4-hydroxyphenyl, mercaptophenyl or aminophenyl may be transformed according to the methods shown in Schemes 8 and 9:

Scheme 8

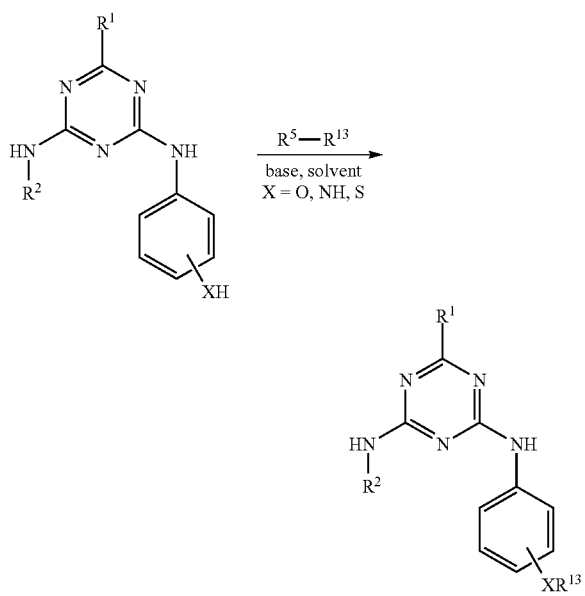

Scheme 9

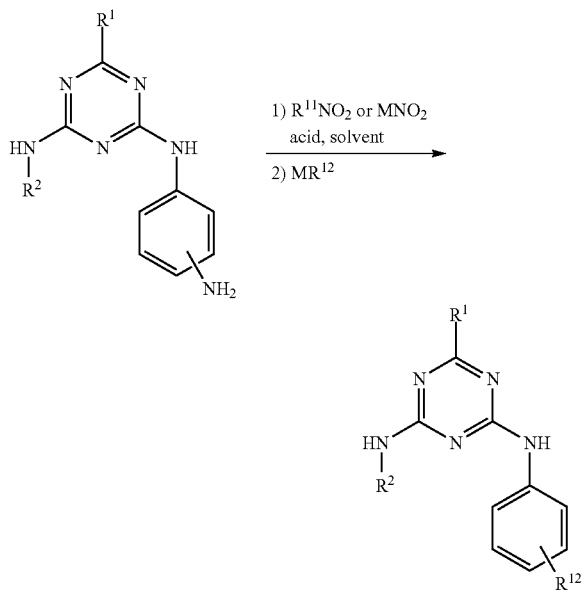

In accordance with Scheme 8, a compound having Formula I and containing a hydroxyl, amino or mercapto group on $R^3$ is reacted with an electrophile in the presence of a non-nucleophilic base in an appropriate solvent. Examples of base include $MnCO_3$, $MnPO_4$, $NR^4_3$, or $MH_n$. Alternatively, according to Scheme 9, a compound having Formula I and containing an amino group on $R^3$ is converted to the corresponding diazonium salt by treating with a suitable nitrosating agent at 0-5° C. in a suitable solvent or mixture of solvents, followed by reaction with a suitable nucleophile.

The substituents for Schemes 8-9 are as follows:

$R^1$, $R^2$, $R^3$, $R^4$, $R^5$ and $R^6$ are as defined herein; and M is any metal, in an appropriate stoichiometry as to balance charges; $R^{13}$ is an alkyl or acyl group containing one or several alkene, alkyne, halogen, sulfonate, alcohol, thiol, amine, azide, epoxy, carbonyl, or carboxyl groups; $R^{11}$ is a $C_1$-$C_6$ alkyl group; and $R^{12}$ is an aromatic group (aryl or heteroaryl) with one or more substituents selected from: amino ($NH_2$) or hydroxy (OH) substituents, azide ($N_3$), cyanide (CN), formaldoxime ($CH_2NOH$), a thiocarboxylate ($R^3C(O)S$), thiolate ($R^3S$), dithiocarbamate ($R^3NC(S)S$) or xanthate ($R^3OC(S)S$ salt, in which $R^3$ is as defined herein.

III. Use of Compounds of Formula I

Compounds having Formula I are reacted with a compound of interest prone to crystallization and bearing a functional group hereafter defined as $R^C$ that can participate in a covalent bond-forming reaction involving the $R^A$ substituent on the $R^3$ group. This reaction bonds the compound having Formula I to the compound of interest in a covalent fashion, and the resulting compound can form glassy phases upon slow cooling and does not recrystallize when heated at rates above 10° C./min. Thus, the following compounds are readily accessible using the compounds of Formula I and reactive $R^A$ substituents located on the $R^3$ group.

In essence, $R^C$ is the same as $R^A$, only on a different molecule. $R^A$ and $R^C$ must react together.

The $R^C$ functional groups are illustrated below:
1) halogen,
2) $OSO_2R^4$,
3) OH,
4) $OCH=CHR^4$,
5) $OCH_2CH=CH_2$,
6) $OCHC=CR^4$
7) $N(R^4)_2$,
8) SH,
9) $P(R^4)_2$,
10) $CH=CHR^4$,
11) $CH=CHC(O)OR^4$,
12) $CCR^4$,
13) $OCH_2C=CH$,
14) CN,
15) $N_3$,
16) CHO,
17) $C(O)R^4$,
18) $CO_2R^4$,
19) $B(OR^4)_2$,
20) $Si(R^4)_3$,
21) $Sn(R^4)_3$.
22) $CH_2Br$,
23) $CH_2OH$,
24) $OCH_2CH(OH)CH_2 OH$,
25)

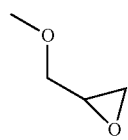

in which the $R^4$ is as defined herein,
26) NCO, and
27) NCS.

Specific examples of $R^C$ functional groups are selected from the group consisting of: $NH_2$, OH, Br, CHO, $CH_2Cl$, $CH_2Br$, $Si(CH_3)_2CH_2Cl$, CCH, and $B(OH)_2$.

Compounds of Interest:
Examples of compounds of interest bearing an $R^C$ functional group are selected from the group consisting of:
1)
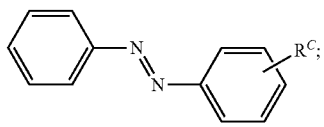
2)
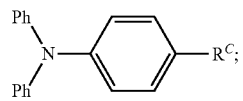
3)
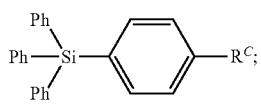
4)
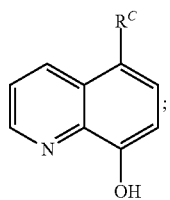
5)
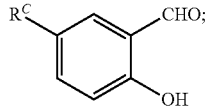
6)
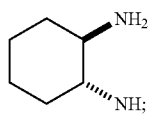
7)
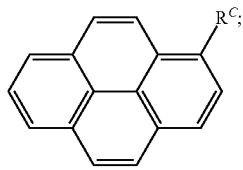
8)
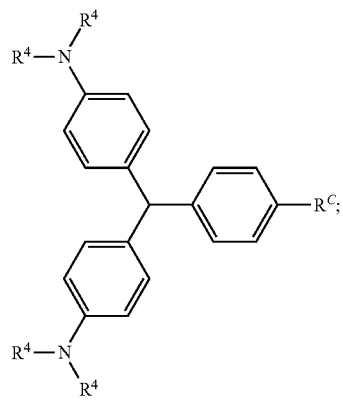
9)
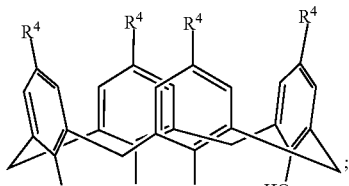
10)
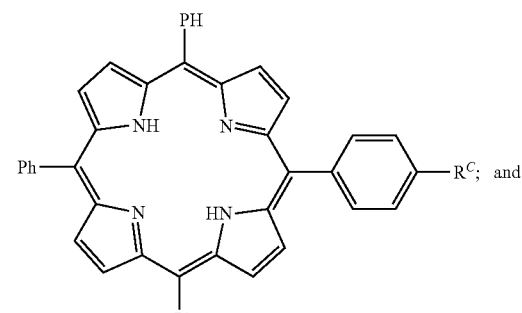
11)
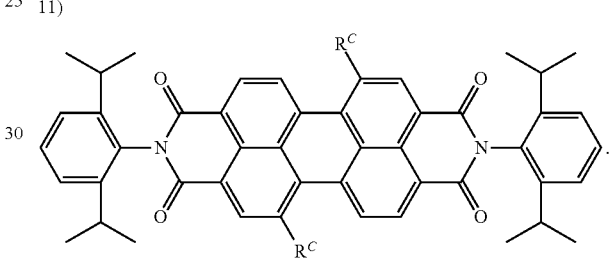
Specific examples of $R^C$ functional groups are selected from the group consisting of:
1)
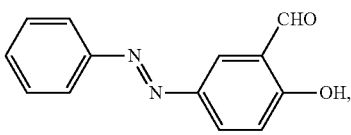
2)
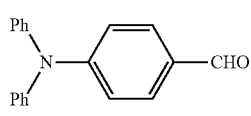
3)
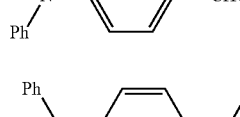
4)
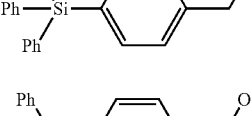
5)
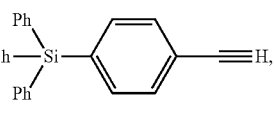

-continued

6) 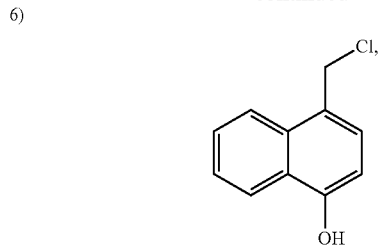

7) 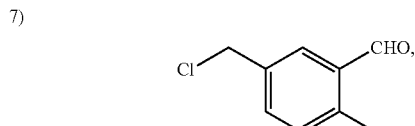

8) 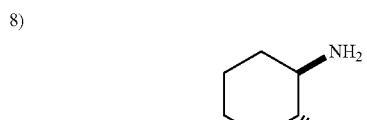

9) 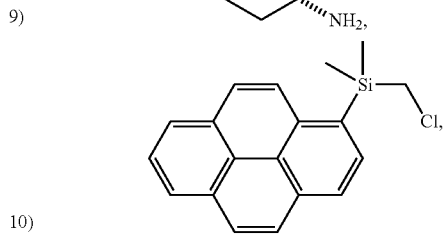

10) 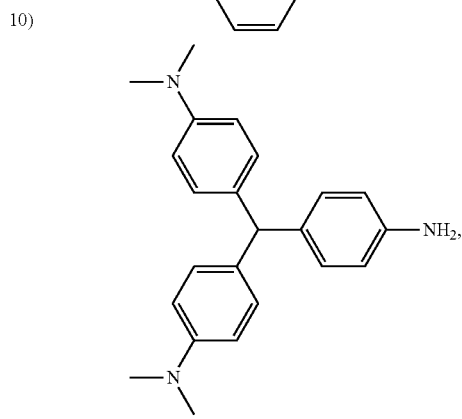

-continued

11) 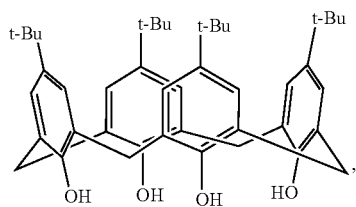

12) 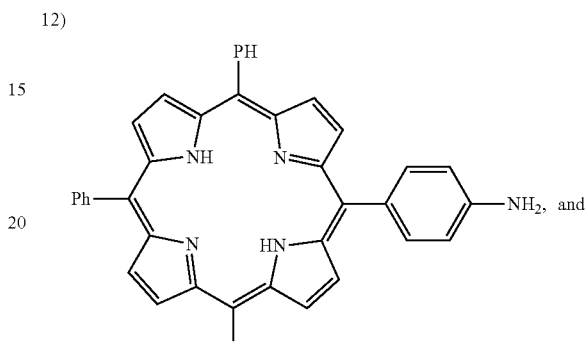

13) 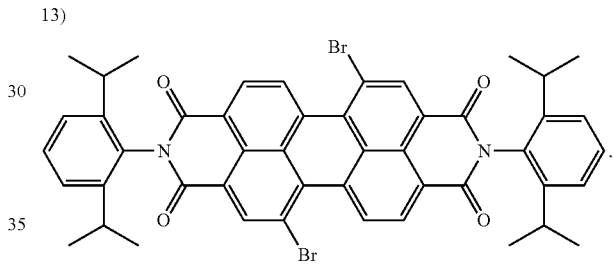

In the examples shown below, the term "Glass" is intended to mean a compound of Formula I that is covalently bonded through a reactive group on the $R^3$ substituent or the $R^C$ functional group on the compounds of interest. In the compounds below, the $R^3$ substituent (including the $R^A$ substituent) is shown and is not part of the "Glass" substituent.

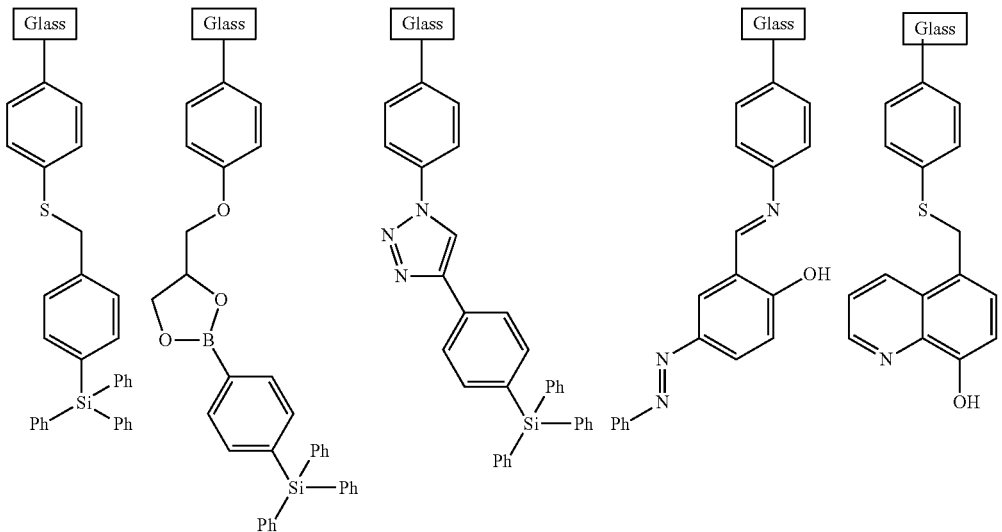

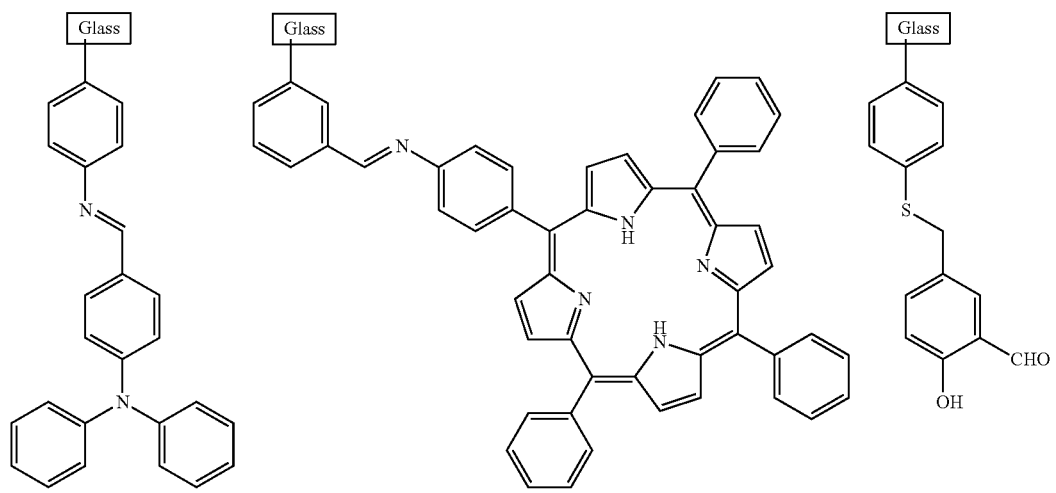
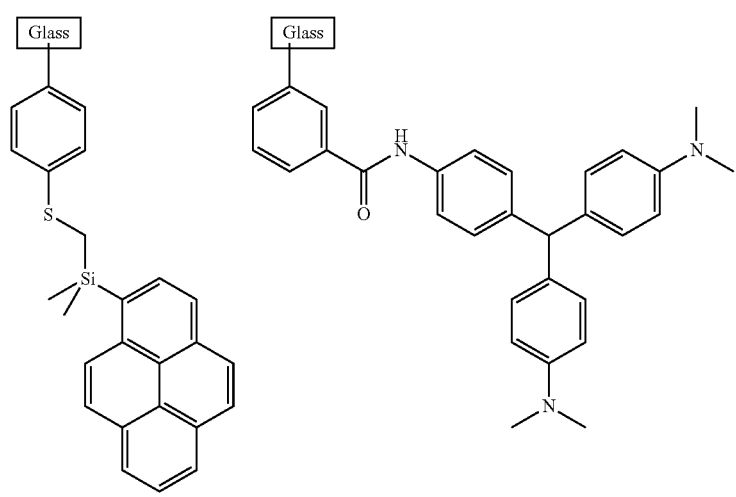
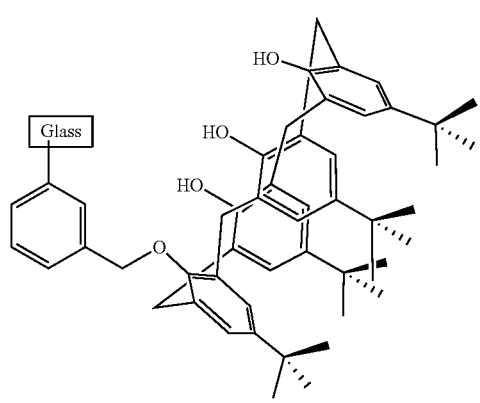
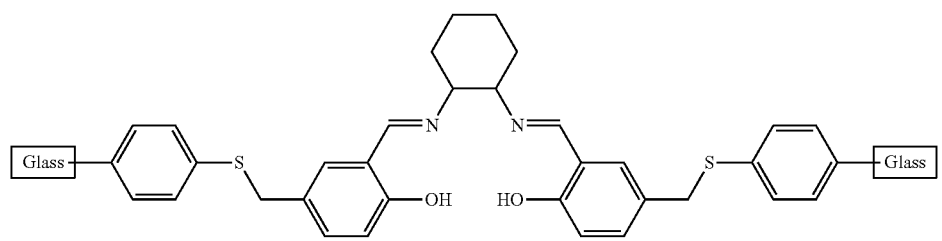

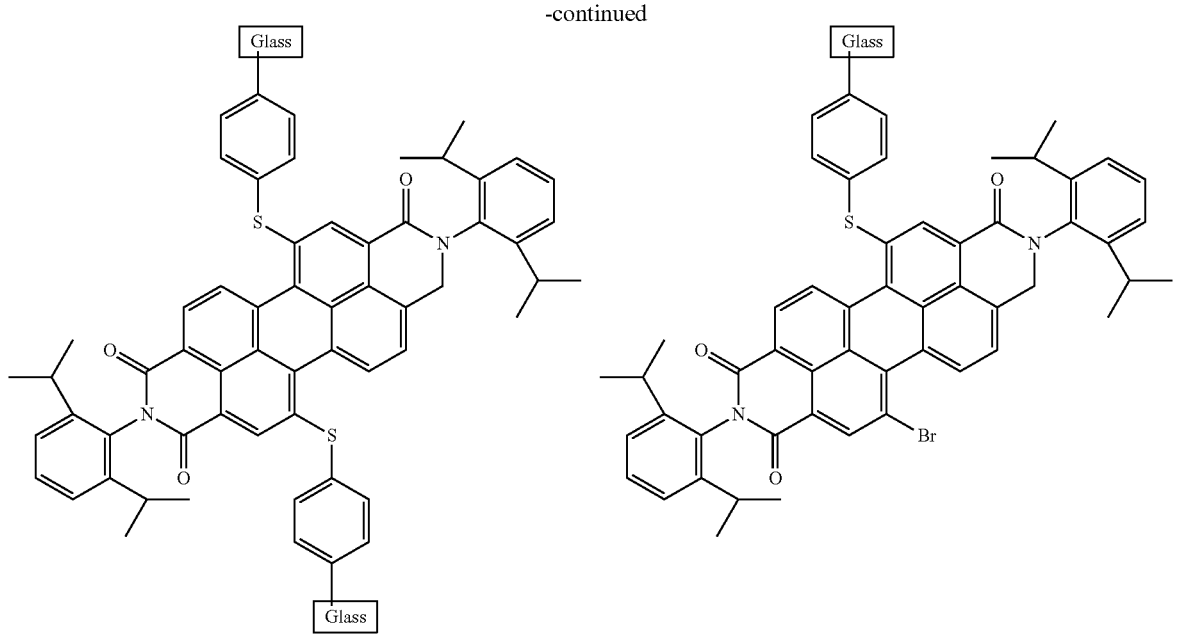

EXAMPLES

1. Synthesis of 2-mexylamino-4-methylamino-6-chloro-1,3,5-triazine (Method A)

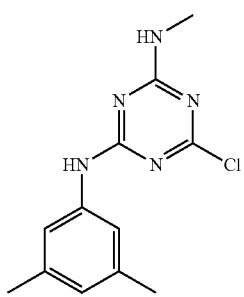 [SMILES: CNc1nc(Cl)nc(Nc2cc(C)cc(C)c2)n1]

2-Methylamino-4,6-dichloro-1,3,5-triazine (18.9 g, 105 mmol) was dissolved in acetone (150 mL) in a round-bottomed flask equipped with a magnetic stirrer. The flask was placed in an ice bath to keep temperature inside the flask under 5° C., then a solution of 3,5-dimethylaniline (13.2 mL, 12.8 g, 105 mmol) in acetone (50 mL) was added dropwise to the mixture. The ice bath was removed once the addition was complete, then the mixture was stirred at r.t. for an additional 30 min, at which point the mixture was poured in $H_2O$ (500 mL), and stirring was continued for 20 min until precipitation was completed. The precipitate was collected by filtration, then the crude product was triturated in hot toluene, filtered and allowed to dry completely to afford 19.2 g pure title compound (72.8 mmol, 69%); $T_m$ 231° C.; FTIR ($CH_2Cl_2$/KBr) 3264, 3196, 3123, 3007, 2914, 2848, 1634, 1615, 1587, 1542, 1453, 1391, 1373, 1276, 1239, 1157, 1125, 1059, 986, 880, 836, 800, 723, 682, 634 cm$^{-1}$; $^1$H NMR (400 MHz, DMSO-$d_6$, 298 K) δ 9.92, 9.75 (s, s, 1H), 8.02, 7.92 (s, s, 1H), 7.40, 7.34 (s, s, 2H), 6.65 (s, 1H), 2.85, 2.80 (s, d, $^3J$=4.6 Hz, 3H), 2.23 (s, 6H); $^1$H NMR (400 MHz, DMSO-$d_6$, 363 K) δ 9.44 (br s, 1H), 7.57 (br s, 1H), 7.35 (s, 2H), 6.68 (s, 1H), 2.86 (s, 3H), 2.25 (s, 6H); $^{13}$C NMR (100 MHz, DMSO-$d_6$) δ 168.3, 167.6, 165.9, 165.8, 163.6, 163.1, 138.8, 138.7, 137.37, 137.35, 124.4, 124.3, 117.9, 117.8, 27.3, 27.2, 21.11, 21.08; HRMS (ESI) calcd. for $C_{12}H_{15}N_5Cl$ m/e: 264.1015. found: 264.1029.

2. Synthesis of 2-mexylamino-4-methylamino-6-chloro-1,3,5-triazine (Method B)

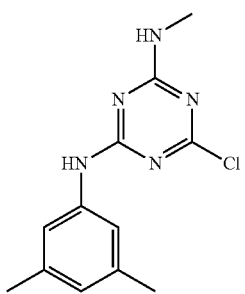 [SMILES: CNc1nc(Cl)nc(Nc2cc(C)cc(C)c2)n1]

2-Mexylamino-4,6-dichloro-1,3,5-triazine (24.3 g, 90.4 mmol) was dissolved in acetone (150 mL) in a round-bottomed flask equipped with a magnetic stirrer. The flask was placed in an ice bath to keep temperature inside the flask under 5° C., then a solution of methylamine (x mL, 40 wt % aq.) in acetone (50 mL) was added dropwise to the mixture. The ice bath was removed once the addition was complete, then the mixture was stirred at r.t. for an additional 30 min, at which point the mixture was poured in $H_2O$ (500 mL), and stirring was continued for 20 min until precipitation was completed. The precipitate was collected by filtration, then the crude product was triturated in hot toluene, filtered and allowed to dry completely to afford 15.9 g pure title compound (60.2 mmol, 67%) with spectroscopic properties in accordance with the product obtained by Method A.

3. Synthesis of 2-(3,5-dichlorophenylamino)-4-methylamino-6-chloro-1,3,5-triazine

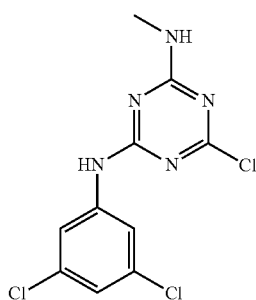 [SMILES: CNc1nc(Cl)nc(Nc2cc(Cl)cc(Cl)c2)n1]

The title compound was synthesized from 2-methylamino-4,6-dichloro-1,3,5-triazine and 3,5-dichloroaniline using a similar procedure to the one used in 2, except with a longer reaction time (18 h instead of 2 h). Yield: 10%; $T_m$ 242° C.; FTIR (CH$_2$Cl$_2$/KBr) 3275, 3184, 3126, 3081, 2960, 2920, 2849, 1641, 1606, 1573, 1546, 1534, 1507, 1448, 1425, 1388, 1306, 1279, 1253, 1237, 1229, 1205, 1165, 1126, 1115, 1107, 1092, 1035, 984, 954, 937, 869, 854, 837, 809, 793, 753, 725 cm$^{-1}$; $^1$H NMR (300 MHz, DMSO-d$_6$, 298 K) δ 10.39, 10.23 (s, s, 1H), 8.24 (s, 1H), 7.86, 7.83 (d, d, $^3J$=1.8 Hz, 2H), 7.23, 7.20 (t, t, $^3J$=1.8 Hz, 1H), 2.86, 2.82 (s, d, $^3J$=4.7 Hz, 3H) ppm; $^{13}$C NMR (75 MHz, DMSO-d$_6$): δ 167.7, 165.7, 165.5, 163.6, 162.9, 141.5, 133.83, 133.77, 121.5, 117.8, 117.6, 27.29, 27.23 ppm; HRMS (EI) calcd. for C$_{10}$H$_8$Cl$_3$N$_5$ (m/e): 302.9845. found: 302.9839.

4. Synthesis of 2-(3,5-dimethoxyphenylamino)-4-methylamino-6-chloro-1,3,5-triazine

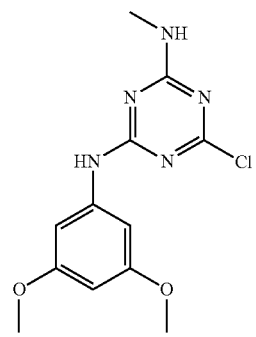 [SMILES: CNc1nc(Cl)nc(Nc2cc(OC)cc(OC)c2)n1]

The title compound was synthesized from 2-methylamino-4,6-dichloro-1,3,5-triazine and 3,5-dimethoxyaniline using a similar procedure to the one used in 2. Yield: 73%; $T_m$ 240° C.; FTIR (CH$_2$Cl$_2$/KBr) 3338, 3254, 3136, 3118, 3001, 2955, 2939, 2907, 2838, 1638, 1614, 1583, 1560, 1536, 1484, 1468, 1455, 1431, 1422, 1397, 1384, 1273, 1251, 1228, 1206, 1191, 1176, 1151, 1127, 1072, 1064, 986, 923, 874, 846, 836, 805, 795, 739, 717, 683 cm$^{-1}$; $^1$H NMR (300 MHz, DMSO-d$_6$, 298 K) δ 10.02, 9.84 (s, s, 1H), 8.12, 8.00 (s, s, 1H), 7.08, 7.00 (s, s, 2H), 6.19 (s, 1H), 3.71 (s, 6H), 2.85, 2.80 (s, d, $^3J$=4.7 Hz, 3H) ppm; $^{13}$C NMR (75 MHz, DMSO-d$_6$): δ 168.3, 167.5, 165.8, 165.7, 163.6, 163.0, 160.2, 140.6, 140.5, 98.5, 98.1, 94.9, 94.5, 54.9, 27.4, 27.2 ppm; HRMS (EI) calcd. for C$_{12}$H$_{14}$ClN$_5$O$_2$ (m/e): 295.0836. found: 295.0843.

5. Synthesis of 2-(3,4,5-trimethoxyphenylamino)-4-methylamino-6-chloro-1,3,5-triazine

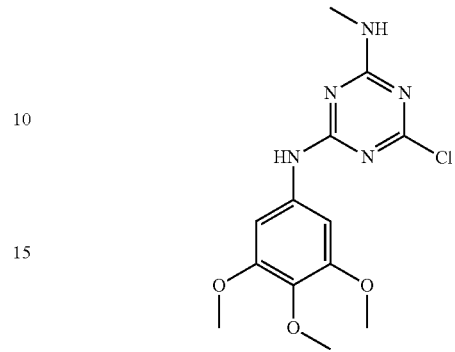

The title compound was synthesized from 2-methylamino-4,6-dichloro-1,3,5-triazine and 3,4,5-trimethoxyaniline using a similar procedure to the one used in 2. Yield: 65%; $T_m$ 237° C.; FTIR (CH$_2$Cl$_2$/KBr) 3270, 3134, 3051, 2964, 2940, 2842, 2831, 1658, 1631, 1612, 1588, 1567, 1535, 1502, 1453, 1422, 1390, 1351, 1297, 1264, 1230, 1201, 1189, 1172, 1128, 1082, 1057, 1034, 997, 978, 924, 882, 830, 809, 735, 704, 679 cm$^{-1}$; $^1$H NMR (300 MHz, DMSO-d$_6$, 298 K) δ 9.97, 9.77 (s, s, 1H), 8.09, 7.91 (s, s, 1H), 7.21, 7.09 (s, s, 2H), 3.74 (s, 6H), 3.61 (s, 3H), 2.86, 2.80 (d, d, $^3J$=4.6 Hz, 3H) ppm; $^{13}$C NMR (75 MHz, DMSO-d$_6$): δ 167.4, 165.8, 165.6, 163.3, 162.9, 152.5, 135.0, 134.8, 133.2, 133.0, 98.2, 97.6, 60.0, 55.8, 55.5, 27.4, 27.2 ppm; HRMS (EI) calcd. for C$_{13}$H$_{16}$ClN$_5$O$_3$ (m/e): 325.0942. found: 325.0934.

6. Synthesis of 2-mexylamino-4-methylamino-6-(4-aminophenylamino)-1,3,5-triazine

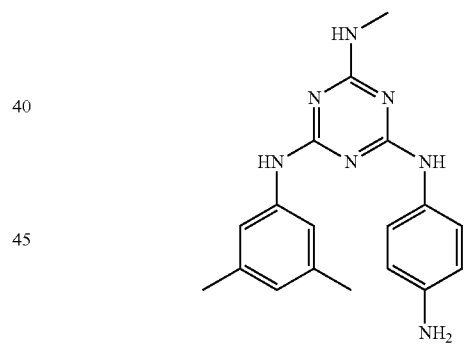

2-Mexylamino-4-methylamino-6-chloro-1,3,5-triazine (2.00 g, 7.58 mmol) and 1,4-phenylenediamine (0.984 g, 9.10 mmol) were dissolved in THF (25 mL) in a round-bottomed flask equipped with a magnetic stirrer and a water-jacketed condenser. Sodium carbonate (0.803 g, 7.58 mmol) was added, then the mixture was refluxed for 16 h. After allowing the mixture to cool down to room temperature, CH$_2$Cl$_2$ and 1M aqueous HCl were added, and a precipitate formed after vigorously stirring the mixture. The precipitate was collected by filtration, then resuspended in CH$_2$Cl$_2$ and extracted with 1M aqueous NaOH. The layers were separated, then the aqueous layer was extracted with CH$_2$Cl$_2$, the organic extracts were combined, dried over Na$_2$SO$_4$, filtered, and the volatiles were thoroughly evaporated under reduced pressure to yield 2.10 g of the title compound in acceptable purity (6.26 mmol, 83%): $T_g$ 102° C.; FTIR (CH$_2$Cl$_2$/KBr) 3402, 3279, 3200, 3024, 2945, 2914, 1572, 1505, 1430, 1399, 1362, 1300, 1264, 1236, 1185, 1037, 838, 809, 777, 689 cm$^{-1}$; $^1$H NMR (300 MHz, DMSO-d$_6$, 298 K): δ 8.82 (br s, 0.5H), 8.66 (br s, 1H), 8.46 (br s, 0.5H), 7.33 (br m, 4H), 6.67 (br s, 1H), 6.55 (s, 1H), 6.49 (d, $^3$J=8.2 Hz, 2H), 4.76 (s, 2H), 2.80 (d, $^3$J=4.7 Hz, 2H), 2.21 (s, 6H) ppm; $^{13}$C NMR (75 MHz, DMSO-d$_6$): δ 166.6, 164.6, 144.3, 140.8, 137.5, 129.7, 123.3, 123.0, 117.9, 114.3, 27.7, 21.7 ppm; HRMS (EI) calcd. for C$_{18}$H$_{21}$N$_7$ (m/e): 335.1858. found: 335.1847.

7. Synthesis of 2-mexylamino-4-methylamino-6-(4-hydroxyphenylamino)-1,3,5-triazine

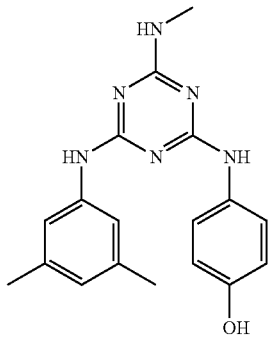 [SMILES: CNc1nc(Nc2ccc(O)cc2)nc(Nc2cc(C)cc(C)c2)n1]

2-Mexylamino-4-methylamino-6-chloro-1,3,5-triazine (10.3 g, 39.0 mmol) and 4-aminophenol (5.11 g, 46.8 mmol) were dissolved in THF (150 mL) in a round-bottomed flask equipped with a magnetic stirrer and a water-jacketed condenser, then the mixture was refluxed for 16 h. After allowing the reaction mixture to cool down to ambient temperature, CH$_2$Cl$_2$ and H$_2$O were added, and both layers were separated. The organic layer was successively extracted with 1M aqueous HCl and saturated aqueous NaHCO$_3$, then recovered, dried over Na$_2$SO$_4$ and filtered. The solvent was thoroughly evaporated in vacuo to yield 12.7 g of the title compound in acceptable purity as a slightly pink-white foam (37.8 mmol, 96%): T$_g$ 95° C.; FTIR (CH$_2$Cl$_2$/KBr) 3446, 3418, 3055, 2987, 1575, 1559, 1510, 1423, 1353, 1266, 1182, 1170, 1093, 1037, 984, 896, 839, 810 cm$^{-1}$; $^1$H NMR (300 MHz, DMSO-d$_6$, 298 K): δ 9.01 (s, 1H), 8.87 (br s, 0.5H), 8.80 (br s, 0.5H), 8.71 (br s, 0.5H), 8.62 (br s, 0.5H), 7.45 (br s, 2H), 7.35 (br d, $^3$J=10.5 Hz, 2H), 6.71 (br s, 1H), 6.65 (d, $^3$J=8.8 Hz, 2H), 6.54 (s, 1H), 2.79 (d, $^3$J=4.7 Hz, 3H), 2.19 (s, 6H) ppm; $^{13}$C NMR (75 MHz, DMSO-d$_6$): δ 166.5, 164.4, 152.9, 140.7, 137.5, 132.1, 123.4, 122.6, 118.0, 115.2, 27.7, 21.7 ppm; HRMS (EI) calcd. for C$_{18}$H$_{20}$N$_6$O (m/e): 336.1699. found: 336.1689.

8. Synthesis of 2-(3,5-dichlorophenylamino)-4-methylamino-6-(4-hydroxyphenylamino)-1,3,5-triazine

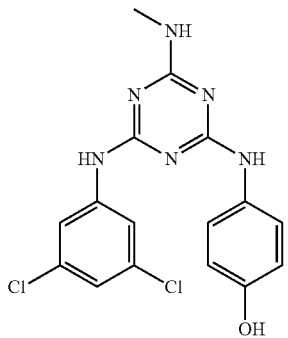 [SMILES: CNc1nc(Nc2ccc(O)cc2)nc(Nc2cc(Cl)cc(Cl)c2)n1]

The title compound was synthesized from 2-(3,5-dichlorophenylamino)-4-methylamino-6-chloro-1,3,5-triazine and 4-aminophenol using a similar procedure to the one used in 8. Yield: 74%; Tg 83° C., T$_c$ 155° C., T$_m$ 187° C.; FTIR (CH$_2$Cl$_2$/KBr) 3401, 3282, 3180, 3112, 2952, 2918, 2850, 1572, 1514, 1503, 1421, 1400, 1366, 1258, 1227, 1168, 1114, 1080, 1011, 993, 937, 833, 807, 737, 703, 668, 632 cm$^{-1}$; $^1$H NMR (300 MHz, DMSO-d$_6$, 298 K): δ 9.43 (br s, 0.5H), 9.29 (br s, 0.5H), 9.00 (br s, 0.5H), 8.83 (br s, 0.5H), 7.90 (br d, 2H), 7.43 (br s, 2H), 7.06 (s, 1H), 7.00 (br s, 1H), 6.70 (d, $^3$J=8.8 Hz, 2H), 2.81 (d, $^3$J=4.1 Hz, 3H) ppm; $^{13}$C NMR (75 MHz, DMSO-d$_6$): δ 165.9, 164.0, 163.6, 152.7, 143.0, 133.6, 131.1, 122.6, 120.0, 117.1, 114.9, 27.2 ppm; HRMS (EI) calcd. for C$_{16}$H$_{14}$Cl$_2$N$_6$O (m/e): 376.0606. found: 376.0601.

9. Synthesis of 2-(3,5-dimethoxyphenylamino)-4-methylamino-6-(4-hydroxyphenylamino)-1,3,5-triazine

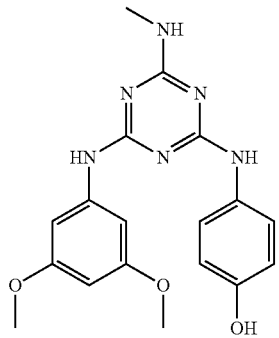 [SMILES: CNc1nc(Nc2ccc(O)cc2)nc(Nc2cc(OC)cc(OC)c2)n1]

The title compound was synthesized from 2-(3,5-dimethoxyphenylamino)-4-methylamino-6-chloro-1,3,5-triazine and 4-aminophenol using a similar procedure to the one used in 7. Yield: 80%; T$_g$ 81° C.; FTIR (CH$_2$Cl$_2$/KBr) 3401, 3288, 3133, 3003, 2958, 2915, 2840, 1587, 1507, 1481, 1450, 1427, 1400, 1360, 1294, 1264, 1234, 1205, 1177, 1153, 1106, 1082, 1065, 1014, 980, 927, 834, 808, 737, 703, 682, 661 cm$^{-1}$; $^1$H NMR (300 MHz, DMSO-d$_6$, 298 K): δ 9.02 (s, 1H), 8.95 (br s, 0.5H), 8.82 (br s, 1H), 8.64 (br s, 0.5H), 7.49 (br s, 2H), 7.09 (br d, 2H), 6.86 (br s, 1H), 6.66 (d, $^3$J=8.8 Hz, 2H), 6.08 (s, 1H), 3.69 (s, 6H), 2.81 (br s, 3H) ppm; $^{13}$C NMR (75 MHz, DMSO-d$_6$): δ 166.0, 164.1, 163.8, 160.2, 152.4, 142.1, 131.6, 122.3, 114.7, 98.0, 93.7, 54.9, 27.3 ppm; HRMS (EI) calcd. for C$_{18}$H$_{20}$N$_6$O$_3$ (m/e): 368.1597. found: 368.1609.

10. Synthesis of 2-(3,4,5-trimethoxyphenylamino)-4-methylamino-6-(4-hydroxyphenylamino)-1,3,5-triazine

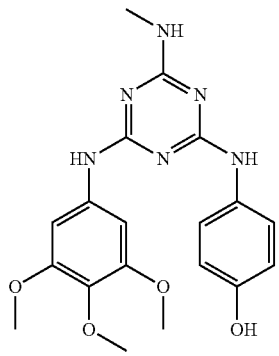 [SMILES: CNc1nc(Nc2ccc(O)cc2)nc(Nc2cc(OC)c(OC)c(OC)c2)n1]

The title compound was synthesized from 2-(3,4,5-trimethoxyphenylamino)-4-methylamino-6-(4-hydroxyphenylamino)-1,3,5-triazine and 4-aminophenol using a similar procedure to the one used in 7. Yield: 79%; T$_g$ 90° C.; FTIR (CH$_2$Cl$_2$/KBr) 3388, 3280, 3121, 2999, 2939, 2917, 2841, 2830, 1653, 1584, 1561, 1501, 1461, 1446, 1420, 1399, 1353, 1301, 1258, 1230, 1202, 1126, 1081, 1041, 996, 870, 830, 807, 786, 734 cm$^{-1}$; $^1$H NMR (300 MHz, DMSO-d$_6$, 298 K): δ 9.03 (s, 1H), 8.89 (br s, 0.5H), 8.78 (br s, 0.5H), 8.75 (br s, 0.5H), 8.61 (br s, 0.5H), 7.48 (br s, 2H), 7.18 (br d, 2H), 6.83 (br s, 1H), 6.66 (d, $^3$J=8.8 Hz, 2H), 3.71 (s, 6H), 3.60 (s, 3H), 2.82 (br s, 3H) ppm; $^{13}$C NMR (75 MHz, DMSO-d$_6$): δ 166.0, 164.0, 163.9, 152.51, 152.46, 136.5, 132.2, 131.7, 122.3, 114.8, 97.7, 60.1, 55.6, 27.3 ppm; HRMS (EI) calcd. for C$_{19}$H$_{22}$N$_6$O$_4$ (m/e): 398.1703. found: 398.1694.

11. Synthesis of 2-mexylamino-4-methylamino-6-(4-mercaptophenylamino)-1,3,5-triazine

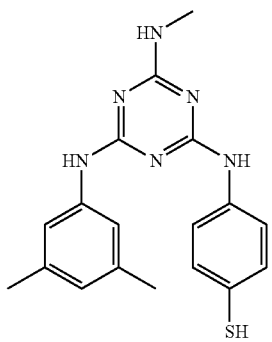 [SMILES: CNc1nc(Nc2ccc(S)cc2)nc(Nc2cc(C)cc(C)c2)n1]

The title compound was synthesized from 2-mexylamino-4-methylamino-6-chloro-1,3,5-triazine and 4-aminothiophenol using a similar procedure to the one used in 4. Yield: 95%; T$_g$ 84° C.; FTIR (CH$_2$Cl$_2$/KBr) 3448, 3416, 3283, 3054, 2987, 1575, 1556, 1496, 1423, 1400, 1355, 1323, 1266, 1183, 896, 841, 810, 705 cm$^{-1}$; $^1$H NMR (300 MHz, DMSO-d$_6$, 298 K): δ 9.09 (br s, 0.5H), 8.96 (br s, 1H), 8.81 (br s, 0.5H), 7.66 (br s, 2H), 7.35 (br d, $^3$J=15.2 Hz, 2H), 7.15 (d, $^3$J=8.2 Hz, 2H), 6.87 (br s, 1H), 6.57 (s, 1H), 5.15 (br s, 1H), 2.81 (d, $^3$J=4.1 Hz, 3H), 2.21 (s, 6H) ppm; $^{13}$C NMR (75 MHz, DMSO-d$_6$): δ 166.6, 164.7, 140.6, 138.7, 137.7, 129.9, 123.8, 123.3, 121.3, 118.4, 27.9, 21.7 ppm; HRMS (EI) calcd. for C$_{18}$H$_{20}$N$_6$S (m/e): 352.1470. found: 352.1477.

12. Synthesis of 2-mexylamino-4-methylamino-6-(4-bromophenylamino)-1,3,5-triazine

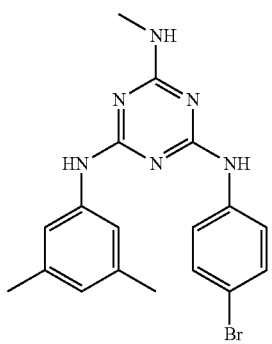 [SMILES: CNc1nc(Nc2ccc(Br)cc2)nc(Nc2cc(C)cc(C)c2)n1]

The title compound was synthesized from 2-mexylamino-4-methylamino-6-chloro-1,3,5-triazine and 4-bromoaniline using a similar procedure to the one used in 7. Yield: 93%; T$_g$ 69° C.; FTIR (CH$_2$Cl$_2$/KBr) 3406, 3274, 3180, 3108, 3020, 2920, 2852, 1599, 1572, 1507, 1489, 1417, 1398, 1360, 1321, 1301, 1285, 1237, 1179, 1073, 1008, 841, 824, 809, 690 cm$^{-1}$; $^1$H NMR (300 MHz, DMSO-d$_6$, 298 K): δ 9.28 (br s, 0.5H), 9.14 (br s, 0.5H), 9.04 (br s, 0.5H), 8.88 (br s, 0.5H), 7.78 (br s, 2H), 7.41 (s, 2H), 7.38 (br s, 2H), 6.96 (br s, 1H), 6.59 (s, 1H), 2.84 (d, $^3$J=4.1 Hz, 3H), 2.23 (s, 6H) ppm; $^{13}$C NMR (75 MHz, DMSO-d$_6$): δ 166.5, 164.6, 164.3, 140.4, 140.3, 137.6, 131.4, 123.8, 122.1, 118.3, 113.3, 27.7, 21.6 ppm; HRMS (EI) calcd. for C$_{18}$H$_{20}$BrN$_6$ (m/e): 396.0855. found: 396.0846.

13. Synthesis of 2-mexylamino-4-methylamino-6-(4-chlorophenylamino)-1,3,5-triazine

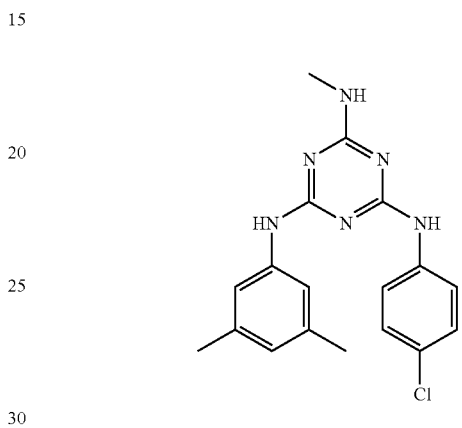

The title compound was synthesized from 2-mexylamino-4-methylamino-6-chloro-1,3,5-triazine and 4-chloroaniline using a similar procedure to the one used in 7. Yield: 66%; T$_g$ 68° C.; FTIR (CH$_2$Cl$_2$/KBr) 3409, 3281, 3198, 3032, 2952, 2918, 2860, 1607, 1573, 1556, 1513, 1502, 1490, 1415, 1401, 1360, 1321, 1300, 1285, 1238, 1184, 1090, 1035, 1012, 976, 958, 940, 887, 827, 810, 738, 692 cm$^{-1}$; $^1$H NMR (300 MHz, DMSO-d$_6$, 298 K): δ 9.27 (br s, 0.5H), 9.12 (br s, 0.5H), 9.02 (br s, 0.5H), 8.87 (br s, 0.5H), 7.83 (br s, 2H), 7.38 (br d, 2H), 7.27 (d, $^3$J=8.2 Hz, 2H), 6.95 (br s, 1H), 6.59 (s, 1H), 2.84 (d, $^3$J=4.1 Hz, 3H), 2.23 (s, 6H) ppm; $^{13}$C NMR (75 MHz, DMSO-d$_6$): δ 166.0, 164.1, 163.8, 139.9, 139.4, 137.1, 128.0, 124.9, 123.3, 121.2, 117.7, 27.2, 21.1 ppm; HRMS (ESI, MH$^+$) calcd. for C$_{18}$H$_{21}$ClN$_6$ (m/e): 355.1438. found: 355.1436.

14. Synthesis of 2-mexylamino-4-methylamino-6-(4-iodophenylamino)-1,3,5-triazine

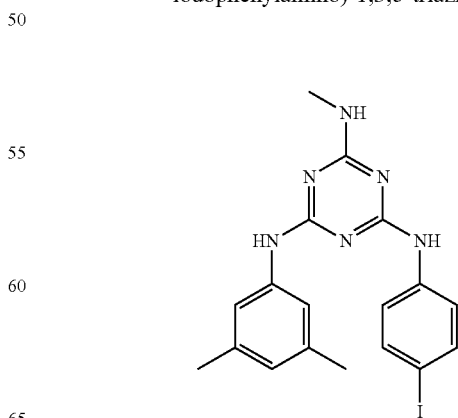

The title compound was synthesized from 2-mexylamino-4-methylamino-6-chloro-1,3,5-triazine and 4-iodoaniline using a similar procedure to the one used in 7. Yield: 51%; $T_g$ 72° C.; FTIR (CH$_2$Cl$_2$/KBr) 3406, 3276, 3178, 3102, 3024, 2951, 2918, 2863, 1597, 1568, 1511, 1501, 1485, 1456, 1425, 1415, 1396, 1360, 1321, 1302, 1283, 1236, 1181, 1168, 1116, 1086, 1062, 1036, 1004, 976, 957, 939, 888, 841, 821, 809, 737, 703, 688 cm$^{-1}$; $^1$H NMR (300 MHz, DMSO-d$_6$, 298 K): δ 9.25 (br s, 0.5H), 9.10 (br s, 0.5H), 9.02 (br s, 0.5H), 8.87 (br s, 0.5H), 7.64 (br s, 2H), 7.55 (d, $^3$J=8.2 Hz, 2H), 7.38 (br d, 2H), 6.95 (br s, 1H), 6.59 (s, 1H), 2.84 (d, $^3$J=4.1 Hz, 3H), 2.22 (s, 6H) ppm; $^{13}$C NMR (75 MHz, DMSO-d$_6$): δ 166.0, 164.0, 163.7, 140.3, 139.9, 137.1, 136.7, 123.3, 122.1, 117.7, 84.3, 27.2, 21.1 ppm; HRMS (ESI, MH$^+$) calcd. for C$_{18}$H$_{21}$IN$_6$ (m/e): 447.0794. found: 447.0782.

15. Synthesis of 2-mexylamino-4-methylamino-6-(4-allyloxyphenylamino)-1,3,5-triazine

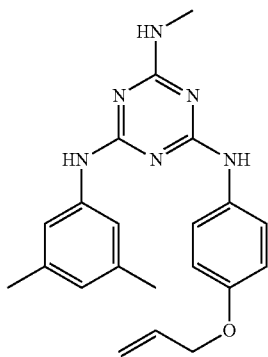 [SMILES: C=CCOc1ccc(Nc2nc(NC)nc(Nc3cc(C)cc(C)c3)n2)cc1]

2-Mexylamino-4-methylamino-6-(4-hydroxyphenylamino)-1,3,5-triazine (0.336 g, 1.00 mmol), potassium carbonate (0.276 g, 2.00 mmol), and allyl bromide (0.170 mL, 0.242 g, 2.00 mmol) in DMF (2 mL) in a round-bottomed flask equipped with a magnetic stirrer were stirred at ambient temperature for 18 h. The mixture was then poured into H$_2$O, ether was added, and both layers were separated. The organic layer was extracted with H$_2$O, dried over Na$_2$SO$_4$, filtered, and the volatiles were thoroughly evaporated under reduced pressure (at no higher than 60° C.) to yield 0.325 g of the title compound (0.863 mmol, 86%): $T_g$ 50° C., $T_{dec}$ 142° C. (Claisen rearrangement); FTIR (CH$_2$Cl$_2$/KBr) 3450, 3419, 3280, 3054, 2987, 2922, 2862, 1572, 1559, 1508, 1424, 1399, 1354, 1322, 1300, 1264, 1241, 1224, 1176, 1024, 997, 929, 896, 831, 810, 705 cm$^{-1}$; $^1$H NMR (300 MHz, DMSO-d$_6$, 298 K): δ 8.95 (br s, 1H), 8.80 (br s, 1H), 7.64 (br s, 2H), 7.39 (br d, 2H), 6.86 (d, $^3$J=9.4 Hz, 2H), 6.81 (br s, 1H), 6.57 (s, 1H), 6.04 (ddt, $^3$J$_{CH2}$=5.3 Hz, $^3$J$_{cis}$=10.5 Hz, $^3$J$_{trans}$=17.6 Hz, 1H), 5.39 (dd, $^2$J=1.8 Hz, $^3$J$_{trans}$=17.6 Hz, 1H), 5.25 (dd, $^2$J=1.8 Hz, $^3$J$_{cis}$=10.5 Hz, 1H), 4.52 (d, 3J=5.3 Hz, 2H), 2.83 (d, 3J=4.7 Hz, 3H), 2.22 (s, 6H) ppm; $^{13}$C NMR (75 MHz, DMSO-d$_6$): δ 166.0, 164.0, 163.8, 153.1, 140.1, 137.0, 133.9, 133.4, 123.0, 121.5, 117.5, 117.1, 114.3, 68.3, 27.2, 21.1 ppm; HRMS (EI) calcd. for C$_{21}$H$_{24}$N$_6$O (m/e): 376.2012. found: 376.2023.

16. Synthesis of 2-mexylamino-4-methylamino-6-(4-propargyloxyphenylamino)-1,3,5-triazine

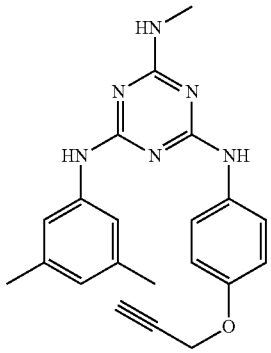 [SMILES: C#CCOc1ccc(Nc2nc(NC)nc(Nc3cc(C)cc(C)c3)n2)cc1]

The title compound was synthesized from 2-mexylamino-4-methylamino-6-(4-hydroxyphenylamino)-1,3,5-triazine and propargyl bromide (80 wt % in toluene) using a procedure similar to the one used in 7, though under nitrogen atmosphere and in the absence of light. Yield: 79%; $T_g$ 44° C.; FTIR (CH$_2$Cl$_2$/KBr) 3446, 3417, 3302, 3055, 2986, 2126, 1675, 1577, 1557, 1508, 1423, 1265, 1213, 1177, 1031, 896, 833, 810, 704 cm$^{-1}$; $^1$H NMR (300 MHz, DMSO-d$_6$, 298 K): δ 8.99 (br s, 0.5H), 8.93 (br s, 0.5H), 8.82 (br s, 0.5H), 8.78 (br s, 0.5H), 7.66 (br s, 2H), 7.39 (br d, 2H), 6.90 (d, $^3$J=8.8 Hz, 2H), 6.82 (br s, 1H), 6.57 (s, 1H), 4.73 (d, $^4$J=2.3 Hz, 2H), 3.54 (t, 4J=2.3 Hz, 1H), 2.82 (d, $^3$J=4.7 Hz, 3H), 2.22 (s, 6H) ppm; $^{13}$C NMR (75 MHz, DMSO-d$_6$): δ 166.0, 164.0, 163.8, 152.1, 140.1, 137.0, 134.1, 123.0, 121.4, 117.5, 114.6, 79.5, 77.9, 55.6, 27.2, 21.1 ppm; HRMS (EI) calcd. for C$_{21}$H$_{22}$N$_6$O (m/e): 374.1855. found: 374.1867.

17. Synthesis of 2-mexylamino-4-methylamino-6-[4-(2,3-dihydroxypropoxyl)phenylamino]-1,3,5-triazine

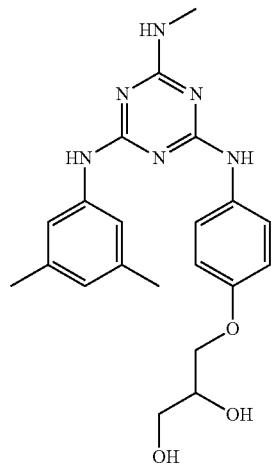 [SMILES: CNc1nc(Nc2ccc(OCC(O)CO)cc2)nc(Nc2cc(C)cc(C)c2)n1]

To a stirred solution of 2-mexylamino-4-methylamino-6-(4-allyloxyphenylamino)-1,3,5-triazine (0.376 g, 1.00 mmol)

in acetone (10 mL) in a round-bottomed flask equipped with a magnetic stirrer was slowly added a solution of potassium permanganate (0.166 g, 1.05 mmol) in water (20 mL) while maintaining the temperature below 5° C. The mixture was then stirred 1 h at ambient temperature, then AcOEt was added, and the precipitated MnO$_2$ was removed by filtration and washed with AcOEt. The two layers were separated, the aqueous layer was extracted with AcOEt, and the combined organic extracts were extracted with aqueous 1M HCl, aqueous NaHCO$_3$ and brine, dried over Na$_2$SO$_4$, filtered, then the volatiles were thoroughly evaporated under reduced pressure to give 0.254 g of the title compound (0.619 mmol, 62%): T$_g$ 70° C.; FTIR (CH$_2$Cl$_2$/KBr) 3407, 3294, 3121, 3053, 2986, 2941, 2870, 1573, 1507, 1423, 1399, 1265, 1231, 1175, 1114, 1042, 895, 831, 809, 704 cm$^{-1}$; $^1$H NMR (300 MHz, DMSO-d$_6$, 298 K): δ 8.94 (br s, 1H), 8.78 (br s, 1H), 7.62 (br s, 2H), 7.38 (br d, 2H), 6.83 (d, $^3$J=8.8 Hz, 2H), 6.83 (br s, 1H), 6.57 (s, 1H), 4.91 (d, $^3$J=4.1 Hz, 1H), 4.64 (t, $^3$J=5.3 Hz, 1H), 3.94 (m, 1H), 3.79 (m, 2H), 3.44 (m, 2H), 2.82 (d, $^3$J=4.7 Hz, 3H), 2.21 (s, 6H) ppm; $^{13}$C NMR (75 MHz, DMSO-d$_6$): δ 166.0, 164.1, 163.9, 153.8, 140.1, 137.0, 133.2, 123.0, 121.7, 117.5, 114.1, 69.9, 69.7, 62.7, 27.2, 21.1 ppm; HRMS (EI) calcd. for C$_{21}$H$_{26}$N$_6$O$_3$ (m/e): 410.2066. found: 410.2078.

18. Synthesis of 2-mexylamino-4-methylamino-6-(4-glycidyloxyphenylamino)-1,3,5-triazine

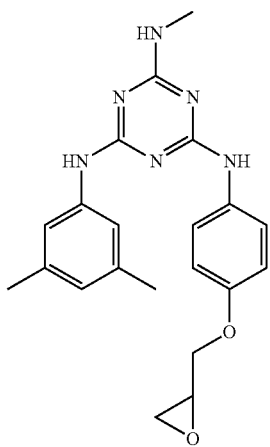 [SMILES: CNc1nc(Nc2ccc(OCC3CO3)cc2)nc(Nc2cc(C)cc(C)c2)n1]

2-Mexylamino-4-methylamino-6-(4-hydroxyphenylamino)-1,3,5-triazine (1.00 g, 2.97 mmol), potassium carbonate (1.64 g, 11.9 mmol), and epichlorohydrin (0.930 mL, 1.10 g, 11.9 mmol) were added in acetone (5 mL) in a round-bottomed flask equipped with a magnetic stirrer. The flask was equipped with a water-jacketed condenser and the mixture was refluxed for 18 h. The mixture was then poured into H$_2$O, then the gummy precipitate was filtered and washed with H$_2$O, then redissolved in CH$_2$Cl$_2$. The solution was extracted twice with aqueous 1M NaOH and H$_2$O, dried over Na$_2$SO$_4$, filtered, and the volatiles were thoroughly evaporated under reduced pressure to yield 1.00 g of the title compound (2.55 mmol, 86%): T$_g$ 74° C.; FTIR (CH$_2$Cl$_2$/KBr) 3446, 3418, 3285, 3055, 2987, 2925, 2854, 1575, 1557, 1509, 1424, 1399, 1266, 1177, 1039, 896, 841, 810, 704 cm$^{-1}$; $^1$H NMR (400 MHz, DMSO-d$_6$, 298 K): δ 8.98 (br s, 0.5H), 8.93 (br s, 0.5H), 8.82 (br s, 0.5H), 8.79 (br s, 0.5H), 7.66 (br s, 2H), 7.39 (br d, 2H), 6.87 (d, $^3$J=8.8 Hz, 2H), 6.83 (br s, 1H), 6.57 (s, 1H), 4.27 (dd, J$_1$=2.5 Hz, J$_2$=11.4 Hz, 1H), 3.78 (dd, J$_1$=6.3 Hz, J$_2$=11.4 Hz, 1H), 3.32 (m, 1H), 2.84 (d, $^3$J=4.5 Hz, 3H), 2.83 (m, 1H), 2.70 (m, 1H), 2.22 (s, 6H) ppm; $^{13}$C NMR (75 MHz, DMSO-d$_6$): δ 166.0, 164.0, 153.2, 140.1, 137.0, 133.7, 123.0, 121.6, 117.5, 114.2, 69.1, 49.7, 43.7, 27.2, 21.1 ppm; HRMS (EI) calcd. for C$_{21}$H$_{24}$N$_6$O$_2$ (m/e): 392.1961. found: 392.1977.

19. Synthesis of 2-mexylamino-4-methylamino-6-(4-azidophenylamino)-1,3,5-triazine

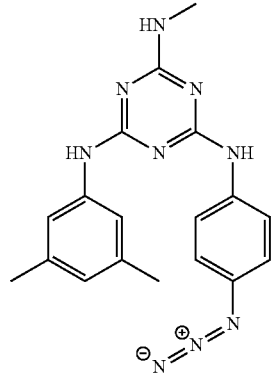 [SMILES: CNc1nc(Nc2ccc(N=[N+]=[N-])cc2)nc(Nc2cc(C)cc(C)c2)n1]

2-Mexylamino-4-methylamino-6-(4-aminophenylamino)-1,3,5-triazine (0.335 g, 1.00 mmol) was dissolved in THF (5 mL) in a round-bottomed flask equipped with a magnetic stirrer. 10% aq. HCl (5 mL) was added, then the flask was placed in an ice bath, and a solution of sodium nitrite (0.0690 g, 1.00 mmol) in H$_2$O (1 mL) was added dropwise. The mixture was stirred at 0-5° C. for 30 min. A solution of sodium azide (0.0980 g, 1.50 mmol) in H$_2$O (1 mL) was then added dropwise, then the mixture was stirred for 1 h while allowing to warm up to ambient temperature. AcOEt and H$_2$O were added, both layers were shaken vigorously, then the remaining precipitate was removed by filtration and washed with AcOEt, and both layers were separated. The organic layer was extracted with aqueous NaHCO$_3$, dried over Na$_2$SO$_4$, filtered, and the volatiles were thoroughly evaporated under reduced pressure (at no higher than 60° C.) to yield 0.224 g of the title compound (0.620 mmol, 62%): T$_g$ 52° C.; FTIR (CH$_2$Cl$_2$/KBr) 3450, 3418, 3055, 2987, 2121, 1575, 1556, 1504, 1422, 1355, 1265, 1182, 988, 896, 835, 810, 706 cm$^{-1}$; $^1$H NMR (300 MHz, DMSO-d$_6$, 298 K): δ 9.22 (br s, 0.5H), 9.08 (br s, 0.5H), 9.00 (br s, 0.5H), 8.84 (br s, 0.5H), 7.83 (br s, 2H), 7.38 (br d, 2H), 6.99 (d, $^3$J=8.8 Hz, 2H), 6.92 (br s, 1H), 6.59 (s, 1H), 2.83 (d, $^3$J=4.1 Hz, 3H), 2.22 (s, 6H) ppm; $^{13}$C NMR (75 MHz, DMSO-d$_6$): δ 166.0, 164.0, 163.8, 139.4, 137.7, 137.0, 131.9, 123.1, 121.2, 118.9, 117.7, 27.2, 21.1 ppm; HRMS (EI) calcd. for C$_{18}$H$_{19}$N$_9$ (m/e): 361.1763. found: 361.1776.

20. Synthesis of 2-mexylamino-4-methylamino-6-(3-carboxyphenylamino)-1,3,5-triazine

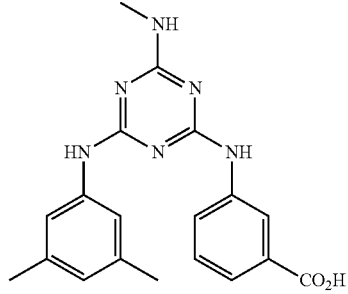 [SMILES: CNc1nc(Nc2cc(C)cc(C)c2)nc(Nc2cccc(C(=O)O)c2)n1]

2-Mexylamino-4-methylamino-6-chloro-1,3,5-triazine (1.06 g, 3.94 mmol) and 3-aminobenzoic acid (0.811 g, 5.92 mmol) were added in THF (50 mL) in a round-bottomed flask equipped with a magnetic stirrer and a water-jacketed condenser. The mixture was refluxed for 18 h, then once the mixture had cooled down to room temperature the precipitate was collected by filtration and abundantly washed with THF, water and acetone. The crude product was resuspended in $H_2O$, $NaHCO_3$ (1.68 g, 20.0 mmol) was added, then glacial AcOH was added with stirring until the pH of the solution was 4-5. The precipitate was collected by filtration, washed with water, and dried overnight in an oven to yield 1.17 g of the title compound (3.21 mmol, 81%): $T_g$ 131° C., $T_m$ 263° C.; FTIR ($CH_2Cl_2$/KBr) 3356, 3275, 3098, 3011, 2951, 2918, 2850, 1690, 1668, 1614, 1574, 1519, 1428, 1385, 1343, 1299, 1260, 1237, 1166, 1077, 1019, 998, 936, 908, 882, 839, 806, 776, 756, 705, 684 $cm^{-1}$; $^1$H NMR (300 MHz, DMSO-$d_6$, 298 K): δ 9.31 (br s, 0.5H), 9.16 (br s, 0.5H), 9.01 (br s, 0.5H), 8.83 (br s, 0.5H), 8.30 (m, 1H), 8.08 (m, 1H), 7.53 (d, $^3J$=7.6 Hz, 1H), 7.39 (s, 2H), 7.37 (t, $^3J$=8.2 Hz, 1H), 6.94 (br s, 1H), 6.58 (s, 1H), 2.85 (br s, 3H), 2.21 (s, 6H) ppm; $^{13}$C NMR (75 MHz, DMSO-$d_6$): δ 167.5, 166.1, 164.2, 164.0, 140.6, 140.0, 137.2, 131.1, 128.5, 124.4, 123.3, 122.4, 121.0, 117.7, 27.3, 21.1 ppm; HRMS (EI) calcd. for $C_{19}H_{20}N_6O_2$ (m/e): 364.1648. found: 364.1639.

21. Synthesis of 2-mexylamino-4-methylamino-6-(4-(2-ethoxycarbonylvinyl)-phenylamino)-1,3,5-triazine

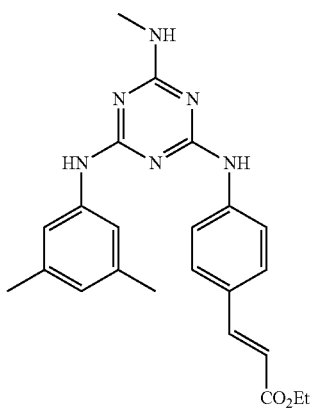 [SMILES: CCOC(=O)/C=C/c1ccc(Nc2nc(NC)nc(Nc3cc(C)cc(C)c3)n2)cc1]

The title compound was synthesized from 2-mexylamino-4-methylamino-6-chloro-1,3,5-triazine and ethyl 4-aminocinnamate using a similar procedure to the one used in 7. Yield: 97%; $T_g$ 70° C.; FTIR ($CH_2Cl_2$/KBr) 3402, 3283, 3188, 3106, 2980, 2948, 2919, 2871, 1701, 1606, 1575, 1504, 1417, 1363, 1325, 1304, 1265, 1237, 1207, 1178, 1037, 982, 883, 835, 809, 739 $cm^{-1}$; $^1$H NMR (300 MHz, DMSO-$d_6$, 298 K): δ 9.42 (br s, 0.5H), 9.28 (br s, 0.5H), 9.07 (br s, 0.5H), 8.93 (br s, 0.5H), 7.89 (br s, 2H), 7.60 (d, $^3J$=8.2 Hz, 2H), 7.60 (d, $^3J_{trans}$=15.8 Hz, 1H), 7.40 (br s, 2H), 7.01 (br s, 1H), 6.61 (s, 1H), 6.48 (d, $^3J_{trans}$=15.8 Hz, 1H), 4.18 (q, $^3J$=7.0 Hz, 2H), 2.85 (d, $^3J$=4.1 Hz, 3H), 2.24 (s, 6H), 1.25 (t, $^3J$=7.0 Hz, 3H) ppm; $^{13}$C NMR (75 MHz, DMSO-$d_6$): δ 166.5, 166.0, 164.0, 163.7, 144.4, 142.8, 139.9, 137.1, 128.9, 126.9, 123.3, 119.3, 117.8, 115.0, 59.7, 27.3, 21.1, 14.2 ppm; HRMS (ESI, MH$^+$) calcd. for $C_{23}H_{27}N_6O_2$ (m/e): 419.2195. found: 419.2177.

22. Synthesis of 2-mexylamino-4-methylamino-6-(3-hydroxymethylphenylamino)-1,3,5-triazine

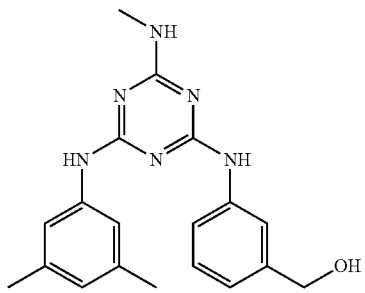 [SMILES: CNc1nc(Nc2cc(C)cc(C)c2)nc(Nc2cccc(CO)c2)n1]

2-Mexylamino-4-methylamino-6-chloro-1,3,5-triazine (2.59 g, 9.82 mmol) and 3-aminobenzoic acid (1.45 g, 11.8 mmol) were added in THF (50 mL) in a round-bottomed flask equipped with a magnetic stirrer and a water-jacketed condenser. The mixture was refluxed for 3 h, at which point a precipitate had formed. The precipitate was collected by filtration and washed with $CH_2Cl_2$, resuspended in MeOH, then AcOEt and aqueous $NaHCO_3$ were added and the mixture was shaken in an extraction funnel. Both layers were separated, the aqueous layer was extracted with a second portion of AcOEt, then the combined organic extracts were washed with $H_2O$ and brine, dried over $Na_2SO_4$, filtered, and the volatiles were thoroughly evaporated under vacuum to yield 2.60 g of the title compound (7.42 mmol, 76%): $T_g$ 69° C.; FTIR ($CH_2Cl_2$/KBr) 3401, 3376, 3286, 3021, 2943, 2921, 2869, 1611, 1583, 1565, 1553, 1527, 1514, 1487, 1461, 1434, 1400, 1362, 1321, 1301, 1262, 1245, 1188, 1177, 1166, 1083, 1037, 1012, 998, 973, 956, 890, 842, 808, 784, 736, 693, 650 $cm^{-1}$; $^1$H NMR (300 MHz, DMSO-$d_6$, 298 K): δ 9.01 (br s, 0.5H), 8.97 (br s, 1H), 8.80 (br s, 0.5H), 7.77 (t, $^3J$=7.6 Hz, 1H), 7.56 (br s, 1H), 7.40 (br d, 2H), 7.20 (t, $^3J$=7.6 Hz, 1H), 6.92 (d, $^3J$=7.6 Hz, 1H), 6.89 (br s, 1H), 6.58 (s, 1H), 5.13 (t, $^3J$=5.9 Hz, 1H), 4.46 (d, $^3J$=5.9 Hz, 2H), 2.85 (d, $^3J$=4.7 Hz, 3H), 2.22 (s, 6H) ppm; $^{13}$C NMR (75 MHz, DMSO-$d_6$): δ 166.1, 164.1, 163.9, 142.6, 140.1, 137.1, 127.9, 123.1, 119.7, 118.3, 118.1, 117.6, 63.1, 27.2, 21.1 ppm; HRMS (EI) calcd. for $C_{19}H_{22}N_6O$ (m/e): 350.1855. found: 350.1848.

23. Synthesis of 2-mexylamino-4-methylamino-6-(3-formylphenylamino)-1,3,5-triazine

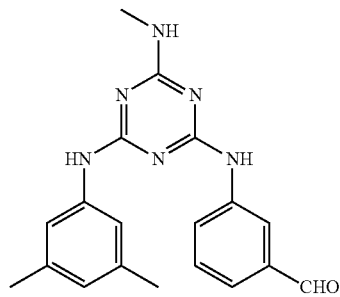 [SMILES: CNc1nc(Nc2cc(C)cc(C)c2)nc(Nc2cccc(C=O)c2)n1]

2-Mexylamino-4-methylamino-6-(3-hydroxymethylphenylamino)-1,3,5-triazine (0.350 g, 1.00 mmol) was dissolved in dry $CH_2Cl_2$ (5 mL) in a dry round-bottomed flask equipped with a magnetic stirrer. PCC (0.647 g, 3.00 mmol) was added, then the mixture was stirred 3 h at ambient temperature under inert atmosphere. Anhydrous EtOH (1 mL) was then added and the mixture was stirred 15 min to destroy remaining PCC, then the mixture was diluted with aqueous 1M NaOH and $CH_2Cl_2$. The mixture was thoroughly shaken, then both layers were separated. The organic layer was further extracted with aqueous 1M NaOH, $H_2O$ and brine, dried over $Na_2SO_4$, filtered, then the solvent was thoroughly evaporated under reduced pressure to yield 0.296 g of the title compound (0.850 mmol, 85%): $T_g$ 59° C.; FTIR ($CH_2Cl_2$/KBr) 3405, 3281, 3201, 3124, 3050, 3022, 2960, 2921, 2857, 2730, 1697, 1613, 1580, 1566, 1556, 1526, 1507, 1483, 1429, 1396, 1360, 1320, 1301, 1263, 1244, 1187, 1176, 1157, 1088, 1036, 998, 975, 958, 886, 843, 809, 792, 737, 702, 684 cm$^{-1}$; $^1$H NMR (300 MHz, DMSO-$d_6$, 298 K): δ 9.93 (s, 1H), 9.43 (br s, 0.5H), 9.28 (br s, 0.5H), 9.05 (br s, 0.5H), 8.87 (br s, 0.5H), 8.42 (br s, 0.5H), 8.26 (br s, 0.5H), 8.13 (br d, 1H), 7.49 (br s, 2H), 7.39 (br d, 2H), 7.00 (br s, 1H), 6.60 (s, 1H), 2.85 (d, $^3J$=4.1 Hz, 3H), 2.22 (s, 6H) ppm; $^{13}$C NMR (75 MHz, DMSO-$d_6$): δ 193.1, 166.0, 164.1, 163.8, 141.2, 139.9, 137.0, 136.5, 129.0, 125.4, 123.2, 122.4, 120.8, 117.8, 27.2, 21.1 ppm; HRMS (EI) calcd. for $C_{19}H_{20}N_6O$ (m/e): 348.1699. found: 348.1693.

24. Synthesis of 2-mexylamino-4-methylamino-6-(3-bromomethylphenylamino)-1,3,5-triazine

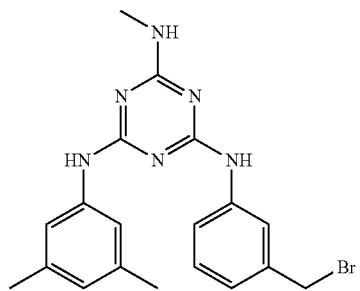 [SMILES: CNc1nc(Nc2cc(C)cc(C)c2)nc(Nc2cccc(CBr)c2)n1]

2-Mexylamino-4-methylamino-6-(3-hydroxymethylphenylamino)-1,3,5-triazine (0.350 g, 1.00 mmol) was dissolved in dry $CH_2Cl_2$ (2 mL) in a dry round-bottomed flask equipped with a magnetic stirrer. The solution was cooled down to 0° C., and PBr$_3$ (0.282 mL, 0.81 g, 3.00 mmol) was added dropwise under inert atmosphere. Once the addition was complete, the mixture was stirred under inert atmosphere at ambient temperature for 18 h. A precipitate started forming after 2-3 h. The mixture was poured into aqueous NaHCO$_3$, THF and $CH_2Cl_2$ were added, then after stirring for 20 min to ensure that the mixture was completely neutralized, the remaining precipitate was removed by filtration and both layers were separated. The aqueous layer was extracted with $CH_2Cl_2$, then the combined organic extracts were extracted with aqueous NaHCO$_3$ and brine, dried over Na$_2$SO$_4$, filtered, and the volatiles were thoroughly evaporated under reduced pressure to yield 0.348 g of the title compound (0.840 mmol, 84%): $T_g$ 62° C., $T_{dec}$ 131° C.; FTIR ($CH_2Cl_2$/KBr) 3399, 3275, 3171, 3137, 3023, 2955, 2921, 2866, 1611, 1583, 1564, 1554, 1515, 1488, 1463, 1432, 1398, 1361, 1320, 1301, 1262, 1245, 1214, 1188, 1168, 1145, 1125, 1084, 1037, 998, 971, 933, 886, 842, 810, 786, 766, 738, 693 cm$^{-1}$; $^1$H NMR (300 MHz, DMSO-$d_6$, 298 K): δ 9.23 (br s, 0.5H), 9.09 (br s, 0.5H), 9.02 (br s, 0.5H), 8.85 (br s, 0.5H), 7.95 (br s, 1H), 7.82 (br m, 1H), 7.41 (br d, 2H), 7.24 (t, $^3J$=7.6 Hz, 2H), 7.02 (d, $^3J$=7.6 Hz, 1H), 7.01 (br s, 1H), 6.59 (s, 1H), 4.64 (s, 2H), 2.87 (d, $^3J$=4.1 Hz, 3H), 2.23 (s, 6H) ppm; $^{13}$C NMR (75 MHz, DMSO-$d_6$): δ 165.9, 164.0, 163.7, 140.6, 139.9, 137.9, 137.1, 128.5, 123.2, 122.2, 120.4, 119.7, 117.7, 34.9, 27.2, 21.1 ppm; HRMS (EI) calcd. for $C_{19}H_{21}BrN_6$ (m/e): 412.1011. found: 412.1003.

25. Synthesis of 2-mexylamino-4-methylamino-6-(2-hydroxyethylamino)-1,3,5-triazine

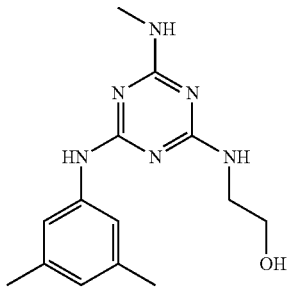 [SMILES: CNc1nc(NCCO)nc(Nc2cc(C)cc(C)c2)n1]

2-Mexylamino-4-methylamino-6-chloro-1,3,5-triazine (5.00 g, 19.0 mmol), and ethanolamine (5.70 mL, 5.79 g, 94.8 mmol) were added in THF (100 mL) in a round-bottomed flask equipped with a magnetic stirrer and a water-jacketed condenser, then the mixture was refluxed for 18 h. After the mixture was allowed to cool down to room temperature, 1M aqueous HCl was added, and both layers were separated. The organic layer was successively extracted with aq. NaHCO$_3$, $H_2O$ and brine, then the organic extracts were dried over Na$_2$SO$_4$, filtered, and the solvent was thoroughly evaporated under reduced pressure to yield 4.63 g of the title compound (16.1 mmol, 85%): $T_g$ 53° C.; FTIR ($CH_2Cl_2$/KBr) 3401, 3282, 3204, 3134, 3014, 2945, 2921, 2873, 1605, 1586, 1568, 1558, 1539, 1526, 1518, 1509, 1472, 1462, 1443, 1421, 1398, 1358, 1322, 1301, 1275, 1263, 1190, 1177, 1141, 1060, 997, 956, 938, 883, 869, 841, 810, 764, 750, 701, 688 cm$^{-1}$; $^1$H NMR (300 MHz, CDCl$_3$, 298 K): δ 7.52 (br s, 1H), 7.18 (s, 2H), 6.66 (s, 1H), 6.43 (br s, 1H), 5.56 (br s, 2H), 3.72 (t, $^3J$=4.7 Hz, 2H), 3.48 (br s, 2H), 2.87 (br s, 3H), 2.24 (s, 6H) ppm; $^{13}$C NMR (75 MHz, CDCl$_3$): δ 166.3, 166.3, 164.0, 138.8, 138.2, 124.6, 118.2, 62.8, 43.6, 27.5, 21.3 ppm; HRMS (EI) calcd. for $C_{14}H_{20}N_6O$ (m/e): 288.1699. found: 288.1692.

26. Synthesis of 2-mexylamino-4-methylamino-6-(3-hydroxypropylamino)-1,3,5-triazine

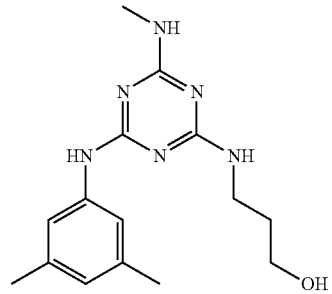 [SMILES: CNc1nc(NCCCO)nc(Nc2cc(C)cc(C)c2)n1]

The title compound was synthesized from 2-mexylamino-4-methylamino-6-chloro-1,3,5-triazine and 3-amino-1-propanol using a similar procedure to the one used in 25. Yield: 90%; $T_g$ 53° C.; FTIR ($CH_2Cl_2$/KBr) 3398, 3282, 3018, 2945, 2914, 2876, 1607, 1584, 1568, 1552, 1539, 1528, 1516, 1509, 1457, 1443, 1432, 1396, 1366, 1345, 1322, 1301, 1265, 1253, 1228, 1188, 1174, 1128, 1059, 1036, 995, 956, 923, 882, 840, 811, 737, 701, 689 cm$^{-1}$; $^1$H NMR (300 MHz, CDCl$_3$, 298 K): δ 7.56 (br s, 1H), 7.17 (s, 2H), 6.65 (s, 1H), 5.84 (br s, 1H), 5.74 (br s, 1H), 5.58 (br s, 1H), 3.54 (t, $^3$J=5.3 Hz, 2H), 3.48 (br s, 2H), 2.87 (br s, 3H), 2.24 (s, 6H), 1.62 (br s, 2H) ppm; $^{13}$C NMR (75 MHz, CDCl$_3$): δ 166.2, 166.2, 163.9, 138.7, 138.2, 124.6, 118.2, 57.9, 36.3, 32.8, 27.4, 21.3 ppm; HRMS (EI) calcd. for C$_{16}$H$_{22}$N$_6$O (m/e): 302.1855. found: 302.1849.

27. Synthesis of 2-mexylamino-4-methylamino-6-(carboxymethylamino)-1,3,5-triazine

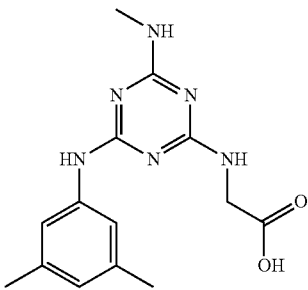 [SMILES: CNc1nc(NCC(=O)O)nc(Nc2cc(C)cc(C)c2)n1]

A solution of 2-mexylamino-4-methylamino-6-chloro-1,3,5-triazine (1.00 g, 3.79 mmol) in MeOH (20 mL) was added to a solution of glycine (1.42 g, 18.9 mmol) and NEt$_3$ (2.64 mL, 1.92 g, 18.9 mmol) in H$_2$O (10 mL) in a round-bottomed flask equipped with a magnetic stirrer. The flask was fitted with a water-jacketed condenser, then the mixture was refluxed for 18 h. The solvent was concentrated under vacuum to remove most MeOH, then AcOH (5 mL) was added. The precipitate was collected by filtration, washed with aqueous AcOH, water and acetone, and dried overnight in an oven to yield 1.01 g of the title compound (3.32 mmol, 88%): T$_m$ 264° C. (dec.); FTIR (CH$_2$Cl$_2$/KBr) 3363, 3293, 3219, 3097, 2968, 2923, 2864, 1695, 1674, 1623, 1583, 1559, 1521, 1491, 1458, 1435, 1378, 1316, 1293, 1276, 1263, 1246, 1197, 1170, 1153, 1140, 1121, 1103, 1071, 1024, 994, 966, 920, 886, 838, 809, 783, 765, 743, 709, 684 cm$^{-1}$; $^1$H NMR (300 MHz, DMSO-d$_6$, 298 K): δ 12.39 (br s, 1H), 8.85 (br d, 0.5H), 8.69 (br d, 0.5H), 7.40 (br m, 2H), 7.15-6.61 (br m, 2H), 6.53 (s, 1H), 3.91 (d, $^3$J=6.5 Hz, 2H), 2.76 (br s, 3H), 2.20 (s, 6H) ppm; $^{13}$C NMR (75 MHz, DMSO-d$_6$): δ 172.3, 166.0, 165.6, 164.1, 140.4, 137.0, 122.8, 117.2, 42.1, 27.2, 21.2 ppm; HRMS (EI) calcd. for C$_{14}$H$_{18}$N$_6$O$_2$ (m/e): 302.1491. found: 302.1483.

28. Synthesis of 2-mexylamino-4-methylamino-6-(2-aminoethylamino)-1,3,5-triazine

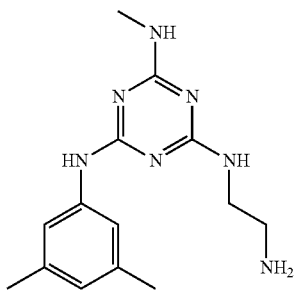 [SMILES: CNc1nc(NCCN)nc(Nc2cc(C)cc(C)c2)n1]

2-Mexylamino-4-methylamino-6-chloro-1,3,5-triazine (1.00 g, 3.79 mmol), and ethylenediamine (1.27 mL, 1.14 g, 18.9 mmol) were added in THF (20 mL) in a round-bottomed flask equipped with a magnetic stirrer and a water-jacketed condenser, then the mixture was refluxed for 18 h. After the mixture was allowed to cool down to room temperature, the volatiles were evaporated under vacuum. The residue was dissolved in 1M aqueous HCl, and the precipitate was removed by filtration and washed with H$_2$O. NaOH pellets were added to the filtrate until the pH became basic (>12), then the mixture was stirred for 30 min, at which time the solvent was decanted. The precipitated product was dissolved in CH$_2$Cl$_2$, dried over Na$_2$SO$_4$, filtered, and the solvent was thoroughly evaporated under reduced pressure to yield 0.768 g of the title compound (2.67 mmol, 71%): T$_g$ 58° C.; FTIR (CH$_2$Cl$_2$/KBr) 3402, 3275, 3195, 3134, 3013, 2945, 2920, 2866, 1587, 1566, 1549, 1520, 1440, 1396, 1358, 1323, 1300, 1266, 1252, 1189, 1159, 1113, 1065, 1037, 996, 972, 952, 934, 882, 842, 810, 735, 689 cm$^{-1}$; $^1$H NMR (300 MHz, CDCl$_3$, 298 K): δ 7.22 (s, 2H), 6.84 (br s, 1H), 6.66 (s, 1H), 5.55 (br s, 1H), 5.02 (br s, 1H), 3.47 (br s, 2H), 2.95 (d, $^3$J=5.3 Hz, 3H), 2.90 (t, $^3$J=5.3 Hz, 2H), 2.29 (s, 6H), 1.52 (br s, 2H) ppm; $^{13}$C NMR (75 MHz, CDCl$_3$): δ 166.6, 166.3, 164.3, 139.2, 138.1, 124.2, 117.9, 43.4, 41.5, 27.4, 21.4 ppm; HRMS (EI) calcd. for C$_{14}$H$_{21}$N$_7$ (m/e): 287.1858. found: 287.1851.

29. Reaction of 2-mexylamino-4-methylamino-6-(4-aminophenylamino)-1,3,5-triazine with 4-phenylazosalicylaldehyde

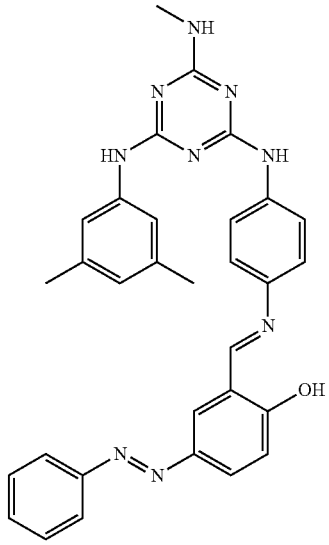 [SMILES: CNc1nc(Nc2ccc(/N=C/c3cc(/N=N/c4ccccc4)ccc3O)cc2)nc(Nc2cc(C)cc(C)c2)n1]

In a round-bottomed flask equipped with a magnetic stirrer, 2-mexylamino-4-methylamino-6-(4-aminophenylamino)-1,3,5-triazine (0.740 g, 2.21 mmol) and 4 phenylazosalicylaldehyde (0.500 g, 2.21 mmol) were dissolved in toluene (20 mL). The solution was sparged with N2 for 10 min, then a water-jacketed condenser was fitted on the flask and the mixture was refluxed for 12 h under nitrogen atmosphere. The volatiles were evaporated under reduced pressure, then the residue was redissolved in toluene and dried under vacuum. This process was repeated three times, after which the product was thoroughly dried to afford 1.16 g of the title compound (2.14 mmol, 97%): T$_g$ 97° C.; FTIR (CH$_2$Cl$_2$/KBr) 3407, 3275, 3187, 3041, 2922, 2853, 1616, 1601, 1573, 1504, 1420, 1356, 1287, 1238, 1185, 1108, 833, 808, 689 cm$^{-1}$; $^1$H NMR (400 MHz, DMSO-d$_6$, 298 K): δ 14.27 (br s, 1H), 9.38 (br s, 0.5H), 9.24 (br s, 0.5H), 9.16 (s, 1H), 9.07 (br s, 0.5H), 8.92 (br s, 0.5H), 8.26 (d, $^4$J=2.3 Hz, 1H), 7.98 (dd, $^3$J=8.8 Hz, $^4$J=2.3 Hz, 1H), 7.98 (br s, 2H), 7.86 (d, $^3$J=7.1 Hz, 2H), 7.58 (t, $^3$J=7.6 Hz, 2H), 7.52 (t, $^3$J=7.1 Hz, 1H), 7.44 (br m, 4H), 7.13 (d, $^3$J=8.8 Hz, 1H), 7.00 (br s, 1H), 6.61 (s, 1H), 2.89 (d, $^3$J=4.8 Hz, 3H), 2.26 (s, 6H) ppm; $^{13}$C NMR (100 MHz, DMSO-d$_6$): δ 166.0, 164.0, 163.8, 160.1, 151.9, 144.6, 140.1, 139.9, 137.0, 130.7, 129.2, 128.8, 128.0, 127.6, 126.6, 123.2, 122.1, 121.5, 120.2, 119.2, 117.8, 117.8, 27.2, 21.1 ppm; HRMS (EI) calcd. for $C_{31}H_{29}N_9O$ (m/e): 543.2495. found: 543.2511.

30. Condensation of 2-mexylamino-4-methylamino-6-(4-aminophenylamino)-1,3,5-triazine with 4-diphenylaminobenzaldehyde

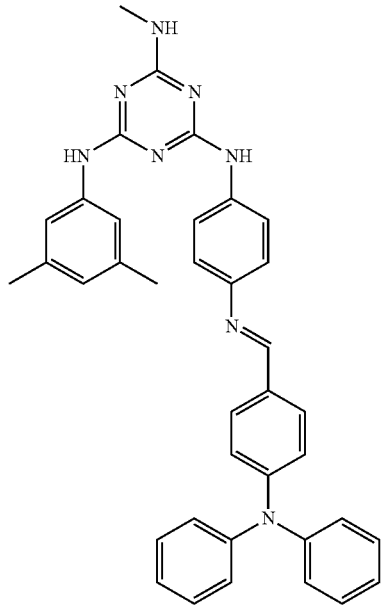 [SMILES: CNc1nc(Nc2ccc(/N=C/c3ccc(N(c4ccccc4)c4ccccc4)cc3)cc2)nc(Nc2cc(C)cc(C)c2)n1]

The title compound was synthesized from 2-mexylamino-4-methylamino-6-(4-aminophenylamino)-1,3,5-triazine and 4-diphenylaminobenzaldehyde using a similar procedure to the one used in 29. Yield: 91%; $T_g$ 93° C.; FTIR ($CH_2Cl_2$/KBr) 3408, 3279, 3187, 3087, 3062, 3033, 2946, 2916, 2864, 1621, 1606, 1588, 1558, 1505, 1492, 1419, 1400, 1360, 1330, 1317, 1296, 1283, 1235, 1197, 1187, 1171, 1113, 1075, 1029, 1012, 1000, 975, 941, 921, 887, 840, 808, 756, 736, 696 cm$^{-1}$; $^1$H NMR (300 MHz, $C_6D_6$, 298 K): δ 9.23 (br s, 0.5H), 9.09 (br s, 0.5H), 9.02 (br s, 0.5H), 8.88 (br s, 0.5H), 8.50 (s, 1H), 7.85 (br s, 2H), 7.78 (d, $^3J$=8.8 Hz, 2H), 7.43 (br d, 2H), 7.35 (t, $^3J$=7.6 Hz, 4H), 7.20 (d, $^3J$=8.8 Hz, 2H), 7.11 (m, 6H), 6.97 (d, $^3J$=8.8 Hz, 2H), 6.93 (br s, 1H), 6.58 (s, 1H), 2.86 (d, $^3J$=4.7 Hz, 3H), 2.23 (s, 6H) ppm; $^{13}$C NMR (75 MHz, $C_6D_6$): δ 166.0, 164.0, 163.8, 157.2, 149.7, 146.3, 145.2, 140.0, 138.4, 137.0, 129.6, 126.3, 125.1, 124.1, 123.1, 121.0, 120.8, 120.3, 117.7, 27.2, 21.1 ppm; HRMS (EI) calcd. for $C_{37}H_{34}N_8$ (m/e): 590.2906. found: 590.2931.

31. Condensation of 2-mexylamino-4-methylamino-6-(3-formylphenylamino)-1,3,5-triazine with 5-(4-aminophenyl)-10,15,20-triphenyl-meso-porphyrin

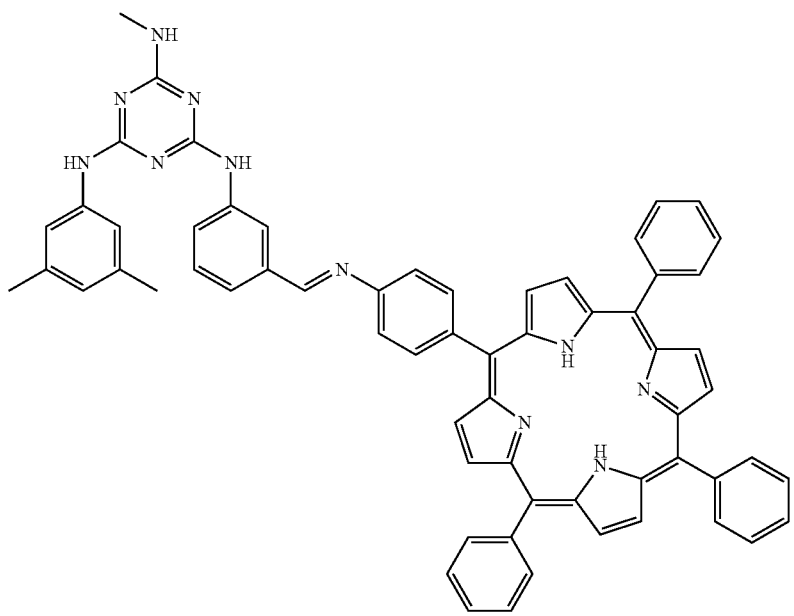 [SMILES: CNc1nc(Nc2cc(C)cc(C)c2)nc(Nc2cccc(/C=N/c3ccc(-c4c5nc(c(-c6ccccc6)c6ccc([nH]6)c(-c6ccccc6)c6nc(c(-c7ccccc7)c7ccc4[nH]7)C=C6)C=C5)cc3)c2)n1]

The title compound was synthesized from 2-mexylamino-4-methylamino-6-(3-formylphenylamino)-1,3,5-triazine and 5-(4-aminophenyl)-10,15,20-triphenyl-meso-porphyrin using a similar procedure to the one used in 29. Yield: 97%; $T_g$ 100° C.; FTIR (CH$_2$Cl$_2$/KBr) 3409, 3317, 3101, 3054, 3024, 2952, 2929, 2907, 2864, 1619, 1596, 1575, 1556, 1514, 1474, 1430, 1400, 1350, 1322, 1299, 1264, 1244, 1221, 1215, 1185, 1177, 1155, 1072, 1032, 1001, 980, 966, 845, 801, 734, 701 cm$^{-1}$; $^1$H NMR (300 MHz, DMSO-d$_6$, 298 K): δ 9.46 (br s, 0.5H), 9.32 (brs, 0.5H), 9.08 (brs, 0.5H), 8.91 (br s, 0.5H), 8.84 (s, 1H), 8.80 (m, 8H), 8.46 (br d, 0.5H), 8.30 (br d, 0.5H), 8.15 (d, $^3$J=5.9 Hz, 6H), 8.10 (m, 1H), 8.09 (d, $^3$J=7.3 Hz, 2H), 7.75 (m, 9H), 7.49 (m, 2H), 7.44 (m, 3H), 7.03 (br s, 1H), 6.56 (s, 1H), 2.88 (d, $^3$J=4.1 Hz, 3H), 2.20 (s, 6H), −2.85 (s, 2H) ppm; $^{13}$C NMR (75 MHz, DMSO-d$_6$): δ 166.0, 164.1, 163.8, 161.6, 151.0, 141.1, 139.9, 138.6, 137.0, 136.2, 135.0, 134.1, 131.1, 128.7, 127.9, 126.8, 125.4, 123.2, 122.4, 121.7, 120.6, 119.9, 119.4, 117.8, 27.2, 21.1 ppm; HRMS (EI) calcd. for C$_{63}$H$_{49}$N$_{11}$ (m/e): 960.4251. found: 960.4238.

32. Reaction of 2-mexylamino-4-methylamino-6-(4-mercaptophenylamino)-1,3,5-triazine with 4-(triphenylsilyl)benzyl bromide

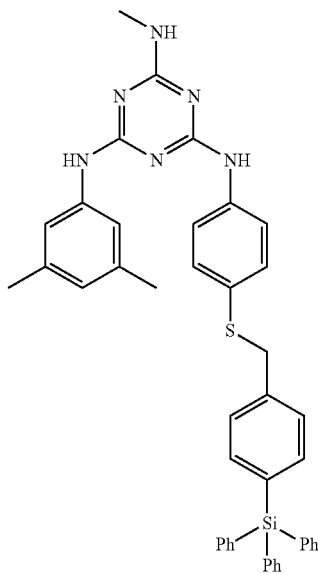 [SMILES: CNc1nc(Nc2ccc(SCc3ccc([Si](c4ccccc4)(c4ccccc4)c4ccccc4)cc3)cc2)nc(Nc2cc(C)cc(C)c2)n1]

In a round-bottomed flask equipped with a magnetic stirrer, 2-mexylamino-4-methylamino-6-(4-mercaptophenylamino)-1,3,5-triazine (0.0820 g, 0.233 mmol) and 4-(triphenylsilyl)benzyl bromide (0.100 g, 0.233 mmol) were dissolved in DMF (2 mL). K$_2$CO$_3$ (0.0320 g, 0.233 mmol) was added, and the mixture was stirred at ambient temperature for 16 h, at which point the reaction mixture was poured in water. The precipitate was collected by filtration, abundantly washed with water. The crude product was dissolved in CH$_2$Cl$_2$, extracted with 1M aq. NaOH, dried over Na$_2$SO$_4$, filtered, and the volatiles were thoroughly evaporated under reduced pressure, giving 0.147 g pure title compound (0.210 mmol, 90%): $T_g$ 88° C.; FTIR (CH$_2$Cl$_2$/KBr) 3450, 3417, 3055, 2987, 2927, 2855, 1573, 1554, 1497, 1422, 1399, 1352, 1266, 1181, 1158, 1109, 1029, 1021, 997, 984, 896, 810 cm$^{-1}$; $^1$H NMR (300 MHz, DMSO-d$_6$, 298 K): δ 9.18 (br s, 0.5H), 9.04 (br s, 0.5H), 9.01 (br s, 0.5H), 8.84 (br s, 0.5H), 7.74 (br s, 2H), 7.44 (m, 15H), 7.37 (m, 6H), 7.22 (d, $^3$J=8.8 Hz, 2H), 6.91 (br s, 1H), 6.57 (s, 1H), 4.15 (s, 2H), 2.82 (br s, 3H), 2.20 (s, 6H) ppm; $^{13}$C NMR (75 MHz, DMSO-d$_6$): δ 165.9, 164.1, 163.7, 139.9, 139.8, 139.3, 137.0, 135.7, 135.6, 133.4, 131.8, 130.6, 129.7, 128.5, 128.0, 126.6, 123.1, 120.1, 117.7, 38.4, 27.2, 21.1 ppm; HRMS (EI) calcd. for C$_{43}$H$_{40}$N$_6$SiS (m/e): 700.2804. found: 700.2821.

33. Reaction of 2-mexylamino-4-methylamino-6-(4-mercaptophenylamino)-1,3,5-triazine with 5-chloromethyl-8-hydroxyquinoline

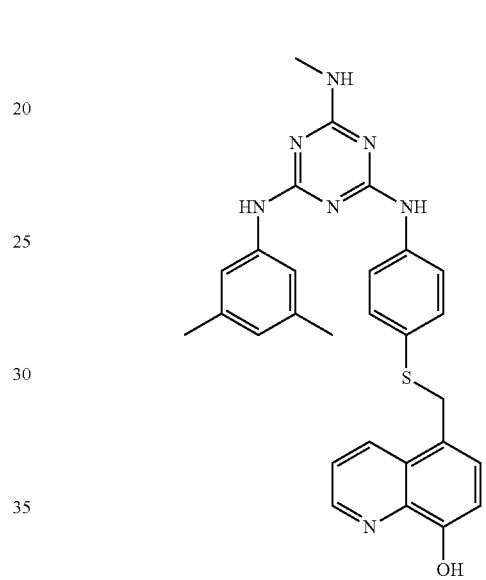

In a round-bottomed flask equipped with a magnetic stirrer, 5-chloromethyl-8-hydroxyquinoline hydrochloride (0.253 g, 1.10 mmol) and N,N-diisopropylethylamine (0.366 mL, 0.271 g, 2.10 mmol) were successively dissolved in CHCl$_3$ (5 mL). The flask was placed in an ice bath, then 2-mexylamino-4-methylamino-6-(4-mercaptophenylamino)-1,3,5-triazine (0.352 g, 1.00 mmol) was added, and the mixture was stirred at ambient temperature for 16 h. CHCl$_3$ and 1M aqueous NaOH were added, then both layers were separated. The organic layer was extracted with 5% aqueous acetic acid until the yellow color disappeared, aqueous NaHCO$_3$ and brine, dried over Na$_2$SO$_4$, filtered, then the volatiles were thoroughly evaporated under vacuum to yield 0.423 g title compound (0.830 mmol, 83%): $T_g$ 91° C.; FTIR (CH$_2$Cl$_2$/KBr) 3378, 3284, 3185, 3102, 3046, 3028, 2956, 2919, 2869, 1621, 1606, 1575, 1566, 1556, 1542, 1533, 1525, 1506, 1474, 1443, 1429, 1419, 1401, 1374, 1322, 1302, 1281, 1268, 1231, 1180, 1156, 1111, 1090, 1076, 1037, 1012, 978, 957, 886, 833, 809, 786, 737, 701 cm$^{-1}$; $^1$H NMR (300 MHz, DMSO-d$_6$, 298 K): δ 9.79 (br s, 1H), 9.26 (br s, 0.5H), 9.12 (br s, 0.5H), 9.06 (br s, 0.5H), 8.91 (br s, 0.5H), 8.85 (d, $^4$J=4.1 Hz, 1H), 8.57 (d, $^3$J=8.2 Hz, 1H), 7.89, 7.79 (br d, 2H), 7.58 (dd, $^3$J=8.2 Hz, $^4$J=4.1 Hz, 1H), 7.44 (br s, 1H), 7.39 (br s, 2H), 7.23 (br d, 2H), 6.98 (br s, 1H), 6.94 (d, $^3$J=8.2 Hz, 1H), 6.57 (s, 1H), 4.50 (s, 2H), 2.87 (d, $^3$J=4.1 Hz, 3H), 2.21 (s, 6H) ppm; $^{13}$C NMR (75 MHz, DMSO-d$_6$): δ 166.0, 164.1, 163.9, 152.8, 147.7, 140.9, 140.0, 139.6, 138.8, 137.1, 133.0, 131.5, 130.3, 128.6, 126.8, 123.3, 121.5, 120.1, 117.8, 110.2, 36.1, 27.3, 21.1 ppm; HRMS (EI) calcd. for $C_{28}H_{27}N_7OS$ (m/e): 509.1998. found: 509.2018.

34. Reaction of 2-mexylamino-4-methylamino-6-(4-mercaptophenylamino)-1,3,5-triazine with 4-chloromethylsalicylaldehyde

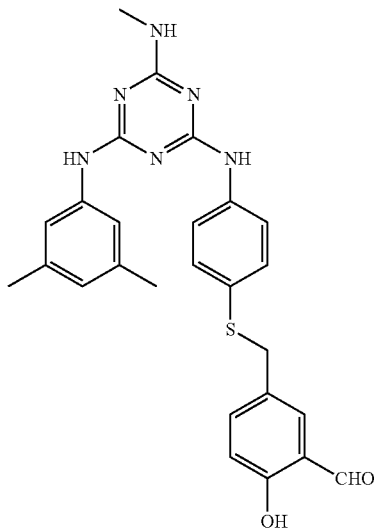 [SMILES: CNc1nc(Nc2ccc(SCc3ccc(O)c(C=O)c3)cc2)nc(Nc2cc(C)cc(C)c2)n1]

The title compound was synthesized from 2-mexylamino-4-methylamino-6-(4-aminophenylamino)-1,3,5-triazine and 4-chloromethylsalicylaldehyde using a similar procedure to the one used in 33. Yield: 88%; $T_g$ 84° C.; FTIR ($CH_2Cl_2$/KBr) 3390, 3282, 3190, 3050, 3023, 2949, 2920, 2857, 1657, 1610, 1573, 1555, 1538, 1508, 1492, 1417, 1401, 1362, 1322, 1301, 1284, 1264, 1234, 1210, 1182, 1149, 1089, 1036, 1012, 977, 957, 943, 892, 835, 809, 770, 737, 704, 691, 675 cm$^{-1}$; $^1$H NMR (300 MHz, $C_6D_6$, 298 K): δ 10.66 (s, 1H), 10.21 (s, 1H), 9.18 (br s, 0.5H), 9.03 (br s, 1H), 8.86 (br s, 0.5H), 7.84, 7.73 (br d, 2H), 7.55 (d, $^4J$=1.8 Hz, 1H), 7.42 (dd, $^3J$=8.8 Hz, $^4J$=1.8 Hz, 1H), 7.37 (br d, 2H), 7.20 (d, $^3J$=8.2 Hz, 2H), 6.96 (br s, 1H), 6.91 (d, $^3J$=8.8 Hz, 1H), 6.59 (s, 1H), 4.09 (s, 2H), 2.83 (d, $^3J$=4.1 Hz, 3H), 2.22 (s, 6H) ppm; $^{13}$C NMR (75 MHz, $C_6D_6$): δ 191.1, 166.0, 164.0, 163.8, 159.7, 139.9, 139.4, 137.1, 136.7, 130.8, 130.2, 128.8, 124.8, 123.2, 121.9, 120.1, 117.7, 117.2, 37.6, 27.2, 21.1 ppm; HRMS (EI) calcd. for $C_{26}H_{26}N_6O_2S$ (m/e): 486.1838. found: 486.1847.

35. Reaction of the Product of Example 34 with trans-1,2-diaminocyclohexane

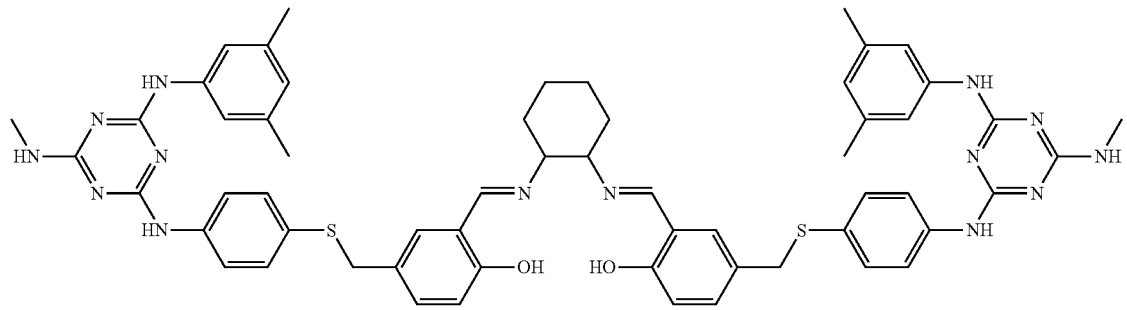

In a round-bottomed flask equipped with a magnetic stirrer and a water-jacketed condenser, the product of Example 34 (0.852 g, 1.75 mmol) was dissolved in EtOH/THF (1:1, 10 mL). Trans-1,2-diaminocyclohexane (0.100 g, 0.876 mmol) was added, then the mixture was refluxed 3 h. The solvent was then thoroughly evaporated under reduced pressure to yield 0.838 g of the title Salen derivative (0.717 mmol, 91%): $T_g$ 141° C.; FTIR ($CH_2Cl_2$/KBr) 3395, 3273, 3175, 3023, 2933, 2858, 1644, 1623, 1570, 1557, 1525, 1512, 1499, 1490, 1414, 1397, 1356, 1322, 1300, 1277, 1228, 1177, 1154, 1116, 1089, 1057, 1030, 1010, 991, 963, 934, 902, 867, 822, 806, 781, 735, 717, 687, 667 cm$^{-1}$; $^1$H NMR (300 MHz, DMSO-$d_6$, 298 K): δ 13.25 (br s, 2H), 9.36 (br s, 1H), 9.20 (br s, 1H), 9.05 (br s, 1H), 8.89 (br s, 1H), 8.39 (s, 2H), 7.85, 7.72 (br d, 4H), 7.39 (br s, 2H), 7.36 (br s, 4H), 7.22 (br s, 2H), 7.17 (br s, 4H), 6.93 (br s, 2H), 6.71 (d, $^3J$=8.2 Hz, 2H), 6.57 (s, 2H), 4.00 (s, 4H), 3.37 (br m, 2H), 2.84 (br s, 6H), 2.20 (br s, 12H), 1.74 (br m, 4H), 1.55 (br m, 2H), 1.40 (br m, 2H) ppm; $^{13}$C NMR (75 MHz, DMSO-$d_6$): δ 166.0, 164.6, 164.0, 163.8, 159.3, 139.9, 139.2, 137.0, 132.7, 131.5, 130.6, 130.2, 127.7, 126.8, 123.2, 120.2, 117.7, 116.3, 71.1, 37.8, 32.4, 27.2, 23.6, 21.1 ppm; HRMS (MALDI) calcd. for $C_{58}H_{63}N_{14}O_2S_2$ (m/e): 1051.4689. found: 1051.4694.

36. Reaction of 2-mexylamino-4-methylamino-6-(4-mercaptophenylamino)-1,3,5-triazine with 1-(chloromethyldimethylsilyl)pyrene

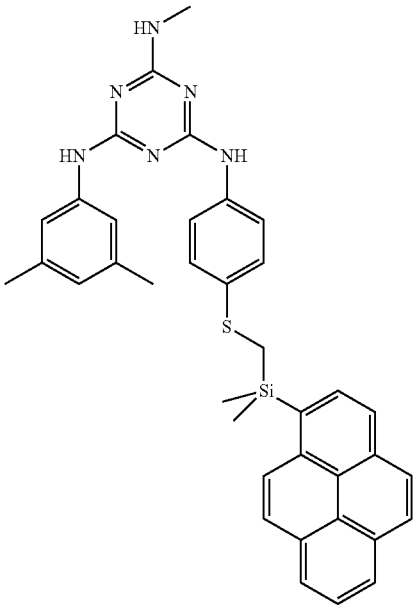 [SMILES: CNc1nc(Nc2ccc(SC[Si](C)(C)c3ccc4ccc5cccc6ccc3c4c56)cc2)nc(Nc2cc(C)cc(C)c2)n1]

2-Mexylamino-4-methylamino-6-(4-mercaptophenylamino)-1,3,5-triazine (0.254 g, 0.719 mmol), 1-(chloromethyldimethylsilyl)pyrene (0.222 g, 0.719 mmol) and potassium iodide (0.119 g, 0.719 mmol) were dissolved in acetone (5 mL) in a round-bottomed flask equipped with a magnetic stirrer. $K_2CO_3$ (0.199 g, 1.44 mmol) was added, the mixture was sparged with $N_2$ for 15 min, then a water-jacketed condenser was fitted on the flask and the mixture was refluxed 18 h under inert atmosphere. After cooling down to ambient temperature, $H_2O$ was added, and the precipitate was collected by filtration and washed with $H_2O$ and hot hexanes. The precipitate was redissolved in $CH_2Cl_2$ and purified on a short silica plug using $CH_2Cl_2$ then AcOEt as eluent to yield 0.309 g of the title compound after complete evaporation of the volatiles (0.495 mmol, 69%). $T_g$ 83° C.; FTIR ($CH_2Cl_2$/KBr) 3406, 3277, 3177, 3044, 2956, 2861, 1567, 1495, 1415, 1399, 1360, 1323, 1302, 1284, 1262, 1252, 1236, 1216, 1182, 1146, 1130, 1083, 1033, 1012, 974, 892, 848, 838, 809, 737, 717, 705, 647 cm$^{-1}$; $^1$H NMR (300 MHz, DMSO-$d_6$, 298 K): δ 9.13 (br s, 0.5H), 8.99 (br s, 1H), 8.84 (br s, 0.5H), 8.42-8.05 (m, 9H), 7.73 (br s, 2H), 7.38 (br d, 2H), 7.22 (d, $^3$J=8.2 Hz, 2H), 6.90 (br s, 1H, 6.54 (s, 1H), 2.85 (d, $^3$J=4.1 Hz, 3H), 2.79 (s, 2H), 2.20 (s, 6H), 0.70 (s, 6H) ppm; $^{13}$C NMR (75 MHz, DMSO-$d_6$): δ 166.0, 164.0, 163.8, 130.0, 137.9, 137.0, 135.1, 132.5, 132.2, 131.9, 130.9, 130.6, 130.2, 130.0, 128.0, 127.5, 127.3, 127.0, 126.1, 125.3, 124.1, 123.9, 123.7, 123.1, 120.5, 120.1, 117.6, 27.2, 21.1, 18.5, −1.32 ppm; HRMS (EI) calcd. for $C_{37}H_{36}N_6SSi$ (m/e): 624.2491. found: 624.2482.

37. Reaction of 2-mexylamino-4-methylamino-6-[4-(2,3-dihydroxypropoxyl)phenylamino]-1,3,5-triazine with 4-(triphenylsilyl)phenylboronic acid

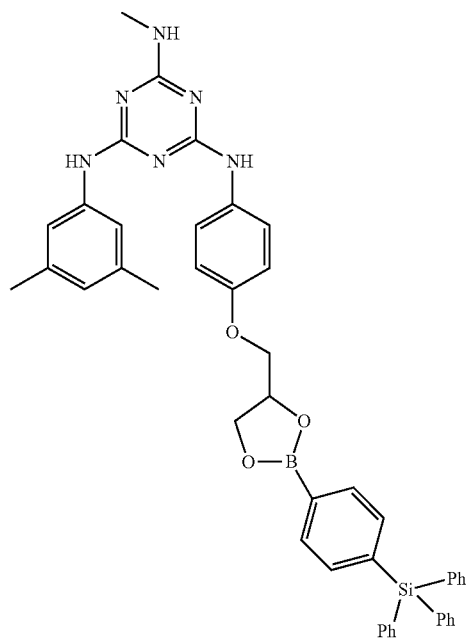 [SMILES: CNc1nc(Nc2ccc(OCC3COB(c4ccc([Si](c5ccccc5)(c5ccccc5)c5ccccc5)cc4)O3)cc2)nc(Nc2cc(C)cc(C)c2)n1]

In a round-bottomed flask equipped with a magnetic stirrer, 2-mexylamino-4-methylamino-6-[4-(2,3-dihydroxypropoxy)phenylamino]-1,3,5-triazine (0.0940 g, 0.230 mmol) and 4-(triphenylsilyl)phenylboronic acid (0.0890 g, 0.230 mmol) were dissolved in toluene/THF (1:1, 5 mL). The solution was sparged with N2 for 10 min, then a water-jacketed condenser was fitted on the flask and the mixture was refluxed for 12 h under nitrogen atmosphere. The volatiles were evaporated under reduced pressure, then the residue was redissolved in toluene and dried under vacuum. This process was repeated three times, after which the product was thoroughly dried to afford 0.167 g of the title compound (0.221 mmol, 96%): $T_g$ 83° C.; FTIR ($CH_2Cl_2$/KBr) 3406, 3280, 3191, 3134, 3068, 3049, 3022, 2958, 2919, 1600, 1573, 1505, 1428, 1400, 1369, 1323, 1302, 1264, 1218, 1187, 1178, 1110, 1101, 1080, 1023, 998, 982, 920, 829, 809, 707, 649 cm$^{-1}$; $^1$H NMR (400 MHz, $C_6D_6$, 298 K): δ 8.16 (d, 3J=7.8 Hz, 2H), 7.82 (d, $^3$J=7.6 Hz, 2H), 7.68 (d, $^3$J=6.3 Hz, 6H), 7.41 (br d, 2H), 7.19 (m, 13H), 6.73 (br s, 2H), 6.58 (s, 1H), 5.30 (br s, 0.5H), 5.07 (br s, 0.5H), 4.37 (m, 1H), 3.94 (d, $^3$J=7.1 Hz, 2H), 3.58 (m, 2H), 2.66 (d, $^3$J=3.5 Hz, 3H), 2.18 (s, 6H) ppm; $^1$H NMR (300 MHz, DMSO-$d_6$, 298 K): δ 9.00 (br s, 0.5H), 8.95 (br s, 0.5H), 8.84 (br s, 1H), 7.82 (d, $^3$J=7.6 Hz, 2H), 7.66 (br s, 2H), 7.55 (d, $^3$J=7.0 Hz, 2H), 7.44 (m, 17H), 6.88 (d, $^3$J=8.8 Hz, 2H), 6.88 (br s, 1H), 6.54 (s, 1H), 4.95 (br s, 1H), 4.48 (t, $^3$J=8.8 Hz, 1H), 4.22 (t, $^3$J=8.2 Hz, 1H), 4.13 (m, 2H), 2.84 (d, $^3$J=2.3 Hz, 3H), 2.20 (s, 6H) ppm (traces of hydrolyzed products are also present in DMSO-$d_6$); $^{13}$C NMR (75 MHz, $C_6D_6$): δ 167.1, 165.1, 164.9, 155.0, 139.6, 138.9, 138.6, 138.2, 136.9, 136.4, 134.8, 134.5, 133.4, 129.9, 128.3, 124.8, 122.7, 118.8, 115.0, 75.6, 70.0, 68.3, 27.5, 21.5 ppm; HRMS (EI) calcd. for $C_{45}H_{43}BN_6O_3Si$ (m/e): 754.3259. found: 754.3243.

38. Huisgen cycloaddition of 2-mexylamino-4-methylamino-6-(4-azidophenylamino)-1,3,5-triazine with 4-(triphenylsilyl)phenylacetylene

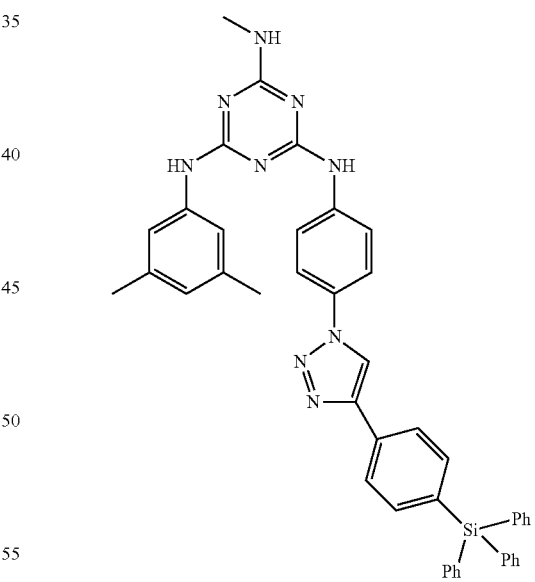

A solution of 2-mexylamino-4-methylamino-6-(4-azidophenylamino)-1,3,5-triazine (0.0750 g, 0.208 mmol) and 4-(triphenylsilyl)phenylacetylene (0.0750 g, 0.208 mmol) in THF (5 mL) in a round-bottomed flask equipped with a magnetic stirrer was sparged with nitrogen for 15 min. A deoxygenated solution of $CuSO_4$ pentahydrate (0.005 g, 0.0208 mmol), ascorbic acid (0.007 g, 0.0416 mmol) and $NaHCO_3$ (0.004 g, 0.0416 mmol) in $H_2O$ (3 mL) was added, and the mixture was vigorously stirred at ambient temperature for 18 h. Upon complete consumption of the starting materials (by TLC; 3:1 AcOEt/acetone) H$_2$O and hexanes were added to the mixture and the precipitate was collected by filtration and washed with H$_2$O and hexanes. The precipitate was redissolved in AcOEt, successively extracted with aq. 1M HCl, aq. NaHCO$_3$ and brine, dried over Na$_2$SO$_4$, filtered, then the volatiles were thoroughly removed under vacuum to yield 0.138 g of the title compound (0.191 mmol, 92%): T$_g$ 103° C.; FTIR (CH$_2$Cl$_2$/KBr) 3399, 3283, 3191, 3130, 3068, 3049, 3015, 2949, 2916, 2866, 1605, 1581, 1557, 1518, 1505, 1428, 1359, 1323, 1301, 1234, 1110, 1037, 1019, 992, 836, 809, 700 cm$^{-1}$; $^1$H NMR (400 MHz, DMSO-d$_6$, 298 K): δ 9.45 (br s, 0.5H) ppm, 9.31 (br s, 0.5H), 9.23 (s, 1H), 9.09 (br s, 0.5H), 8.93 (br s, 0.5H), 8.05 (br s, 2H), 8.00 (d, $^3$J=8.2 Hz, 2H), 7.80 (br d, 2H), 7.60 (d, $^3$J=8.2 Hz, 2H), 7.50 (m, 15H), 7.39 (br d, 2H), 7.02 (br s, 1H), 6.61 (s, 1H), 2.86 (d, $^3$J=4.1 Hz, 3H), 2.24 (s, 6H); $^{13}$C NMR (75 MHz, DMSO-d$_6$): δ 166.0, 164.0, 163.8, 146.7, 141.0, 139.9, 137.1, 136.4, 135.7, 134.4, 133.3, 131.7, 130.2, 129.8, 128.1, 124.9, 123.3, 120.2, 120.1, 119.7, 117.8, 27.2, 21.1 ppm; HRMS (ESI) calcd. for C$_{44}$H$_{40}$N$_9$Si (m/e): 722.3163. found: 722.3175.

39. Reaction of 2-mexylamino-4-methylamino-6-(4-carboxyphenylamino)-1,3,5-triazine with 4-[bis(4-dimethylaminophenyl)methyl]aniline (4-amino leuco Malachite Green)

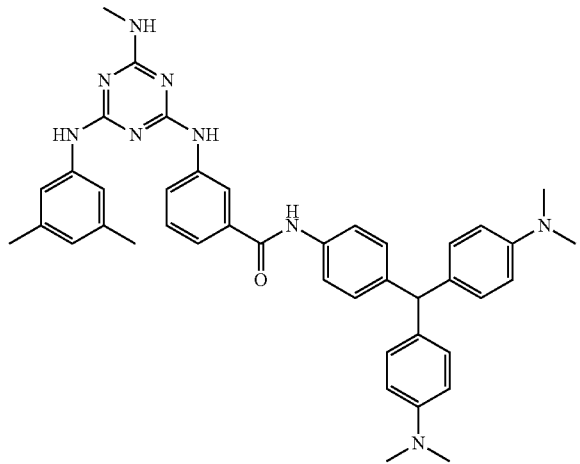

2-Mexylamino-4-methylamino-6-(4-carboxyphenylamino)-1,3,5-triazine (0.232 g, 0.637 mmol) and N,N-diisopropylethylamine (0.221 mL, 0.164 g, 1.27 mmol) were dissolved in anhydrous DMF (1 mL) in a dry round-bottomed flask equipped with a magnetic stirrer. The flask was placed in an ice bath, then 1-hydroxybenzotriazole (0.094 g, 0.695 mmol) and HBTU (0.264 g, 0.695 mmol) were added and the mixture was stirred at 0° C. for 20 min, at which point 4-[bis(4-dimethylaminophenyl)methyl]aniline (0.200 g, 0.579 mmol) was added and the mixture was stirred at ambient temperature for 18 h under inert atmosphere. The solution was poured in aqueous Na$_2$CO$_3$ and stirred at ambient temperature for 30 min, then the precipitate was collected by filtration and washed with aqueous Na$_2$CO$_3$ and H$_2$O. The precipitate was redissolved in CH$_2$Cl$_2$ to give a turquoise-blue solution which was discoloured by addition of NaBH$_4$ (0.01 g) and stirring. H$_2$O was added, and both layers were separated. The aqueous layer was extracted with CH$_2$Cl$_2$, then the combined organic extracts were dried over Na$_2$SO$_4$, filtered, and the volatiles were thoroughly evaporated under reduced pressure to give 0.284 g of the title compound (0.410 mmol, 71%): T$_g$ 105° C.; FTIR (CH$_2$Cl$_2$/KBr) 3390, 3292, 3193, 3094, 3028, 2948, 2916, 2882, 2857, 2800, 1659, 1612, 1581, 1554, 1516, 1482, 1428, 1406, 1350, 1322, 1264, 1222, 1202, 1184, 1163, 1132, 1101, 1060, 1039, 1019, 998, 976, 948, 883, 843, 808, 788, 738, 702, 688 cm$^{-1}$; $^1$H NMR (300 MHz, DMSO-d$_6$, 298 K): δ 10.19 (s, 1H), 9.37 (br s, 0.5H), 9.21 (br s, 0.5H), 9.06 (br s, 0.5H), 8.89 (br s, 0.5H), 8.19 (br d, 1H), 8.10 (br m, 1H), 7.69 (d, $^3$J=8.2 Hz, 2H), 7.54 (d, $^3$J=7.6 Hz, 1H), 7.45 (br d, 2H), 7.40 (t, $^3$J=7.6 Hz, 1H), 7.05 (d, $^3$J=8.2 Hz, 2H), 7.00 (br s, 1H), 6.92 (d, $^3$J=8.8 Hz, 4H), 6.64 (d, $^3$J=8.8 Hz, 4H), 6.56 (s, 1H), 5.28 (s, 1H), 2.87 (d, $^3$J=3.5 Hz, 3H), 2.83 (s, 12H), 2.21 (s, 6H) ppm; $^{13}$C NMR (75 MHz, DMSO-d$_6$): δ 166.1, 165.7, 164.2, 163.9, 148.6, 140.53, 140.46, 140.0, 137.1, 137.0, 135.6, 132.3, 129.3, 129.2, 128.8, 128.2, 123.1, 120.5, 120.1, 119.4, 117.6, 112.3, 53.7, 40.2, 27.3, 21.1 ppm; HRMS (EI) calcd. for C$_{42}$H$_{45}$N$_9$O (m/e): 691.3747. found: 691.3766.

40. Reaction of 2-mexylamino-4-methylamino-6-(3-bromomethylphenylamino)-1,3,5-triazine with tetra-tert-butylcalix[4]arene

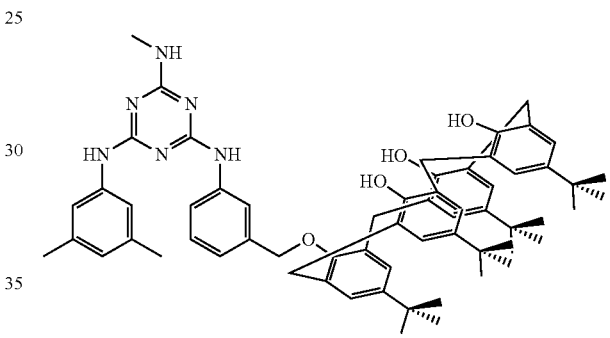

Tetra-tert-butylcalix[4]arene (0.179 g, 0.242 mmol) and K$_2$CO$_3$ (0.066 g, 0.484 mmol) were added in DMF (2 mL) in a round-bottomed flask equipped with a magnetic stirrer. The mixture was gently heated until the calixarene had completely dissolved. 2-Mexylamino-4-methylamino-6-(3-bromomethylphenylamino)-1,3,5-triazine (0.100 g, 0.242 mmol) was added, and the mixture was stirred 3 d at ambient temperature, then poured in 0.1 M aqueous HCl. The precipitate was collected by filtration and abundantly washed with H$_2$O. The crude product was redissolved in CH$_2$Cl$_2$, extracted with aqueous NaHCO$_3$ and brine, then the organic layer was dried over Na$_2$SO$_4$, filtered, and the solvent was evaporated. The product was purified on a short silica plug using CH$_2$Cl$_2$ then CH$_2$Cl$_2$/acetone 4:1 as eluent, then melted under vacuum to remove all volatiles to give 0.144 g of the title compound (0.147 mmol, 61%). T$_g$ 142° C.; FTIR (CH$_2$Cl$_2$/KBr) 3420, 3278, 3049, 3023, 2959, 2905, 2869, 1584, 1557, 1519, 1509, 1485, 1430, 1394, 1362, 1320, 1298, 1264, 1243, 1203, 1187, 1118, 1097, 1027, 996, 970, 945, 913, 874, 837, 808, 783, 736, 701, 687 cm$^{-1}$; $^1$H NMR (300 MHz, DMSO-d$_6$, 298 K): δ 9.20 (br s, 0.5H), 9.06 (br s, 0.5H), 8.97 (br s, 0.5H), 8.80 (br s, 0.5H), 8.51 (br s, 1H), 8.30 (br s, 2H), 7.97 (br s, 1H), 7.88 (br m, 1H), 7.40 (br d, 2H), 7.28 (br t, 1H), 7.20 (br d, 1H), 7.06 (br d, 2H), 6.97 (br s, 3H), 6.92 (br d, 2H), 6.84 (br d, 2H), 6.56 (s, 1H), 4.93 (s, 2H), 3.96 (br s, 4H), 3.79 (br s, 4H), 2.81 (br s, 3H), 2.21 (s, 6H), 1.11 (s, 18H), 1.03 (s, 9H), 0.94 (s, 9H) ppm; $^{13}$C NMR (75 MHz, DMSO-d$_6$): δ 165.9, 164.1, 163.8, 151.9, 149.8, 149.1, 145.3, 141.3, 140.5, 140.0, 137.4, 137.0, 132.7, 128.3, 127.1, 126.9, 126.6, 126.3, 125.7, 125.2, 124.7, 124.3, 123.1, 121.2, 119.4, 117.7, 74.8, 33.6, 33.4, 31.2, 31.0, 27.2, 21.1 ppm; HRMS (EI) calcd. for $C_{63}H_{76}N_6O_4$ (m/e): 980.5928. found: 980.5957.

41. Reaction of 2-mexylamino-4-methylamino-6-(4-mercaptophenylamino)-1,3,5-triazine with N,N'-bis(2,6-diisopropylphenyl)-1,7-dibromo-3,4,9,10-perylenetetracarboxylic diimide (disubstitution)

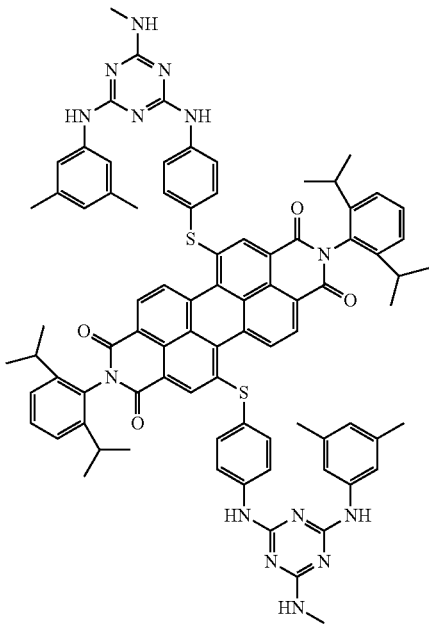 [SMILES: CNc1nc(Nc2ccc(Sc3cc4c5c(ccc6c7c(Sc8ccc(Nc9nc(NC)nc(Nc%10cc(C)cc(C)c%10)n9)cc8)cc8c9c(ccc(c3c56)c97)C(=O)N(c3c(C(C)C)cccc3C(C)C)C8=O)C(=O)N(c3c(C(C)C)cccc3C(C)C)C4=O)cc2)nc(Nc2cc(C)cc(C)c2)n1]

In a round-bottomed flask equipped with a magnetic stirrer, $K_2CO_3$ (0.796 g, 5.76 mmol) and CTAB (0.05 g) were dissolved in $H_2O$ (25 mL). Toluene (50 mL) was added, then the biphasic mixture was sparged with nitrogen for 15 min. 2-mexylamino-4-methylamino-6-(4-mercaptophenylamino)-1,3,5-triazine (0.507 g, 1.44 mmol) and N,N'-bis(2,6-diisopropylphenyl)-1,7-dibromo-3,4,9,10-perylenetetracarboxylic diimide (0.5 g, 0.576 mmol) were then added, and the mixture was stirred at 80° C. for 16 h under inert atmosphere. The dark blue precipitate that formed was collected by filtration and washed with $H_2O$ and $CH_2Cl_2$, then thoroughly dried under vacuum to give 0.664 g pure title compound (0.470 mmol, 82%): $T_g$ 211° C.; FTIR ($CH_2Cl_2$/KBr) 3411, 3324, 3195, 3075, 2962, 2921, 2870, 1699, 1664, 1606, 1594, 1583, 1568, 1553, 1511, 1501, 1492, 1456, 1442, 1427, 1412, 1389, 1365, 1335, 1312, 1295, 1263, 1248, 1236, 1213, 1197, 1184, 1148, 1095, 1056, 1038, 1012, 998, 970, 937, 922, 885, 856, 836, 809, 795, 742, 715, 702, 662 cm$^{-1}$; $^1$H NMR (300 MHz, DMSO-$d_6$, 298 K): δ 9.52 (br s, 1H), 9.39 (br s, 1H), 9.09 (br s, 1H), 8.93 (br s, 1H), 8.73 (br s, 4H), 8.29 (br s, 2H), 8.00 (br s, 4H), 7.50 (br d, 4H), 7.43 (br t, 2H), 7.33 (br m, 8H), 7.00 (br s, 2H), 6.54 (s, 2H), 2.82 (br s, 6H), 2.70 (m, 4H), 2.14 (s, 12H), 1.03 (br d, 24H) ppm; $^{13}$C NMR (75 MHz, DMSO-$d_6$): δ 166.0, 164.0, 163.7, 162.84, 162.76, 145.3, 142.8, 140.2, 139.7, 137.0, 135.6, 131.9, 131.3, 130.5, 129.2, 128.7, 128.4, 127.9, 125.4, 123.7, 123.2, 122.0, 121.3, 121.2, 120.6, 117.8, 28.5, 27.2, 23.6, 21.0 ppm; HRMS (MALDI, MH$^+$) calcd. for $C_{84}H_{79}N_{14}O_4S_2$ (m/e): 1411.5850. found: 1411.5866.

42. Reaction of 2-mexylamino-4-methylamino-6-(4-mercaptophenylamino)-1,3,5-triazine with N,N'-bis(2,6-diisopropylphenyl)-1,7-dibromo-3,4,9,10-perylenetetracarboxylic diimide (monosubstitution)

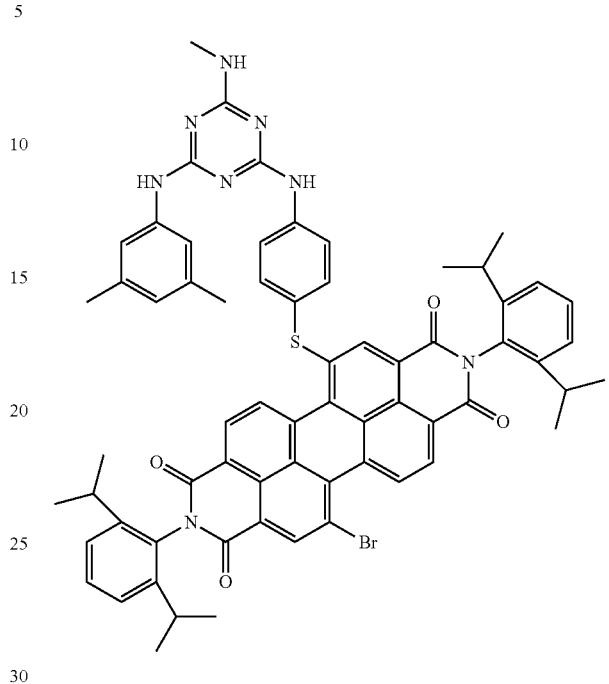

In a round-bottomed flask equipped with a magnetic stirrer, $K_2CO_3$ (0.795 g, 5.75 mmol) was suspended in THF (50 mL), then the mixture was sparged with nitrogen for 15 min. 2-mexylamino-4-methylamino-6-(4-mercaptophenylamino)-1,3,5-triazine (0.487 g, 1.38 mmol) and N,N'-bis(2,6-diisopropylphenyl)-1,7-dibromo-3,4,9,10-perylenetetracarboxylic diimide (1.00 g, 1.15 mmol) were then added, and the mixture was stirred at ambient temperature for 48 h under inert atmosphere. The volatiles were evaporated under reduced pressure, then the crude product was redissolved in minimal $CH_2Cl_2$, and the product was purified on a short silica plug using $CH_2Cl_2$ to remove unreacted starting material, then $CH_2Cl_2$/AcOEt 4:1, to give after thorough evaporation of the solvents 0.950 g pure title compound as a burgundy foam (0.833 mmol, 72%): $T_g$ 206° C.; FTIR ($CH_2Cl_2$/KBr) 3420, 3346, 3195, 3102, 3065, 3027, 2964, 2930, 2869, 1709, 1669, 1621, 1586, 1559, 1538, 1518, 1497, 1457, 1444, 1430, 1413, 1388, 1363, 1335, 1306, 1242, 1198, 1181, 1148, 1094, 1057, 1040, 1013, 995, 969, 937, 919, 885, 859, 838, 809, 793, 770, 749, 741, 714, 698, 668 cm$^{-1}$; $^1$H NMR (300 MHz, DMSO-$d_6$, 298 K): δ 9.50 (br s, 0.5H), 9.40 (br s, 0.5H), 9.34 (br d, 1H), 9.04 (br s, 0.5H), 8.92 (br s, 0.5H), 8.84 (s, 1H), 8.72 (d, $^3$J=7.6 Hz, 1H), 8.56 (d, $^3$J=7.0 Hz, 1H), 8.46 (br d, 1H), 8.25 (s, 1H), 7.97 (br s, 2H), 7.40 (m, 4H), 7.33 (d, $^3$J=7.0 Hz, 4H), 7.26 (d, $^3$J=7.0 Hz, 2H), 7.00 (br s, 1H), 6.46 (s, 1H), 2.84 (br d, 3H), 2.69 (m, 4H), 2.10 (s, 6H), 1.08 (d, $^3$J=5.9 Hz, 12H), 1.03 (d, $^3$J=5.9 Hz, 6H), 0.98 (d, $^3$J=6H) ppm; $^{13}$C NMR (75 MHz, DMSO-$d_6$): δ 165.9, 163.9, 163.6, 162.6, 162.1, 145.4, 145.2, 142.7, 142.6, 140.8, 140.7, 139.7, 137.1, 136.9, 135.3, 132.6, 132.3, 131.9, 131.7, 130.4, 129.3, 128.9, 128.6, 128.4, 128.2, 127.9, 127.0, 125.5, 123.7, 123.2, 122.2, 122.0, 121.6, 121.5, 120.5, 119.9, 117.8, 28.4, 27.2, 23.6, 21.0 ppm; HRMS (MALDI, MH$^+$) calcd. for $C_{66}H_{60}BrN_8O_4S$ (m/e): 1139.3642. found: 1139.3649.

Other Embodiments

From the foregoing description, it will be apparent to one of ordinary skill in the art that variations and modifications may be made to the embodiments described herein to adapt it to various usages and conditions.

What is claimed is:

1. A precursor compound having Formula 2:

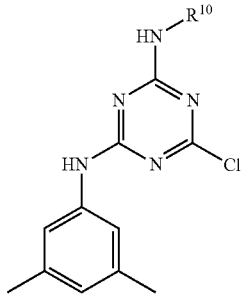

or a salt thereof,
wherein $R^{10}$ is $C_1$-$C_4$ alkyl, for example Me, Et or iPr.

2. The precursor compound, according to claim 1, is:

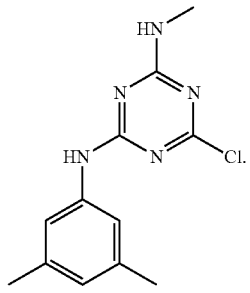 [SMILES: CNc1nc(Cl)nc(Nc2cc(C)cc(C)c2)n1]

3. A process for the preparation of the precursor compound of claim 2, comprising:
   a) dissolving 2-Methylamino-4,6-dichloro-1,3,5-triazine in a solvent to form a mixture;
   b) reacting the mixture at room temperature in the presence of a base so as to produce the precursor compound.

4. The process, according to claim 3, wherein the solvent is acetone or THF.

5. The process, according to claim 3, wherein the base is an alkylamine with an $R^{10}$ group, wherein $R^{10}$ is $C_1$-$C_4$ alkyl.

6. The process, according to claim 3, wherein the solvent is acetone and the base is 3,5-dimethylaniline.

7. A process for the preparation of the precursor compound of claim 2, comprising:
   a) dissolving 2-Mexylamino-4,6-dichloro-1,3,5-triazine in a solvent to form a mixture;
   b) reacting the mixture at room temperature in the presence of a base so as to produce the compound.

8. The process, according to claim 7, wherein the solvent is acetone or THF.

9. The process, according to claim 7, wherein the base is an alkylamine with an $R^{10}$ group, wherein $R^{10}$ is $C_1$-$C_4$ alkyl.

10. The process, according to claim 7, wherein the solvent is acetone and the base is methylamine.

* * * * *